US007947854B2

(12) United States Patent
Widmer et al.

(10) Patent No.: US 7,947,854 B2
(45) Date of Patent: May 24, 2011

(54) BIS-CATIONIC COMPOUNDS AND USE THEREOF

(75) Inventors: Alfred Werner Widmer, Ryde (AU); Katrina Anne Jolliffe, Chippendale (AU); Lesley Catherine Wright, North Turrumurra (AU); Tania Christine Sorrell, Riverview (AU)

(73) Assignee: The University of Sydney (AU)

( * ) Notice: Subject to any disclaimer, the term of this patent is extended or adjusted under 35 U.S.C. 154(b) by 708 days.

(21) Appl. No.: 10/579,263

(22) PCT Filed: Nov. 12, 2004

(86) PCT No.: PCT/AU2004/001570
§ 371 (c)(1),
(2), (4) Date: Jul. 1, 2008

(87) PCT Pub. No.: WO2005/047230
PCT Pub. Date: May 26, 2005

(65) Prior Publication Data
US 2008/0275003 A1 Nov. 6, 2008

(30) Foreign Application Priority Data
Nov. 13, 2003 (AU) .................. 2003906261

(51) Int. Cl.
*C07C 211/00* (2006.01)
*C07F 9/02* (2006.01)
(52) U.S. Cl. .......................... 564/511; 568/10
(58) Field of Classification Search .................. 564/511; 568/10
See application file for complete search history.

(56) References Cited

U.S. PATENT DOCUMENTS

| 3,925,556 A | 12/1975 | Bauman |
| 6,096,788 A | 8/2000 | Vial et al. |

FOREIGN PATENT DOCUMENTS

| EP | 0494613 A2 | 7/1992 |
| EP | 0630884 | 12/1994 |
| JP | 08 259427 | 10/1996 |
| JP | 2000/313171 | 11/2000 |
| WO | WO 98/04252 | 2/1998 |

OTHER PUBLICATIONS

Hcaplus 1984:510322 Abstract, Kocharyan et. al., "Studies on amines and ammonium compounds. CLXXIII. Reaction of ammonium salts containing a 4-methyl-4-petene-2-ynyl group with secondary amines", 1984.*
Salvino et. al., "Structure Activity Relationships of Non-Peptide Bradykinin B2 Receptor Antagonists", Bioorganic and Medicinal Chemistry Letters, vol. 5, No. 4, pp. 357-362, 1995.*
Tamaki et. al., "The Surface Activity of N, N'-Polymethylenebis (trialkylammonium) Dibromides in Aqueous Solutions", Bull. Chem. Soc. Jpn, 67, pp. 2867-2869 (1994).*

Zcaplus 1998:98316 abstract, "Preparation of alpha, w-bis (quaternary ammonium)alkane salt antimalarial and antibabesiasis agents", Vial et. al., 1998.*
Hcaplus 1984:510322 Abstract, "Studies on amines and ammonium compounds. CLXXIII. Reaction of ammonium salts containing a 4-methyl-4-penten-2-ynyl group with secondary amines", Kocharyan et. al., 1984.*
Database Crossfire Beilstein Beilstein Institut Zur Foerderung Der Chemischen Wissenschaften, Frankfurt Am Main, DE; XP002444007, Database accession No. 5689800, abstract, vol. 38, No. 5, 1983, pp. 308-310.
Database Crossfire Beilstein Beilstein Institut Zur Foerderung Der Chemischen Wissenschaften, Frankfurt Am Main, DE; XP002444008, Database accession No. 3801796, abstract, vol. 38, No. 5, 1983, pp. 308-310.
Database CA [Online] Chemical Abstracts Service, Columbus, Ohio, US; Yoshe, Makoto et al, "Dentifrices containing nonionic foaming agents and quaternary ammonium bactericides" XP002444009 retrieved from STN, Database accession No. 1997:2935, abstract, & JP08 259427, Oct. 8, 1996.
Database Crossfire Beilstein Beilstein Institut Zur Foerderung Der Chemischen Wissenschaften, Frankfurt Am Main, DE; XP002444010 Database accession No. 9239379, abstract, vol. 2, No. 16, 2002, pp. 2159-2162.
Blomquist, A.T., et. al., "Many-membered carbon rings. XX. Azacycloundecane via reduction of cyclodecanonoe oxime", Journal of the American Chemical Society, vol. 81, pp. 678-680, 1959, XP002443997.
Database CA [Online] Chemical Abstracts Service, Columbus, Ohio, US; Thesleff, Stephen et. al., "Differences in mode of nueromuscular blockade in a series of symmetric bis-quaternary ammonium salts", XP002444011, abstract, vol. 111, pp. 99-113, 1954.
Database CA [Online] Chemical Abstracts Service, Columbus, Ohio, US; Horner, L. et. al., "Corrosion inhibitors 25 (1). The role of the cation in a neutral salt in the corrosion of iron in the presence of oxygen" XP002444012, abstract, vol. 30(6), pp. 413-417, 1979.
Database Crossfire Beilstein Beilstein Institut Zur Foerderung Dr Chemischen Wissenschaften, Frankfurt Am Main, DE; XP002444013, abstract, vol. 3, 1948, p. 303.
Database Crossfire Beilstein Beilstein Institut Zur Foerderung Dr Chemischen Wissenschaften, Frankfurt Am Main, DE; XP002444014, abstract, vol. 59, No. 11, 1986, pp. 3663-3665.
Database Crossfire Beilstein Beilstein Institut Zur Foerderung Dr Chemischen Wissenschaften, Frankfurt Am Main, DE; XP002444015, abstract, vol. 67, No. 10, 1994, pp. 2867-2869.
Anclein M, et al., Potent inhibitors of Plasmodium phospholipid metabolism with a broad spectrum of in vitro, Antimircob. Agents Chemother. 47:2590-2597, 2003.
Ancelin M, et al., In vivo antimalarial activities of mono- and bis quaternary ammonum salts interfering with, Antimicrob. Agents Chemother. 147:2598-2605 (2003).

(Continued)

Primary Examiner — Janet L Andres
Assistant Examiner — Heidi Reese
(74) Attorney, Agent, or Firm — Quarles & Brady LLP

(57) ABSTRACT

The present invention relates to bis-cationic compounds comprising quaternary ammonium groups and/or quaternary phosphonium groups. The invention also relates to the use of bis-cationic compounds as Phospholipase B inhibitors and the use of bis cationic compounds for the treatment or prevention of microbial infection.

16 Claims, 7 Drawing Sheets

OTHER PUBLICATIONS

Calas M, et al., Antimalarial activity of molecules interfering with Plasmodium falciparum phospholipid metabolism, J Med Chem 40 3557-3566 1997.

Ganendren R, et al., In vitro antifungal activites of inhibitors of phospholipases from the fungal pathogen, Antimicrob. Agents Chemother. 48:1561-1569, 2004.

Chemical Abstract 123:180319, 1997.
Chemical Abstract 129:294300, 1998.
Chemical Abstract 132:116550, 1999.
Chemical Abstract 91:101848, 1979.
Chemical Abstract 130:38597, 1998.
Chemical Abstract 132:231503, 2000.

* cited by examiner

Additional enzymes acting on (mono-acyl)phospholipids:

- Lysophospholipid hydrolase
- Lysophospholipid transacylases
- Lysophospholipid acylase
- Lysolecithin acylmutase (migratase; 2,3-acylmutase)

1,12-Bis(tributylphosphonium)dodecane dibromide (1)

1,10-Bis(tributylammonium)decane dibromide (2)

1,12-Bis(tributylammonium)dodecane dibromide (3)

1,12-Bis(trimethylammonium)decane dichloride("decamethonium") (4)

BIS-CATIONIC COMPOUNDS AND USE THEREOF

TECHNICAL FIELD

The present invention relates to bis-cationic compounds comprising quaternary ammonium groups and/or quaternary phosphonium groups. The invention also relates to the use of bis-cationic compounds as Phospholipase B inhibitors and the use of bis-cationic compounds for the treatment or prevention of microbial infection.

BACKGROUND OF THE INVENTION

There is a need in therapy and industry for improved antimicrobial agents. The phospholipase(s) have attributes of virulence factors and thus, may be a useful target for at least one of treatment, inhibition and prevention of microbial infection, such as fungal, bacterial, viral or parasitic, infection.

Hanel et al (*Mycosis*, 1995, 38:252-264) investigated the role of fungal phospholipases as drug targets in a mouse model of *Candida albicans* infection. Mice were treated with beta blockers and related compounds which inhibited secretory phospholipase activity on egg yolk plate assays. However, as discussed by Ashraf et al. Microbiology (1997), 143, 331-340, the assays used by Hanel et al are not specific for phospholipases.

Some bis-cationic compounds ammonium are known to have anticholinergic and neuromuscular blocking properties (e.g. Merck Index 13th Edition (2001), MERCK & CO, Inc., Whitehouse Station N.J. USA; Entry number 4364, page 772 Gallamine; Entry number 4660, page 828 Hemicholinium; Entry number 9878, page 1746 Tubocurarine).

Other bis-cationic ammonium compounds are known to behave as "Gemini" surfactants, as described for example in S. M. Menger and J. S. Keiper, *Angew. Chem. Int. Ed.*, 2000, 39, 1906-1920.

The present invention relates to bis-cationic compounds comprising quaternary ammonium groups and/or quaternary phosphonium groups and their use as antimicrobial agents.

SUMMARY OF THE INVENTION

According to a first aspect of the invention there is provided a compound of Formula (I)

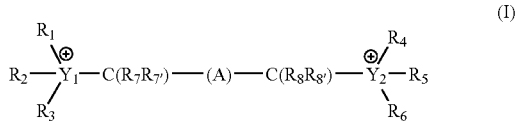

wherein $Y_1$ and $Y_2$ may be the same or different and are independently selected from N and P;

$R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted aralkyl, optionally substituted heteroaryl, and optionally substituted heterocycloalkyl, wherein said substituents are independently selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy$C_{1-6}$ alkyl, aryl, OC(O)Ph, and $=C(Ph)_2$; or $R_1$ and $R_2$ together with the $Y_1$ group to which they are attached, or $R_1$, $R_2$ and $R_3$ together with the $Y_1$ group to which they are attached may optionally form a heterocycloalkyl group; and $R_4$ and $R_5$ together with the $Y_2$ group to which they are attached, or $R_4$, $R_5$ and $R_6$ together with the $Y_2$ group to which they are attached may optionally form a heterocycloalkyl group; wherein each of said heterocycloalkyl groups may be optionally substituted with one or more groups selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy $C_{1-6}$ alkyl, aryl, OC(O)Ph, and $=C(Ph)_2$;

$R_7$, $R_{7'}$, $R_8$ and $R_{8'}$ may be the same or different and are independently selected from hydrogen, F and Cl;

A comprises one or more groups selected from optionally substituted alkylene, optionally substituted alkenylene, optionally substituted alkynylene, optionally substituted phenyl, optionally substituted $C_{5-7}$ cycloalkyl, and —C(O)—, wherein the length of A is from 5 to 18 carbon atoms, and wherein the substituents are independently selected from $C_{1-6}$ alkyl, $C_{2-6}$ alkenyl, $C_{2-6}$ alkynyl, hydroxyl, halogen, $NO_2$, $C(O)R_{10}$, $OR_{11}$, $CH_2OR_{11}$, $CH_2NR_{12}R_{13}$, $SR_{11}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, and optionally substituted aralkyl, wherein said optional substituents are independently selected from $C_{1-4}$ alkyl, hydroxyl and halogen;

$R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aralkyl, optionally substituted alkylheteroaryl, wherein said substituents are independently selected from $C_{1-4}$ alkyl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-4}$ alkyl, hydroxyl, halogen, amino, and $C(O)OR_{11}$;

and salts thereof, provided that the compound of formula (I) is not selected from the following:

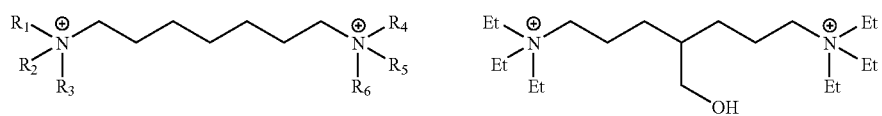

R1 = R2 = R3 = R4 = R5 = R6 = Me, Et,
R1 = R2 = R4 = R5 = Me, R3 = R6 = Et, Pr
R1 = R2 = R4 = R5 = Et, R3 = R6 = Me
R1 = R2 = R4 = R5 = Pr, R3 = R6 = Me
R1 = R2 = R4 = R5 = allyl, R3 = R6 = Me -continued

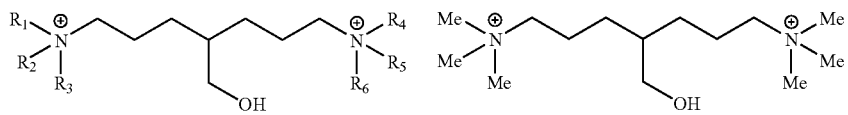

R1 = R2 = R4 = R5 = Me, R3 = R6 = Pr
R1 = R2 = R4 = R5 = Pr, R3 = R6 = Me

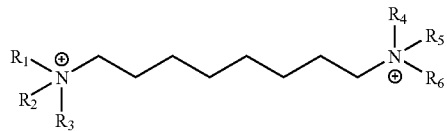

R1 = R2 = R3 = R4 = R5 = R6 = Me, Et, Pr, Bu, pentyl, allyl
R1 = R2 = R4 = R5 = Me, R3 = R6 = Pr, Bu, Decyl
R1 = R4 = Me, R2 = R3 = R5 = R6 = Hexyl, allyl
R1 = R4 = Me, R2 = R5 = Bu, R3 = R6 = octyl

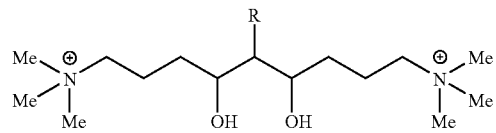

R1 = R2 = R3 = R4 = R5 = R6 = n-Bu, t-Bu, octyl

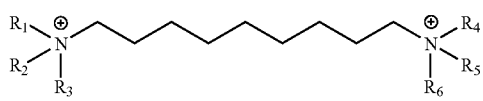

R1 = R2 = R3 = R4 = R5 = R6 = Me, Et, allyl
R1 = R2 = R4 = R5 = Me, R3 = R6 = Pr, pentyl
R1 = R2 = R4 = R5 = allyl, R3 = R6 = Et

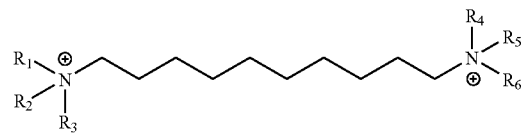

R = Pr, H, pentyl, hexyl, butyl, Me, Et

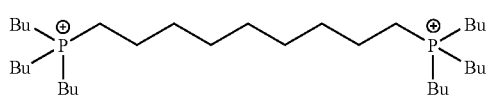

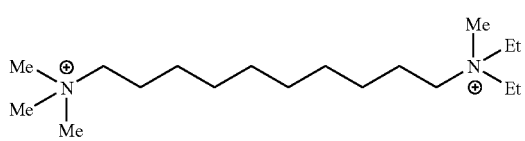

R1 = R2 = R3 = R4 = R5 = R6 = Me, Pr, pentyl, butyl, allyl, ethyl, hexyl
R1 = R2 = R3 = R4 = R5 = R6 = Bu, Et, hexyl, heptyl, pentyl, propyl, decyl, i-Pr, octyl
R1 = R4 = Me, R2 = R3 = R5 = R6 = allyl, ethyl
R1 = R2 = R4 = R5 = Et, R3 = R6 = hexyl

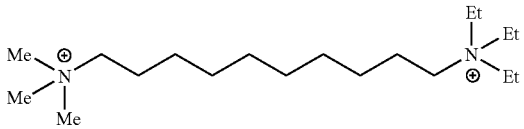

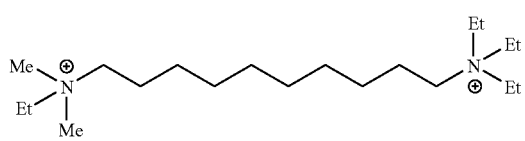

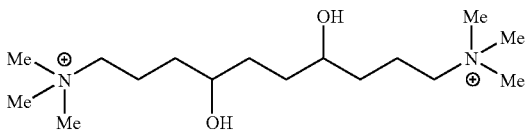

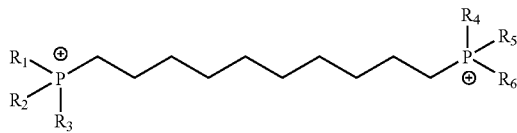

R1 = R2 = R3 = R4 = R5 = R6 = Me, Et, Bu, octyl

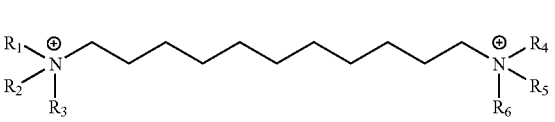

R1 = R2 = R3 = R4 = R5 = R6 = Me, Et
R1 = R2 = R4 = R5 = Me, R3 = R6 = pentyl

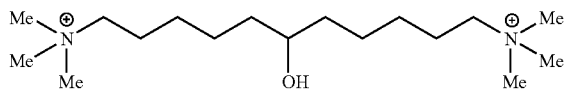

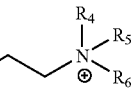

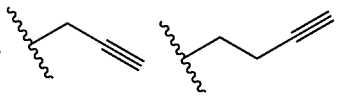

R1 = R2 = R3 = R4 = R5 = R6 = Bu, Et, Pr
R1 = R2 = R4 = R5 = Me, R3 = R6 = Bu, Et, heptyl, nonyl,
R1 = R2 = R4 = R5 = allyl, R3 = R6 = Me, Et
R1 = R2 = R4 = R5 = hexyl, R3 = R6 = Me

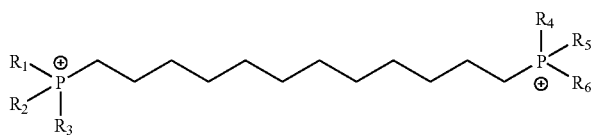
R1 = R2 = R3 = R4 = R5 = R6 = octyl, butyl
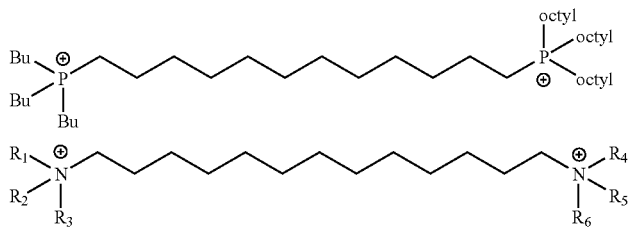
R1 = R2 = R3 = R4 = R5 = R6 = Me, Et
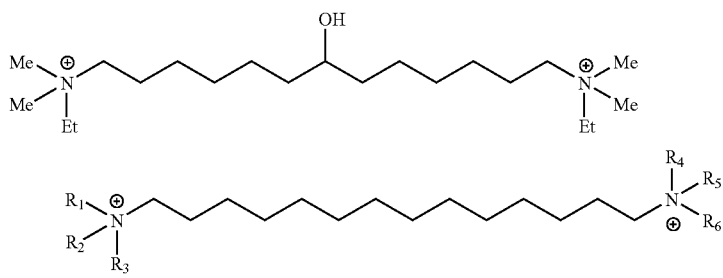
R1 = R2 = R3 = R4 = R5 = R6 = Me, Et, Pr
R1 = R2 = R4 = R5 = Me, R3 = R6 =
R1 = R4 = Me, R2 = R5 = Et, R3 = R6 = Pr
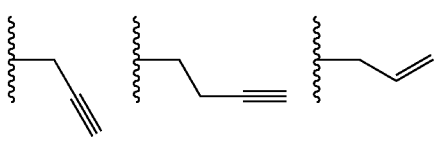
R1 = R2 = R3 = R4 = R5 = R6 = Et
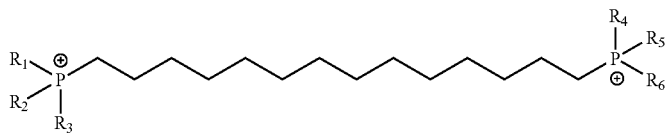
R1 = R2 = R3 = R4 = R5 = R6 = Me, Et, Bu
R1 = R4 = Me, R2 = R5 = Et, R3 = R6 = Pr
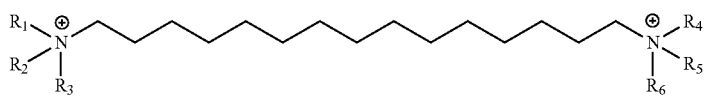
R1 = R2 = R3 = R4 = R5 = R6 = Me, Et, Pr, allyl
R1 = R2 = R4 = R5 = Me, R3 = R6 = Et
R1 = R2 = R4 = R5 = Et, R3 = R6 = Me
R1 = R4 = Me, R2 = R5 = Et, R3 = R6 = Pr
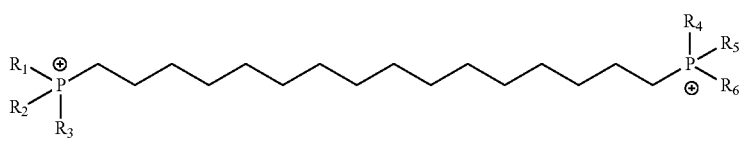
R1 = R2 = R3 = R4 = R5 = R6 = Et -continued
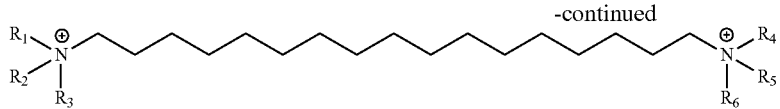
R1 = R2 = R3 = R4 = R5 = R6 = Me, Et
R1 = R4 = Me, R2 = R5 = Et, R3 = R6 = Pr
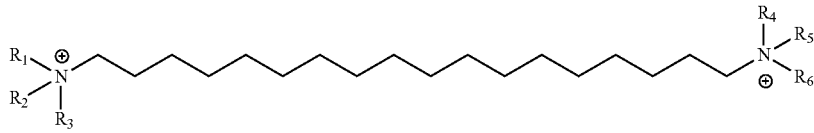
R1 = R2 = R3 = R4 = R5 = R6 = Me, Et
R1 = R2 = R4 = R5 = Et, R3 = R6 = Me
R1 = R4 = Me, R2 = R5 = Et, R3 = R6 = Pr
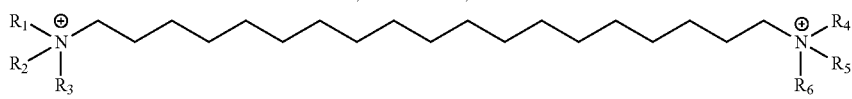
R1 = R2 = R3 = R4 = R5 = R6 = Me, Et
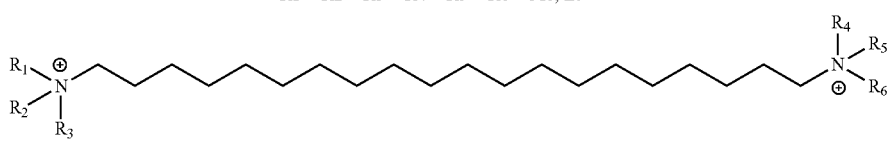
R1 = R2 = R3 = R4 = R5 = R6 = Me, Et, Pr
R1 = R4 = Me, R2 = R5 = Et, R3 = R6 = Pr
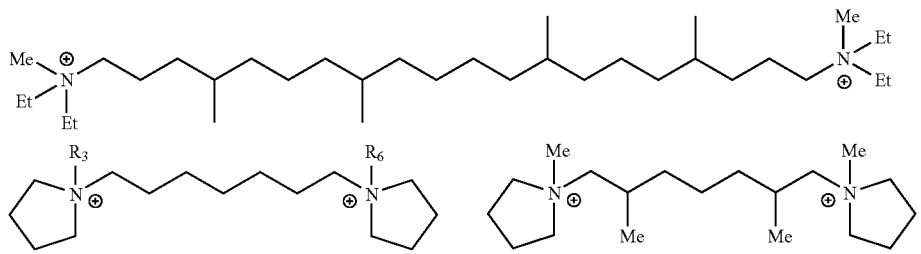
R3 = R6 = Me, Bu
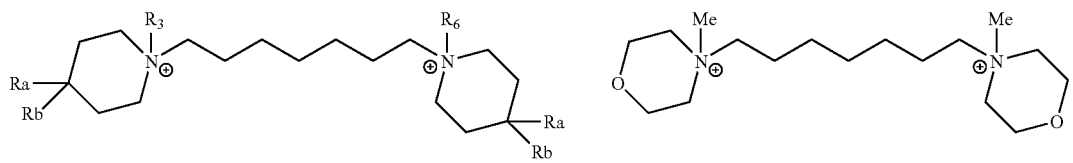
R3 = R6 = Me; Ra, Rb = H
R3 = R6 = Me, Ra = Ph, Rb = CO$_2$Et
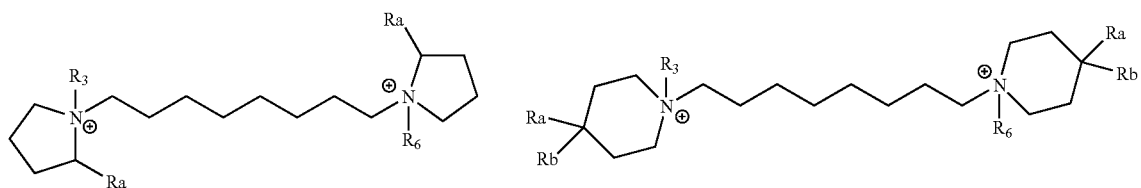
R3 = R6 = Me, Ra = H
R3 = R6 = Me, Ra = Me
R3 = R6 = Me, Ra = Et
R3 = R6 = Me, Ra = Ph, Rb = CO$_2$Et
R3 = R6 = Me, Ra, Rb = =CPh$_2$
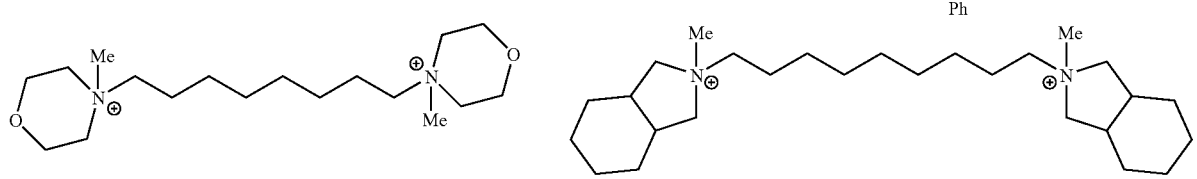

-continued
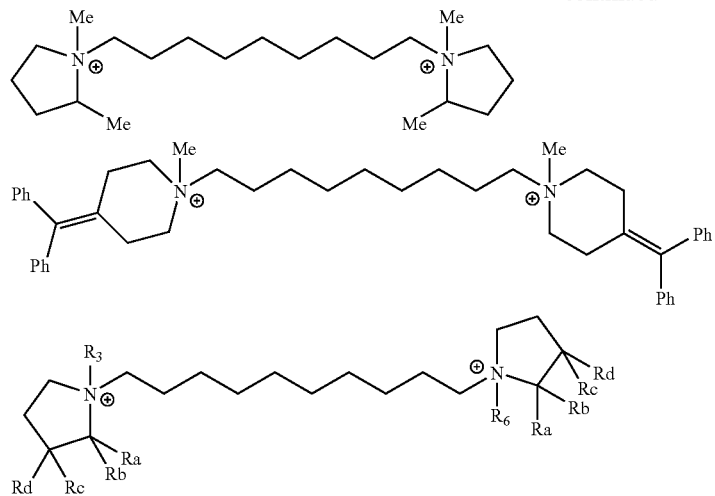
R3 = R6 = Me, Ra, Rb, Rc, Rd = H
R3 = R6 = Me, Ra = Me, Rb, Rc, Rd = H
R3 = R6 = Ra = Rb = Rc = Rd = Me
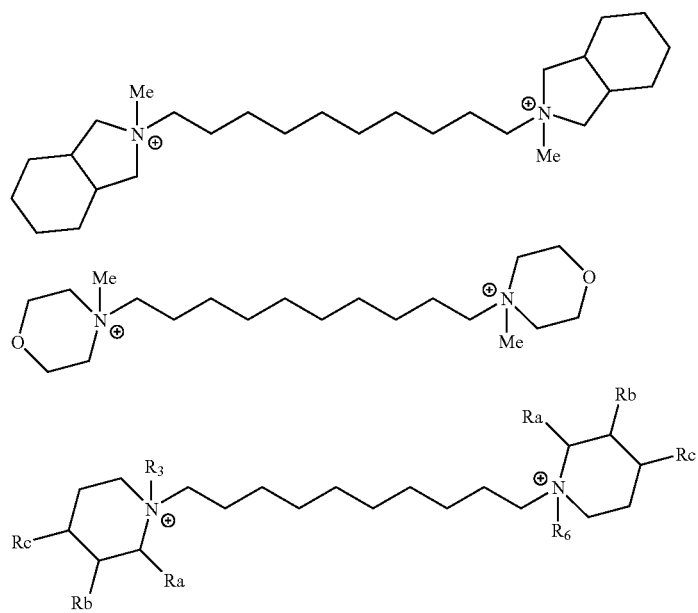
R3 = R6 = Me, Ra = Me, Rb = Rc = H
R3 = R6 = Me, Ra = Et, Rb = Rc = H
R3 = R6 = Et, Ra = H, Rb = OH, Rc = H
R3 = R6 = Me, Ra = Rb = Rc = H
R3 = R6 = Me, Ra = Rb = Rc = H
R3 = R6 = Me, Ra = H, Rb = OC(=O)Pr, Rc = H
R3 = R6 = Me, Ra = H, Rb = OAc, Rc = H
R3 = R6 = Me, Ra = Rb = H, Rc = OC(O)Ph
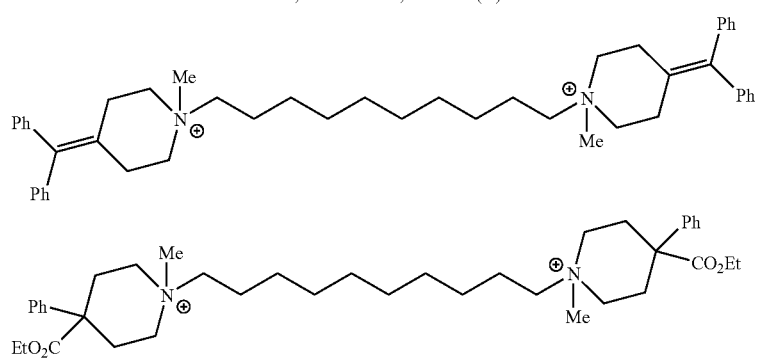

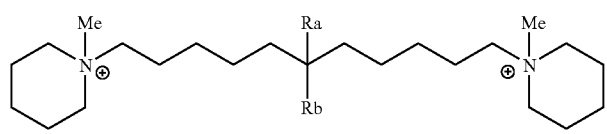
Ra, Rb = H
Ra = Me, Rb = Et
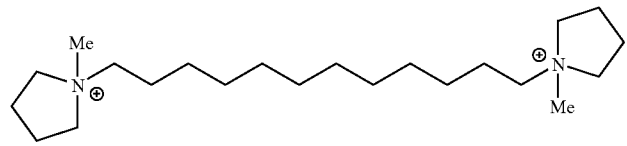
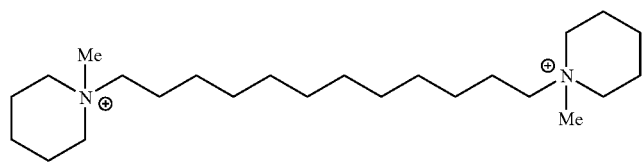
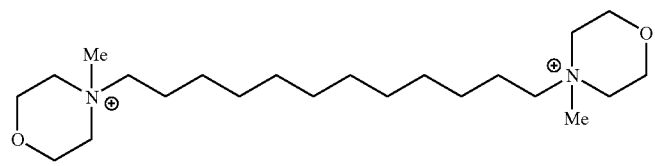
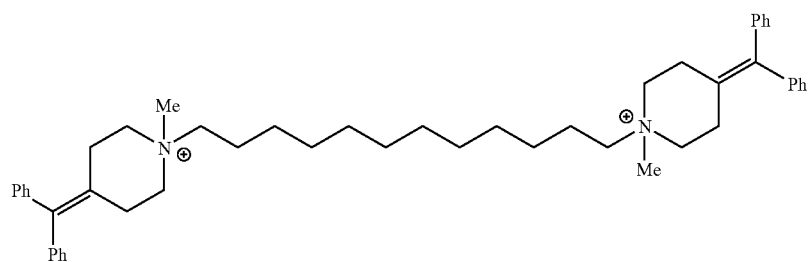
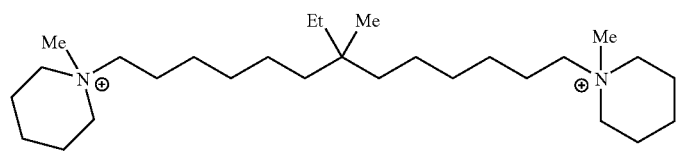
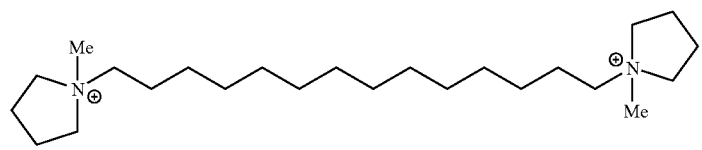
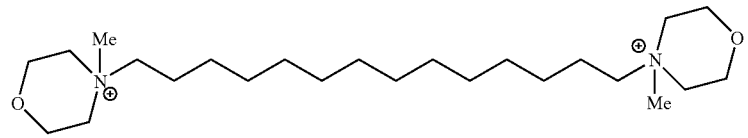
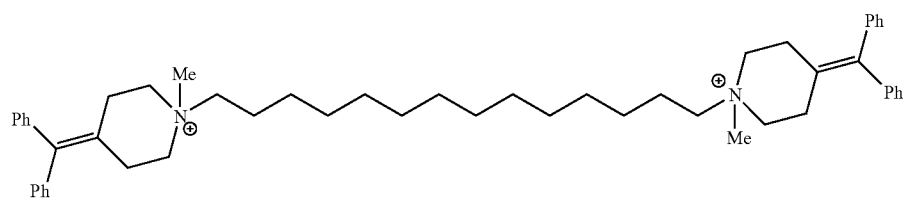

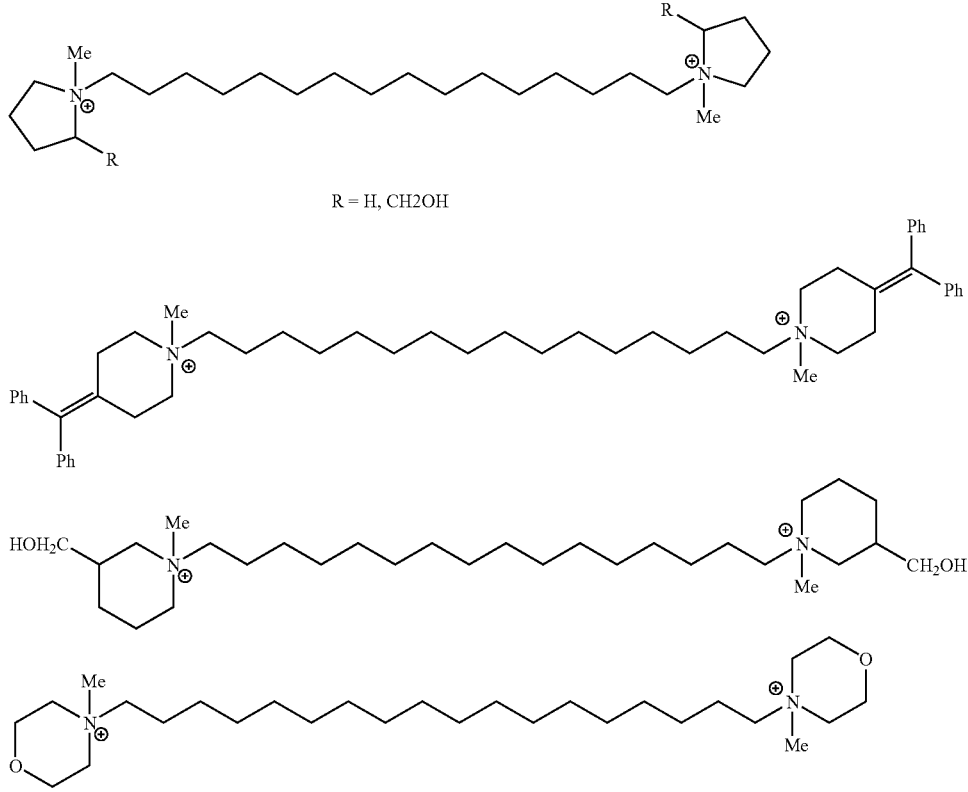

R = H, CH2OH

In one embodiment of the invention $Y_1$ is N and $Y_2$ is N. In another embodiment of the invention, $Y_1$ is N and $Y_2$ is P. In another embodiment of the invention, $Y_1$ is P and $Y_2$ is N. In a further embodiment of the invention $Y_1$ is P and $Y_2$ is P.

$R_1$ to $R_6$ may be the same or different and in one embodiment are independently selected from optionally substituted $C_{2-10}$ alkyl. In another embodiment, $R_1$ to $R_6$ are independently selected from optionally substituted $C_{2-10}$ alkyl. In a further embodiment, $R_1$ to $R_6$ are independently selected from optionally substituted $C_{3-6}$ alkyl.

In one embodiment of the invention, $Y_1$ and $Y_2$ are each N, and $R_1$ to $R_6$ are independently selected from $C_{2-10}$ alkyl.

In some embodiments of the invention, the relative lengths of $R_1$, $R_2$ and $R_3$ may vary by 2 to 6 carbons with respect to each other, for example, by 2, 3, 4, 5 or 6 carbons. In other embodiments of the invention, the relative lengths of $R_1$, $R_2$ and $R_3$ may vary by 3 or 4 carbons. In some embodiments of the invention, the relative lengths of $R_4$, $R_5$ and $R_6$ may vary by 2 to 6 carbons with respect to each other, for example, by 2, 3, 4, 5 or 6 carbons. In other embodiments of the invention, the relative lengths of $R_4$, $R_5$ and $R_6$ may vary by 3 or 4 carbons.

In one embodiment of the invention $R_1$ to $R_3$ are the same. In another embodiment $R_4$ to $R_6$ are same. In a further embodiment, $R_1$ to $R_6$ are the same.

In one embodiment of the invention the length of A is from 5 to 9 carbon atoms.

In one embodiment, when $Y_1$ and $Y_2$ are each N, $R_1$ to $R_6$ are each $C_{1-10}$ alkyl, $R_7$, $R_{7'}$, $R_8$, and $R_{8'}$ are each hydrogen, then A is not $C_{10-18}$ alkylene substituted with a $C_{1-3}$ alkyl substituent. In another embodiment of the invention, when $Y_1$ and $Y_2$ are each N, $R_1$ to $R_6$ are each $C_{1-10}$ alkyl, $R_7$, $R_{7'}$, $R_8$, and $R_{8'}$ are each hydrogen, then A is $C_{10-18}$ alkylene substituted with a $C_{1-3}$ alkyl substituent and at least one other substituent.

In a further embodiment of the invention, when $Y_1$ and $Y_2$ are each N; $R_3$ and $R_6$ are each $C_{1-10}$ alkyl; $R_1$ and $R_2$ together with the N to which they are attached, and $R_4$ and $R_5$ together with the N to which they are attached are each a 4- or 5-membered heterocycloalkyl ring comprising one S or O, substituted with hydroxy$C_{1-3}$ alkyl or halo$C_{1-3}$ alkyl; $R_7$, $R_{7'}$, $R_8$, and $R_{8'}$ are each hydrogen, then A is not $C_{10-18}$ alkylene substituted with a $C_{1-3}$ alkyl substituent.

In one embodiment of the invention, A may comprise one or more alkylene groups "$(CR_9R_{9a})_n$", wherein $R_9$ and $R_{9a}$ may be the same or different and are independently selected from the group consisting of hydrogen, halogen, $C_{1-6}$ alkyl, $C_{2-6}$ alkenyl, C(O)$R_{10}$, OR$_{11}$, CH$_2$OR$_{11}$, CH$_2$OH, SR$_{11}$, NR$_{12}$R$_{13}$, CON$_{12}$R$_{13}$, OH, SH, amino acids, dipeptidyl, tripeptidyl, tetrapeptidyl and pentapeptidyl, and wherein n is an integer selected from 1 to 18. For example, n may be 1, 2, 3, 4, 5, 6, 7, 8, 9, 10, 11, 12, 13, 14, 15, 16, 17, or 18, provided that the total length of A is from 5 to 18 carbons. In one embodiment, n is an integer from 5 to 18.

In one embodiment of the invention, A comprises one or more groups selected from optionally substituted alkylene (including optionally substituted methylene "CR$_9$R$_{9a}$"), optionally substituted phenyl, and optionally substituted $C_{5-6}$ cycloalkyl, wherein said substituents are independently selected from $C_{1-6}$ alkyl, hydroxyl and halogen. In one embodiment of the invention, A comprises at least one alkylene group "CR$_9$R$_{9a}$". In one embodiment of the invention, A comprises at least one phenylene. In another embodiment of the invention, A comprises at least one cyclohexylene.

In one embodiment of the invention, $R_9$ and $R_{9a}$ are both hydrogen. In another embodiment, $R_9$ is hydrogen and $R_{9a}$ is selected from hydrogen, $C_{1-6}$ alkyl, C(O)$R_{10}$, OR$_{11}$, CONR$_{11}$R$_{12}$, NR$_{12}$R$_{13}$, OH and SH. For example, in one embodiment of the invention, $R_9$ is hydrogen and $R_{9a}$ is hydrogen, methyl, ethyl, propyl, butyl, pentyl, hexyl, COOH, $CO_2Me$, $CO_2Et$, $CO_2Bu$, CONHMe, $CONMe_2$, CONHEt, $CONEt_2$, $CONH(CH_2Ph)$, $CON(CH_2Ph)_2$, $CO_2BU^t$, OMe, OEt, $NMe_2$, or $NEt_2$.

A may be unsubstituted $C_{8-12}$ or $C_{5-9}$ alkylene, or optionally substituted $C_{8-12}$ or $C_{5-9}$ alkylene. A may be unsubstituted $C_{8-12}$ or $C_{5-9}$ alkenylene or optionally substituted $C_{8-12}$ or $C_{5-9}$ alkenylene. In one embodiment of the invention, A is unsubstituted $C_{8-12}$ or $C_{5-9}$ alkylene or $C_{8-12}$ or $C_{5-9}$ unsubstituted alkenylene.

In one embodiment of the invention, n is 8, 9 or 10, each A is $CR_9R_{9a}$, and $R_9$ and $R_{9a}$ are each hydrogen.

In some embodiments, $R_{12}$ and $R_{13}$, together with the nitrogen atom to which they are attached may form an optionally substituted heterocycloalkyl ring. For example, the is group $NR_{12}R_{13}$ may optionally be 3-aminopyrrolidinyl, 3-aminoquinuclidinyl, 3-aminopyridinyl, 1-(3-aminopropyl)-2-pipecolinyl groups.

In one embodiment of the invention the compound is a compound of Formula (Ia):

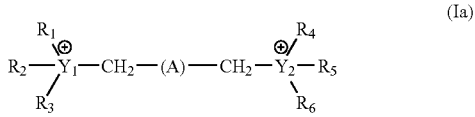

(Ia)

wherein $Y_1$ and $Y_2$ may be the same or different and are independently selected from N and P;

$R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted heteroaryl, and optionally substituted heterocycloalkyl, wherein said substituents are independently selected from $C_{1-4}$ alkyl, $C_{2-6}$ alkenyl, hydroxyl, halogen, $O(C_{1-6}$ alkyl), $C(O)O(C_{1-6}$ alkyl), $NO_2$, amino, hydroxy $C_{1-6}$ alkyl, aryl, and OC(O)Ph; or $R_1$ and $R_2$ together with the $Y_1$ group to which they are attached may optionally form a heterocycloalkyl group; and $R_4$ and $R_5$ together with the $Y_2$ group to which they are attached may optionally form a heterocycloalkyl group; wherein each of said heterocycloalkyl groups may be optionally substituted with one or more groups selected from $C_{1-6}$ alkyl, $C_{2-4}$ alkenyl, hydroxyl, halogen, $O(C_{1-6}$ alkyl), $C(O)O(C_{1-6}$ alkyl), amino, hydroxy $C_{1-6}$ alkyl, and aryl;

A comprises one or more groups selected from optionally substituted alkylene, optionally substituted alkenylene, and optionally substituted phenyl, wherein the length of A is from 5 to 18 carbon atoms, and wherein the substituents are independently selected from $C_{1-6}$ alkyl, $C_{2-4}$ alkenyl, $C_{2-6}$ alkynyl, halogen, $C(O)R_{10}$, $OR_{11}$, $SR_{11}$, $CH_2OR_{11}$, $CH_2NR_{12}R_{13}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, and optionally substituted $C_{3-10}$ cycloalkyl, wherein said optional substituents are independently selected from $C_{1-6}$ alkyl, $C_{2-6}$ alkenyl, aryl, and hydroxyl;

$R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted alkylheteroaryl, wherein said substituents are independently selected from $C_{1-6}$ alkyl, $C_{2-6}$ alkenyl, aryl, hydroxyl, halogen, amino, and $C(O)OR_{11}$; or $R_{12}$ and $R_{13}$, together with the nitrogen atom to which they are attached may form an optionally substituted heterocycloalkyl group or heteroaryl group, wherein said substituents are independently selected from $C_{1-6}$ alkyl, $C_{2-6}$ alkenyl, hydroxyl, halogen, amino, and $C(O)OR_{11}$, and salts thereof.

Also disclosed herein are compounds of Formula (II):

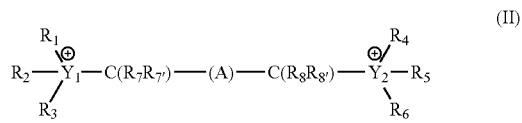

(II)

wherein $Y_1$ and $Y_2$ may be the same or different and are independently selected from N and P;

$R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted aralkyl, optionally substituted heteroaryl, and optionally substituted heterocycloalkyl, wherein said substituents are independently selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl), $NO_2$, amino, hydroxy $C_{1-6}$ alkyl, aryl, OC(O)Ph, and $=C(Ph)_2$; or $R_1$ and $R_2$ together with the $Y_1$ group to which they are attached, or $R_1$, $R_2$ and $R_3$ together with the $Y_1$ group to which they are attached may optionally form an heterocycloalkyl group; and $R_4$ and $R_5$ together with the $Y_2$ group to which they are attached, or $R_4$, $R_5$ and $R_6$ together with the $Y_2$ group to which they are attached may optionally form a heterocycloalkyl group; wherein each of said heterocycloalkyl groups may be optionally substituted with one or more groups selected from $C_{1-6}$ alkyl, $C_{2-6}$ alkenyl, $C_{2-6}$ alkynyl, hydroxyl, and halogen, $O(C_{1-6}$ alkyl), $C(O)O(C_{1-6}$ alkyl), $NO_2$, amino, hydroxy $C_{1-6}$ alkyl, aryl, and $=C(Ph)_2$;

$R_7$, $R_{7'}$, $R_8$ and $R_{8'}$ may be the same or different and are independently selected from hydrogen, F and Cl;

A comprises one or more groups selected from optionally substituted alkylene, optionally substituted alkenylene, optionally substituted phenyl, optionally substituted $C_{5-7}$ cycloalkyl, and —C(O)—, wherein the length of A is from 4 to 18 carbon atoms, wherein the substituents are independently selected from $C_{1-6}$ alkyl, $C_{2-6}$ alkenyl, hydroxyl, halogen, nitro, $C(O)R_{10}$, $OR_{11}$, $CH_2OR_{11}$, $CH_2NR_{12}R_{13}$, $SR_{11}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl, optionally substituted amino-$C_{1-6}$-alkylsulfonate, optionally substituted amino-$C_{1-6}$-alkylphosphonate, optionally substituted amino-$C_{1-6}$-alkyl-guanidinyl, and optionally substituted amino-$C_{1-6}$-alkyl-tri($C_{1-6}$-alkyl)ammonium;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted arylalkyl, optionally substituted amino-$C_{1-6}$-alkylsulfonate, optionally substituted amino-$C_{1-6}$-alkylphosphonate, optionally substituted amino-$C_{1-6}$- alkyl-guanidinyl, and optionally substituted amino-$C_{1-6}$-alkyl-tri($C_{1-6}$-alkyl)ammonium, wherein said optional substituents are independently selected from $C_{1-4}$ alkyl, hydroxyl and halogen $R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted arylalkyl, optionally substituted alkylheteroaryl, optionally substituted amino-$C_{1-6}$-alkylsulfonate, optionally substituted amino-$C_{1-6}$-alkylphosphonate, optionally substituted amino-$C_{1-6}$-alkyl-guanidinyl, and optionally substituted amino-$C_{1-6}$-alkyl-tri($C_{1-6}$-alkyl)ammonium, wherein said substituents are independently selected from $C_{1-3}$ alkyl, hydroxyl, halogen, amino, and C(O)$OR_{11}$; or $R_{12}$ and $R_{13}$, together with the nitrogen atom to which they are attached may form an optionally substituted heterocycloalkyl group, wherein said substituents are independently selected from $C_{1-3}$ alkyl, hydroxyl, halogen, amino, and C(O)$OR_{11}$.

With reference to Formula (II), the group amino-$C_{1-6}$-alkylsulfonate includes for example, aminomethyl-sulfonate (i.e a "—NH—$CH_2$—$SO_3$—" group), aminoethyl-sulfonate and aminopropyl-sulfonate; amino-$C_{1-6}$-alkylphosphonate includes for example, aminomethyl-, aminoethyl- and aminopropyl-phosphonate; amino-$C_{1-6}$-alkyl-guanidinyl includes for example, 4-aminobutyl-guanidinyl; amino-$C_{1-6}$-alkyl-tri($C_{1-6}$-alkyl)ammonium includes for example 1-(3-aminopropyl)trimethylammonium.

$R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl and optionally substituted aralkyl, wherein said substituents are independently selected from $C_{1-6}$ alkyl, hydroxyl and halogen; or $R_1$ and $R_2$ together with the $Y_1$ group to which they are attached, or $R_1$, $R_2$ and $R_3$ together with the $Y_1$ group to which they are attached may optionally form a heterocycloalkyl group; and $R_4$ and $R_5$ together with the $Y_2$ group to which they are attached, or $R_4$, $R_5$ and $R_6$ together with the $Y_2$ group to which they are attached may optionally form a heterocycloalkyl group; wherein said heterocycloalkyl group may be optionally substituted with one or more groups selected from $C_{1-6}$ alkyl, hydroxyl and halogen;

A may comprise one or more groups selected from optionally substituted methylene groups "$CR_9R_{9a}$", optionally substituted phenyl, and optionally substituted $C_{5-7}$ cycloalkyl, wherein the length of A is from 4 to 18 carbon atoms, and wherein said substituents are independently selected from $C_{1-6}$ alkyl, hydroxyl and halogen;

$R_9$ and $R_{9a}$ may be the same or different and are independently selected from the group consisting of hydrogen, halogen, $C_{1-6}$ alkylene, $C_{1-6}$ alkenylene, C(O)$R_{10}$, $OR_{11}$, $SR_{11}$, $NR_{12}R_{13}$, $CON_{12}R_{13}$, amino acids, dipeptidyl, tripeptidyl, tetrapeptidyl and pentapeptidyl;

$R_{10}$ is OH or $OR_{11}$;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, and optionally substituted aralkyl, wherein said substituents are independently selected from $C_{1-6}$ alkyl, hydroxyl and halogen;

$R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted heterocycloalkyl, optionally substituted heteroaralkyl, and optionally substituted aralkyl, wherein said substituents are independently selected from $C_{1-6}$ alkyl, hydroxyl, halogen, and C(O)$OR_{11}$; or $R_{12}$ and $R_{13}$ together with the N to which they are attached may optionally form a heterocycloalkyl group.

In one embodiment of the invention, the compound is a compound of Formula (I) or (II) wherein $R_7$, $R_{7'}$, $R_8$, and $R_{8'}$ are each hydrogen; A is optionally substituted $C_{8-10}$ alkylene and $R_1$ to $R_3$ are each butyl. In another embodiment, the compound is a compound of Formula (I) or (II) wherein $R_7$, $R_{7'}$, $R_8$, and $R_{8'}$ are each hydrogen, A is unsubstituted $C_{8-10}$ alkylene, and $R_1$ to $R_3$ are each butyl.

According to a second aspect of the invention there is provided the use of at least one compound of Formula (I) or Formula (II) for the manufacture of a medicament for one or more of treating, inhibiting and preventing a microbial infection.

The microbial infection may comprise one or more of bacteria, fungi, viruses, and parasites.

According to a third aspect of the invention there is provided a method for one or more of treating, inhibiting, and preventing a microbial infection in a vertebrate, said method comprising administering to said vertebrate an effective amount of at least one compound of Formula (I) or Formula (II).

According to a fourth aspect of the invention there is provided a method for one or more of treating, inhibiting, and preventing a microbial infection of a plant, said method comprising contacting said plant with an effective amount of at least one compound of Formula (I) or Formula (II).

According to a fifth aspect of the invention there is provided an antimicrobial composition comprising at least one compound of Formula (I) or a compound of Formula (II), together with an industrially, veterinarially, agriculturally, or pharmaceutically suitable carrier, diluent or carrier.

With reference to the fifth aspect of the invention, the composition may be one or more of an antifungal, antibacterial, antiviral and antiparasitic composition. In one embodiment the composition is an antifungal composition. In another embodiment the composition is an antibacterial composition.

According to a sixth aspect of the invention there is provided a pharmaceutical composition comprising at least one compound of Formula (I) or Formula (II) together with a pharmaceutically effective carrier, adjuvant or diluent.

According to a seventh aspect of the invention there is provided a method of inhibiting phospholipase in an organism comprising contacting said organism with an effective amount of at least one compound of Formula (I) or at least one compound of Formula (II), or a composition according to the fourth or fifth aspect of the invention.

With reference to the seventh aspect of the invention, the organism may be a microbial organism such as bacteria, fungi, virus, or a parasite, including for example protozoa. The phospholipase may be Phospholipase B.

According to an eighth aspect of the invention there is provided a method for identifying an antimicrobial agent comprising contacting microbial cells with a compound suspected of having antimicrobial properties, determining whether said compound inhibits a microbial phospholipase enzyme, wherein inhibition of said phospholipase enzyme indicates antimicrobial activity, and thereby identifying an antimicrobial agent.

With reference to the seventh aspect of the invention, the compound may be a compound of Formula (I) or Formula (II) as defined herein. The phospholipase may be Phospholipase B.

In accordance with a ninth aspect of the invention there is provided a compound of Formula (I) or a compound of Formula (II) or a composition according to the fiftih or sixth aspect of the invention, when used for one or more of treating, inhibiting or preventing a microbial infection or a parasitic infection.

DEFINITIONS

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In the context of this specification, the term "amino acid" is defined as having at least one primary, secondary, tertiary or quaternary amino group, and at least one acid group, wherein the acid group may be a carboxylic, sulfonic, or phosphonic acid, or mixtures thereof. The amino groups may be "alpha", "beta", "gamma" . . . to "omega" with respect to the acid group(s). The backbone of the "amino acid" may be substituted with one or more groups selected from halogen, hydroxy, guanido, heterocyclic groups. Thus term "amino acids" also includes within its scope glycine, alanine, valine, leucine, isoleucine, methionine, proline, phenylalanine, tryptophane, serine, threonine, cysteine, tyrosine, asparagine, glutamine, asparte, glutamine, lysine, arginine and histidine, taurine, betaine, N-methylalanine etc. (L) and (D) forms of amino acids are included in the scope of this invention.

As used herein, the term "alkyl group" includes within its meaning monovalent ("alkyl") and divalent ("alkylene") straight chain or branched chain saturated aliphatic groups having from 1 to 10 carbon atoms, eg, 1, 2, 3, 4, 5, 6, 7, 8, 9, or 10 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "alkenyl group" includes within its meaning monovalent ("alkenyl") and divalent ("alkenylene") straight or branched chain unsaturated aliphatic hydrocarbon groups having from 2 to 10 carbon atoms, eg, 2, 3, 4, 5, 6, 7, 8, 9, or 10 carbon atoms, Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butenyl, 1,3-butadienyl, 1-pentenyl, 2-pentenyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptenyl, 3-heptenyl, 1-octenyl, 1-nonenyl, 1-decenyl, and the like.

The term "alkynyl group" as used herein includes within its meaning monovalent ("alkynyl") and divalent ("alkynylene") straight or branched chain unsaturated aliphatic hydrocarbon groups having from 2 to 10 carbon atoms and having at least one triple bond. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, 1-heptynyl, 2-heptynyl, 1-octynyl, 2-octynyl, 1-nonyl, 1-decynyl, and the like.

The term "cycloalkyl" as used herein refers to cyclic saturated aliphatic groups and includes within its meaning monovalent ("cycloalkyl"), and divalent ("cycloalkylene"), saturated, monocyclic, bicyclic, polycyclic or fused polycyclic hydrocarbon radicals having from 3 to 10 carbon atoms, eg, 3, 4, 5, 6, 7, 8, 9, or 10 carbon atoms. Examples of cycloalkyl groups include but are not limited to cyclopropyl, 2-methylcyclopropyl, cyclobutyl, cyclopentyl, 2-methylcyclopentyl, 3-methylcyclopentyl, cyclohexyl, and the like, The term "cycloalkenyl" as used herein, refers to cyclic unsaturated aliphatic groups and includes within its meaning monovalent ("cycloalkenyl") and divalent ("cycloalkenylene"), monocyclic, bicyclic, polycyclic or fused polycyclic hydrocarbon radicals having from 3 to 10 carbon atoms and having at least one double bond, of either E, Z, cis or trans stereochemistry where applicable, anywhere in the alkyl chain. Examples of cycloalkenyl groups include but are not limited to cyclopropenyl, cyclopentenyl, cyclohexenyl, and the like.

The term "heterocycloalkyl" as used herein, includes within its meaning monovalent ("heterocycloalkyl") and divalent ("heterocycloalkylene"), saturated, monocyclic, bicyclic, polycyclic or fused hydrocarbon radicals having from 3 to 10 ring atoms wherein 1 to 5 ring atoms are heteroatoms selected from O, N, NH, or S. Examples include pyrrolidinyl, piperidinyl, quinuclidinyl, azetidinyl, morpholinyl, tetrahydrothiophenyl, tetrahydrofuranyl, tetrahydropyranyl, and the like.

The term "heterocycloalkenyl" as used herein, includes within its meaning monovalent ("heterocycloalkenyl") and divalent ("heterocycloalkenylene"), saturated, monocyclic, bicyclic, polycyclic or fused polycyclic hydrocarbon radicals having from 3 to 10 ring atoms and having at least 1 double bond, wherein from 1 to 5 ring atoms are heteroatoms selected from O, N, NH or S.

The term "heteroaromatic group" and variants such as "heteroaryl" or "heteroarylene" as used herein, includes within its meaning monovalent ("heteroaryl") and divalent ("heteroarylene"), single, polynuclear, conjugated and fused aromatic radicals having 6 to 20 atoms wherein 1 to 6 atoms are heteroatoms selected from O, N, NH and S. Examples of such groups include pyridyl, 2,2'-bipyridyl, phenanthrolinyl, quinolinyl, thiophenyl, and the like.

The term "halogen" or variants such as "halide" or "halo" as used herein refers to fluorine, chlorine, bromine and iodine.

The term "heteroatom" or variants such as "hetero-" as used herein refers to O, N, NH and S.

The term "alkoxy" as used herein refers to straight chain or branched alkyloxy groups. Examples include methoxy, ethoxy, n-propoxy, isopropoxy, tert-butoxy, and the like.

The term "amino" as used herein refers to groups of the form —$NR_aR_b$, wherein $R_a$ and $R_b$ are individually selected from the group including but not limited to hydrogen, optionally substituted alkyl, optionally substituted alkenyl, optionally substituted alkynyl, and optionally substituted aryl groups.

The term "aromatic group", or variants such as "aryl" or "arylene" as used herein refers to monovalent ("aryl") and divalent ("arylene") single, polynuclear, conjugated and fused residues of aromatic hydrocarbons having from 6 to 10 carbon atoms. Examples of such groups include phenyl, biphenyl, naphthyl, phenanthrenyl, and the like.

The term "aralkyl" as used herein, includes within its meaning monovalent ("aryl") and divalent ("arylene"), single, polynuclear, conjugated and fused aromatic hydrocarbon radicals attached to divalent, saturated, straight and branched chain alkylene radicals.

The term "heteroaralkyl" as used herein, includes within its meaning monovalent ("heteroaryl") and divalent ("heteroarylene"), single, polynuclear, conjugated and fused aromatic hydrocarbon radicals attached to divalent saturated, straight and branched chain alkylene radicals.

The term "optionally substituted" as used herein means the group to which this term refers may be unsubstituted, or may be substituted with one or more groups independently selected from alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocyclooxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, alkylheteroaryl, cyano, cyanate, isocyanate, —C(O)NH(alkyl), and —C(O)N(alkyl)$_2$.

The term "substantially non-polar" as used herein, refers to groups which do not contain more than one polar substituent capable of forming hydrogen bonds and which do not undergo protonation/deprotonation at physiological pH.

The term "antimicrobial" includes within its scope antifungal, antibacterial, antiviral and antiparasitic.

The term "antifungal" as used herein and unless stated to the contrary, includes within its scope fungistatic activity and fungicidal activity.

The term "antibacterial" as used herein and unless stated to the contrary, includes within its scope bacteriostatic activity and bacteriocidal activity.

The term "antiviral" as used herein and unless stated to the contrary, includes within its scope virostatic activity and virocidal activity.

The term "Phospholipase B" as used herein refers to protein(s) having one or more activities selected from phospholipase B (PLB) activity, lysophospholipase (LPL) activity and lysophospholipase transacylase (LPTA) activity. The protein(s) may or may not have other enzyme activities. This term encompasses cell associated (intracellular and membrane bound) and secretory Phospholipase B enzyme. Thus, in the context of this specification, the term "Phospholipase B" refers to a protein which may exhibit one or more of PLB, LPL or LPTA activity.

In the context of this invention the term "administering" and variations of that term including "administer" and "administration", includes contacting, applying, delivering or providing a compound or composition of the invention to an organism, or a surface by any appropriate means.

In the context of this specification, the term "vertebrate" includes humans and individuals of any species of social, economic or research importance including but not limited to members of the genus ovine, bovine, equine, porcine, feline, canine, primates (including human and non-human primates), rodents, murine, caprine, leporine, and avian.

In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the terms "therapeutically effective amount" and "diagnostically effective amount", include within their meaning a sufficient but non-toxic amount of a compound or composition of the invention to provide the desired therapeutic or diagnostic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

Abbreviations

"PLB"—Phospholipase B activity
"LPL"—lysophospholipase activity
"LPTA"—lysophospholipase transacylase activity
"MIC"—minimum inhibitory concentration
"EDTA"—ethylenediaminetetraacetic acid
"EGTA"—ethyleneglycoldiamine tetraacetic acid

BRIEF DESCRIPTION OF THE DRAWINGS

A preferred form of the present invention will now be described by way of example with reference to the accompanying drawings wherein.

DETAILED DESCRIPTION OF THE INVENTION

Figure 1A:
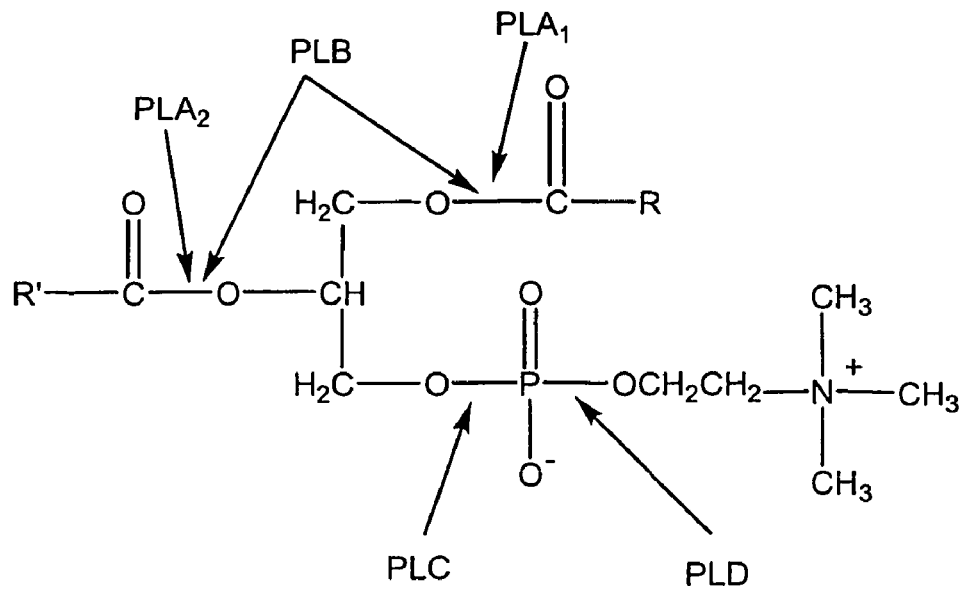
FIG. 1a. Sites of action of some phospholipases on (diacyl)phospholipids

The present invention relates to bis-cationic compounds, including bis-ammonium compounds, bis-phosphonium compounds and ammonium/phosphonium compounds, and their use as antimicrobial agents, e.g, antibacterial, antifungal, antiviral, antiparasitic and/or antiprotozoal agents. Bis-cationic compounds of Formula (I) and Formula (II) disclosed herein may display broad spectrum antimicrobial activity.

The bis-cationic compounds disclosed herein may be capable of inhibiting microbial phospholipase(s). However the present invention is not limited to bis-cationic compounds which are phospholipase inhibitors. Compounds which are capable of inhibiting intracellular phospholipases, e.g, cytosolic or membrane associated phospholipases may have antimicrobial properties. Inhibition of extracellular phospholipases may have fungistatic properties and/or bacteriostatic properties, and/or virostatic properties.

Bis-cationic compounds according to the present invention comprise two cationic head groups substituted with non-polar or substantially non-polar groups. The head groups are linked by a non-polar or substantially non-polar spacer group.

Compounds within the scope of the present invention include bis-cationic compounds of Formula (I) and Formula (II) as defined herein.

In Formula (I) and Formula (II) the cationic head groups "$Y_1(R_1R_2R_3)$" and "$Y_2(R_4R_5R_6)$" may be the same or different and are independently selected from a quaternary ammonium group and a quaternary phosphonium group. Thus, the cationic head groups may both be quaternary ammonium groups, one may be a quaternary ammonium group and the other a phosphonium group, or both may be phosphonium groups.

The $R_1$ to $R_6$ groups attached to the cationic quaternary N or P may be the same or different. In one embodiment of the invention, $R_1$ to $R_3$ are the same. In another embodiment, $R_4$ to $R_6$ are the same. In a further embodiment, $R_1$ to $R_6$ are the same.

The $R_1$ to $R_6$ groups attached to the cationic quaternary N and P atoms are generally non-polar or substantially non-polar. Thus, the $R_1$ to $R_6$ groups may not contain more than one polar group which could be involved in hydrogen bonding. Thus, for example, respective $R_1$ to $R_6$ groups may each be substituted with one hydroxyl group. In some embodiments, the $R_1$ to $R_6$ groups may not contain groups which can become protonated to form positive charges or which can become disassociated to form negative charges in a pH range of about 4 to about 9.

$R_1$ to $R_6$ may be the same or different and in one embodiment are independently selected from optionally substituted $C_{2-10}$ alkyl. In another embodiment, $R_1$ to $R_6$ are independently selected from optionally substituted $C_{2-8}$ alkyl. In a further embodiment, $R_1$ to $R_6$ are independently selected from optionally substituted $C_{3-6}$ alkyl.

In one embodiment of the invention, $Y_1$ and $Y_2$ are each N, and $R_1$ to $R_6$ are independently selected from $C_{2-10}$ alkyl.

Different groups attached to a respective cationic N or P may vary in length from each other, for example, by 2 to 6 carbons. For example, a cationic head group may comprise:

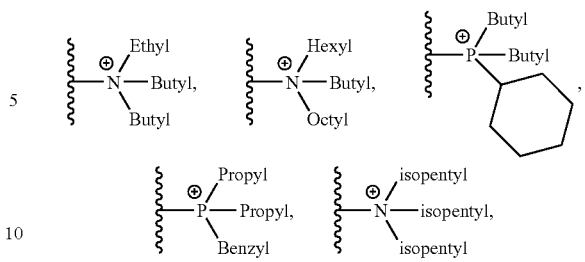

and the like.

The spacer group "$C(R_7R_{7'})$-A-$C(R_8R_{8'})$" is a non-polar or substantially non-polar residue and comprises an optionally substituted carbon backbone linking the polar cationic head groups. The spacer portion may be from 7 to 20 carbon atoms in length for Formula (I) compounds, or from 6 to 20 atoms in length for Formula II compounds. For example, the spacer may be 7, 8, 9, 10, 11, 12, 13, 14, 15, 16, 17, 18, 19 or 20 carbon atoms in length for compounds of Formula (I), or 6, 7, 8, 9, 10, 11, 12, 13, 14, 15, 16, 17, 18, 19 or 20 carbon atoms in length for compounds of Formula (II). In various embodiments of the invention, the spacer may be $C_{10-16}$, $C_{10-18}$ or $C_{10-20}$ carbon atoms in length, wherein respective carbon atoms may be optionally substituted. In alternative embodiments, the spacer may be from 6 to 11 or 7 to 11 carbon atoms in length.

The spacer group may comprise one or more optionally substituted groups selected from alkylene, alkenylene, alkynylene, cycloalkylene, arylene, and carbonyl groups. Examples of optional substituents include one or more groups selected from halides, alkyl, alkenyl, alkoxy, carboxylic acids, esters, ethers, thioethers, secondary or tertiary amines, secondary or tertiary amides, nitro, hydroxyl, thiol, amino acids, small peptides (eg, 2, 3, 4 or 5 amino acids in length), etc. The groups at respective terminal ends of the spacer group which are immediately adjacent the respective cationic groups (sometimes referred to herein as the "α" and "ω" carbons) may be independently selected from —$CH_2$—, —$CCl_2$—, —$CFCl$—, and —$CF_2$— groups.

Compounds of Formula (I) and Formula (II) may comprise one or more amino acids (as defined herein) or oligoamino acids (eg, 2, 3, 4, or 5 amino acids in length), attached to one or more carbons of the spacer group. In the context of this specification, "oligoamino acids" refers to amino acids linked through their respective amino and acid groups to form dipeptidyl, tripeptidyl, tetrapeptidyl, and pentapeptidyl residues. Compounds according to the invention may further optionally include one or more "depsi" (peptides), viz, peptides comprising an ester bond (eg, via a hydroxyl group in an amino acid or hydroxy acid such as glycollic acid, lactic acid, etc). α, β, or γ Amino acids may be used and (L) and (D) isomers may be used. Examples of amino acid substituents include glycinyl, alaninyl, valinyl, leucinyl, isoleucinyl, methioninyl, prolinyl, phenylalaninyl, tryptophanyl, serinyl, threoninyl, cysteinyl, tyrosinyl, asparaginyl, glutaminyl, aspartyl, glutamyl, lysinyl, argininyl and histidinyl. Other amino acids are known to those skilled in the art. The amino acid groups may be N- or C-linked to the spacer portion of the compound. The amino acid group may also be attached via the amino acid side chain, eg, a —COOH substituent of asparatic acid or glutamic acid, a —SH group of methionine or cysteine, etc.

In another embodiment of the invention the compound of Formula (I) is:

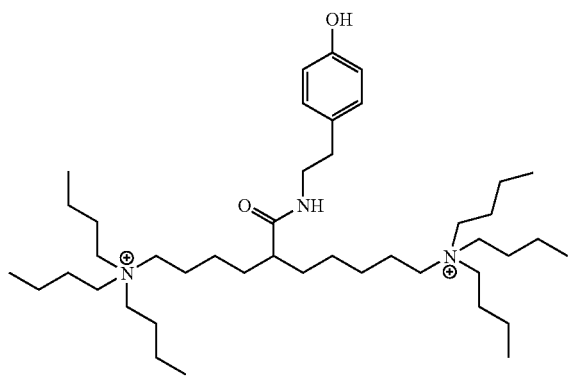

In a further embodiment of the invention the compound of Formula (I) is:

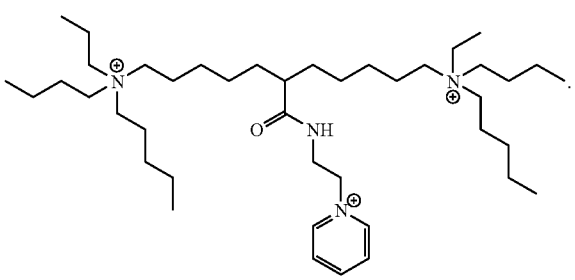

In another embodiment of the invention the compound of Formula (I) is:

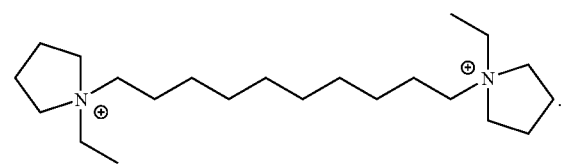

In a further embodiment of the invention the compound of Formula (I) is:

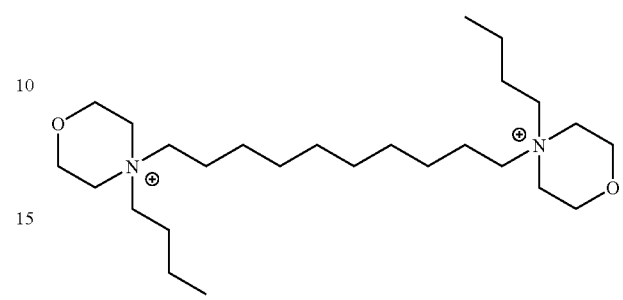

In another embodiment of the invention the compound of Formula (I) is:

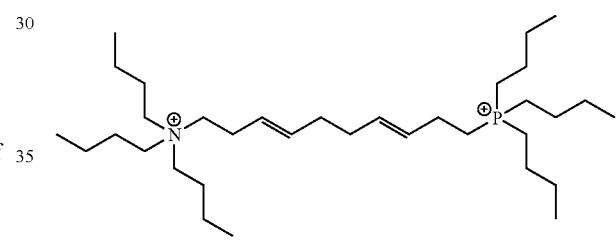

In a further embodiment of the invention the compound of Formula (I) is:

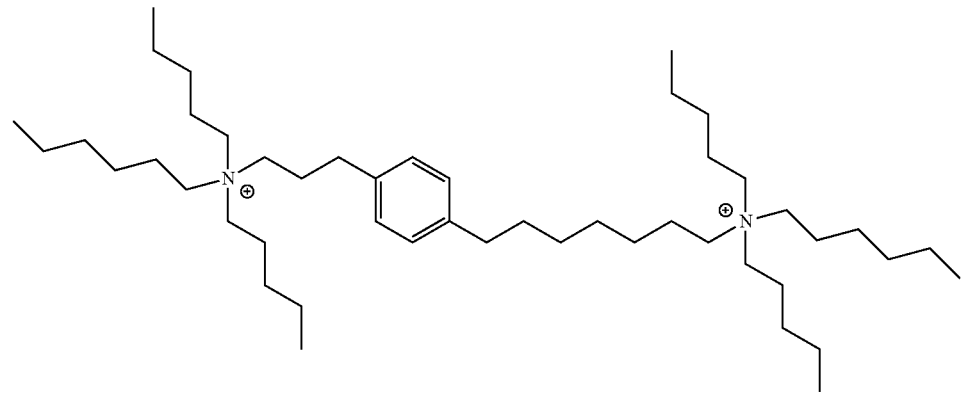

In another embodiment of the invention the compound of Formula (I) is:

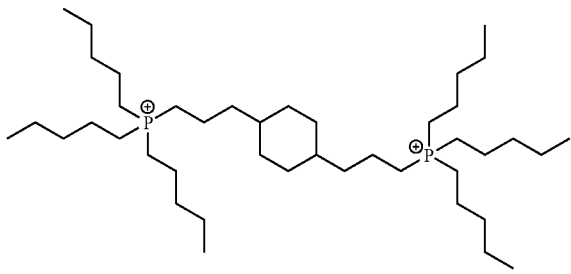

In a further embodiment of the invention the compound of Formula (I) is:

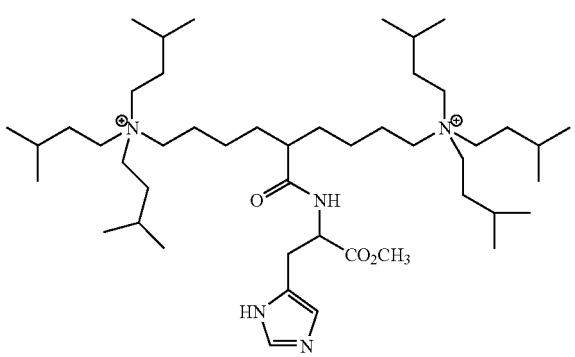

In other embodiments of the invention, the compound of Formula (I) is selected from:

1,11-bis-(tributylammonium)undecane, 1,16-bis-(tributylammonium)hexadecane, 1,12-bis-(tripentylammonium)dodecane, 1,12-bis-(trihexylammonium)dodecane, 1,12-bis-(trioctylammonium)dodecane, 1,12-bis-(triisobutylammonium)dodecane, 1,12-bis-(triisopentylammonium)dodecane, and 1,12-bis-(1-butylpyrrolidinium)dodecane, and salts thereof.

In one embodiment of the invention the compound of Formula (II) is:

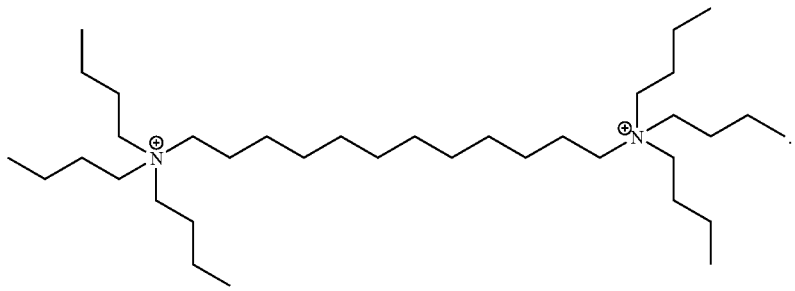

In another embodiment of the invention the compound of Formula (II) is:

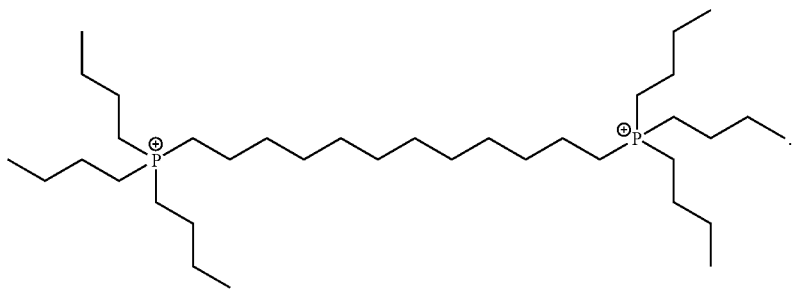

In another embodiment of the invention the compound of Formula (II) is:

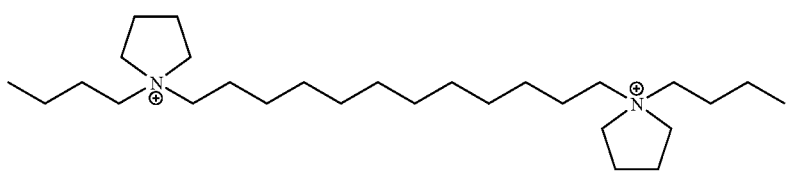

In a further embodiment of the invention the compound of Formula (II) is:

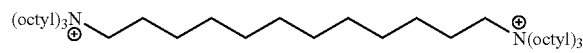

In another embodiment of the invention the compound of Formula (II) is:

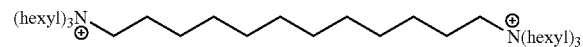

In a further embodiment of the invention the compound of Formula (II) is:

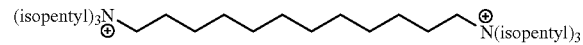

In another embodiment of the invention the compound of Formula (II) is:

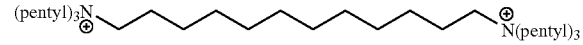

In another embodiment of the invention the compound of Formula (II) is:

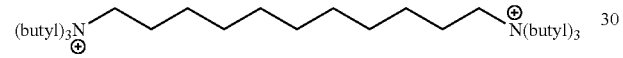

In a further embodiment of the invention the compound of Formula (II) is:

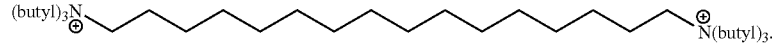

Bis-cationic compounds according to the present invention may inhibit Phospholipase B enzyme(s) in microorganisms, although the present invention is not limited only to compounds having that activity. Phospholipase B enzymes(s) are distinguished by having activity including one or more of phospholipase B (PLB) activity, lysophospholipase (LPL) activity and lysophospholipase transacylase (LPTA) activity. Phospholipase B may be cell associated (i.e., intracellular or membrane bound) enzyme(s), or secretory Phospholipase B enzyme(s). Thus, the class of enzymes is referred to as "Thospholipase B", and Phospholipase B enzymes may exhibit one or more activities, including phospholipase B (PLB) activity. Therefore, in the context of this specification "TLB" refers to the action of the enzyme; "Thospholipase B" refers to the class of enzyme. An overview of the characterisation and activity of Phospholipase B is provided by Wilton et al., in *Biochemistry of Lipids, Lipoproteins and Membranes* (4th Edition), D. E. Vance and J. E. Vance (Eds.) 2002, pp. 291-314.

Synthesis of Compounds

Compounds of Formula (I) and Formula (II) may be prepared by methods known to those skilled in the art. Suitable methods are generally described, for example, and intermediates thereof are described, for example, in Houben-Weyl, *Methoden der Organischen Chemie*; J. March, *Advanced Organic Chemistry*, 4th Edition (John Wiley & Sons, New York, 1992); D. C. Liotta and M. Volmer, eds, *Organic Syntheses Reaction Guide* (John Wiley & Sons, Inc., New York, 1991); R. C. Larock, *Comprehensive Organic Transformations* (VCH, New York, 1989), H. O. House, *Modern Synthetic Reactions* 2nd Edition (W. A. Benjamin, Inc., Menlo Park, 1972).

Those skilled in the art will also appreciate that various protecting groups may be used throughout a synthesis. Examples of protecting groups are known to those skilled in the art and have been described, for example, in Greene et al., *Protective Groups in Organic Synthesis*; John Wiley & Sons, 2nd Edition, 1991.

Those skilled in the art will also realise that bis-cationic compounds of Formula (I) and Formula (II) may be prepared as salts and may comprise one or more of any suitable counterion. The counterion may be anionic, dianionic or polyanionic. Where more than one counterion is present, the counterions may be the same or different. Examples of counterions include, but are not limited to halides (such as Cl$^-$, Bf$^-$, I$^-$), carboxylates, citrate, acetate, succinate, $CF_3CO_2^-$, tosylate, nitrate, $BF_4^-$, $PF_6^-$, and OH$^-$. The counterion(s) may be varied using techniques known to those skilled in the art, for example, ion exchange and crystallisation.

The present invention includes within its scope all isomeric forms of the compounds disclosed herein, including all diastereomeric isomers, racemates and enantiomers. Thus, formulae (I) and (II) should be understood to include, for example, E, Z, cis, trans, (R), (S), (L), (D), (+), and/or (−) forms of the compounds, as appropriate in each case.

Compounds of Formula (I) and Formula (II) may be prepared according to the following general Schemes (a)-(f):

Scheme (a)

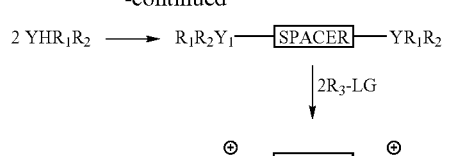

Scheme (b)

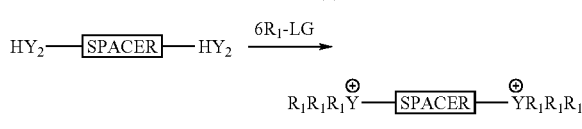

Scheme (c)

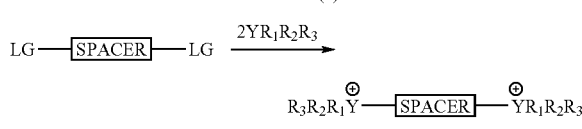

Scheme (d)

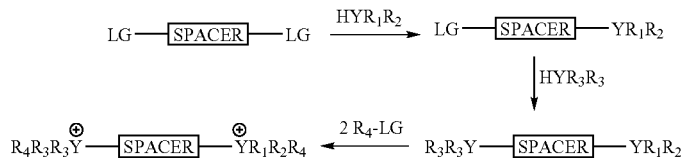

Scheme (e)

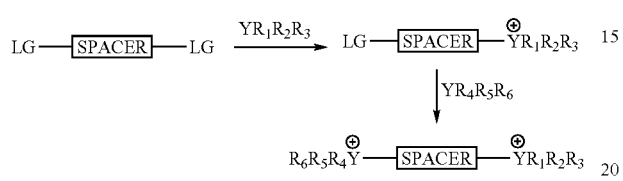

Scheme (f)

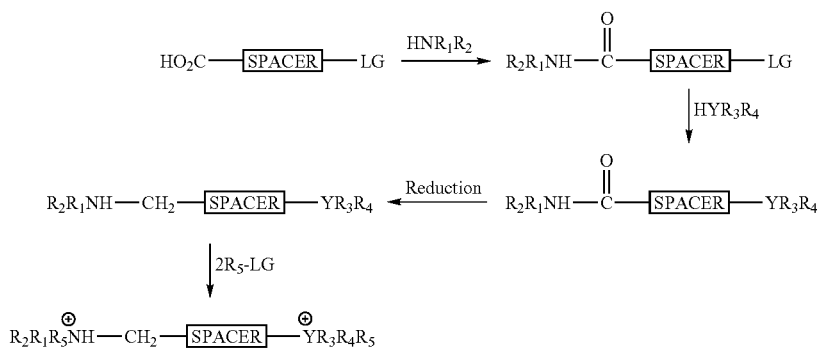

With reference to the above Schemes (a)-(f), "Y" represents N or P. "LG" represents a leaving group which can be displaced by a nucleophilic amine or phosphine. Examples of suitable leaving groups are known those skilled in the art and include, for example, chloro, bromo, iodo, mesylate, tosylate and triflate groups. The various leaving groups in the above Schemes (a)-(f) may be the same or different and may be varied as appropriate to modify the reactivity. Similarly, different leaving groups and nucleophiles (e.g, HYNRR) may be employed at different stages of the synthesis. In the above Schemes, the groups $R_1$, $R_2$, $R_3$, $R_4$, $R_5$ and $R_6$ represent non-polar or substantially non-polar groups as defined above for Formula (I) and Formula (II), for example, alkyl groups, cycloalkyl groups, alkenyl groups, aralkyl groups such as benzyl, heteroaryl groups, heteroalkyl groups, etc. Respective $R_1$, $R_2$, $R_3$, $R_4$, $R_5$ and $R_6$ groups may be the same or different and each may be optionally substituted, e.g, with one or more groups selected from $C_{1-6}$ alkyl, $C_{2-6}$ alkenyl, $C_{2-6}$ alkynyl, hydroxyl, halides, $O(C_{1-6}$ alkyl), $C(O)O(C_{1-6}$ alkyl), $NO_2$, amino, hydroxy$C_{1-6}$ alkyl, aryl, $OC(O)Ph$, or $=C(Ph)_2$.

Scheme (a) illustrates a synthetic route for a symmetrical bis-cationic compound. However, those skilled in the art will realise that by varying the stoichiometric ratios and reaction conditions, or by varying the $R_1$, $R_2$, and $R_3$, groups, asymmetric compounds may also be prepared according to the above route.

With reference to Scheme (f), suitable reducing agents are known to those skilled in the art and include, for example, $H_2$, Pd/C, LiALH4, $NaBH_4$, Zn/HCl, Sn/HCl, etc.

With reference to Schemes (a)-(f) above, suitable reagents, reaction conditions etc, will be known to those skilled. By way of example, suitable solvents may include relatively polar solvents, such as acetonitrile, ethanol, ethers, methylisobutyl alcohol, methylisobutyl ketone, and the like. The reaction temperature(s) may be adjusted as appropriate to control the rate of reaction. By way of example, suitable reaction temperatures may be above room temperature, eg, greater than 50° C.

The bis-cationic compounds of the invention may be prepared as salts. The counterions may be varied using methods known to those skilled in the art, including for example, ion exchange columns and crystallization techniques.

Compounds according to the present invention may be useful for the treatment, inhibition or prevention of microbial infection, such as fungal, bacterial, viral and protozoal infection. Thus, compounds according to the present invention may have therapeutic applications, including pharmaceutical and veterinary applications. The compounds according to the present invention may also have industrial applications and for example, may be useful as disinfectants. Compounds according to the present invention may also have agricultural applications and for example, may be used to treat, inhibit or prevent microbial infection of plants and crops. The compounds may be formulated as composition in an appropriate manner for the intended use.

Thus, the present invention also relates to the use of at least one compound of Formula (I) or Formula (II) defined herein for the manufacture of a medicament for one or more of treating, inhibiting and preventing a microbial infection.

The microbial infection may be on a surface, such as the surface of an article, e.g, a surgical article or device, a floor, benchtop, or industrial work surface. The microbial infection may be an infection of a vertebrate, e.g, a systemic infection, or an infection on the surface of the skin of a vertebrate.

The microbial infection may comprise one or more of bacteria, fungi, viruses, and parasites.

The present invention also relates to a method for one or more of treating, inhibiting, and preventing a microbial infection in a vertebrate, said method comprising administering to said vertebrate an effective amount of at least one compound of Formula (I) or Formula (II) defined herein.

The present invention also relates to a method of treating, inhibiting, and preventing a microbial infection of a plant, said method comprising contacting said plant with an effective amount of at least one compound of Formula (I) or Formula (II) defined herein.

A compound of Formula (I) or Formula (II) may be contacted with any part of a plant, including leaves, fruit, flowers, stem, tuber, or root. The plant may be an agriculturally or horticulturally important plant. In one embodiment, the infection is a fungal infection.

The present invention also relates to an antimicrobial composition comprising at least one compound of Formula (I) or a compound of Formula (II) defined herein, together with an industrially, veterinarially, agriculturally, or pharmaceutically suitable carrier, diluent or carrier.

The composition may be one or more of an antifungal, antibacterial, antiviral and antiparasitic composition. In one embodiment the composition is an antifungal composition. In another embodiment the composition is an antibacterial composition.

The present invention also relates to a pharmaceutical composition comprising at least one compound of Formula (I) or Formula (II) together with a pharmaceutically effective carrier, adjuvant or diluent.

The present invention also relates to a method of inhibiting phospholipase in an organism comprising contacting said organism with an effective amount of at least one compound of Formula (I) or at least one compound of Formula (II), or a composition thereof.

The organism may be a microbial organism such as bacteria, fungi, virus, or a parasite, including for example protozoa. The phospholipase may be Phospholipase B.

The present invention also relates to a method for identifying an antimicrobial agent comprising contacting microbial cells with a compound suspected of having antimicrobial properties, determining whether the compound inhibits a microbial phospholipase enzyme, wherein inhibition of said phospholipase enzyme indicates antimicrobial activity, and thereby identifying an antimicrobial agent. The compound may be a compound of Formula (I) or Formula (II) as defined herein. The phospholipase may be Phospholipase B.

In one embodiment of the invention, when used for the treatment, prevention or inhibition of a fungal infection, the compound is not a compound of Formula (I) or Formula (II) wherein $Y_1$ and $Y_2$ are each N; $R_7$, $R_{7'}$, $R_8$, $R_{8'}$ are each hydrogen; A is unsubstituted $C_{8-10}$ alkylene; and $R_1$ to $R_6$ are each methyl or $R_1$ to $R_6$ are each isobutyl.

In another embodiment of the invention, when used for the treatment, prevention or inhibition of a parasitic infection selected from malaria and babesiosis, the compound is not a compound of Formula (I) or Formula (II) wherein $Y_1$ and $Y_2$ are each N; $R_7$, $R_{7'}$, $R_8$, $R_{8'}$ are each hydrogen; A is $C_{10-18}$ alkylene substituted with a $C_{1-3}$ alkyl group; and $R_1$ to $R_6$ are independently $C_{1-10}$ alkyl.

In a further embodiment of the invention, when used for the treatment, prevention or inhibition of a parasitic infection selected from malaria and babesiosis the compound is not a compound of Formula (I) or Formula (II) wherein $Y_1$ and $Y_2$ are each N; $R_3$ and $R_6$ are each $C_{1-10}$ alkyl; $R_1$ and $R_2$ together with the N to which they are attached, and $R_4$ and $R_5$ together with the N to which they are attached are each a 5-membered heterocycloalkyl ring comprising one S or O, substituted with hydroxy$C_{1-3}$ alkyl or halo$C_{1-3}$ alkyl; $R_7$, $R_{7'}$, $R_8$, and $R_{8'}$ are each hydrogen, and A is $C_{10-18}$ alkylene substituted with a $C_{1-3}$ alkyl substituent.

In another embodiment of the invention, when used for the treatment, prevention or inhibition of a fungal infection, the compound is not a compound of Formula (I) or Formula (II) wherein $Y_1$ and $R_1$ to $R_3$ together are quinuclidine; $Y_2$ and 4 to $R_6$ together are quinuclidine; $R_7$, $R_{7'}$, $R_8$, $R_{8'}$ are each hydrogen; and A is unsubstituted $C_{8-10}$ alkylene.

Types and classes of microbes are known in the art. Classes of microbes are listed, for example, in *Manual of Clinical Microbiology*, 7$^{th}$ Edition, 1999, American Society of Microbiology, the entire contents of which are incorporated herein by reference. Some general examples of microorganisms include the following, however it is to be understood that the scope of the invention is by known means limited to these microorganisms:

Bacteria including: Gram positive cocci, such as *Staphylococcus* spp., *Staphylococcus* spp., *Streptococcus* spp., *Enterococcus* spp.; gram positive rods, such as Coryneform, *Listeria* spp., *Erysipelothrix* spp., and *Kurthia* spp., *Bacillus* spp., *Mycobacterium* spp.; Gram negative bacteria, such as *Enterobacteriaceae* sp., *Escherichia* spp., *Shigella* spp., *Salmonella* spp., *Klebsiella* spp., *Enterobacter* spp., *Citrobacter* spp., *Serratia* spp., *Aeromonas* spp. and *Plesiomonas* spp., *Pseudomonas* spp.; *Acinetobacter* spp., *Alcaligenes* spp., *Moraxella* spp. and *Methylobacterium* spp; *Actinobacillus* spp., *Capnocytophaga* spp., *Eikenella* spp., *Kiitgella* spp., such as *Legionella* spp., *Neisseria* spp., *Branhamella* spp.; anaerobic bacteria, including *Clostridium* spp., *Peptostreptococcus* spp., *Propionibacterium* spp., *Lactobacillus* spp., *Actinomyces* spp.; *Bacteroides* spp., *Porphyromonas* spp., *Prevotella* spp., *Fusobacterium* spp., and other anaerobic gram negative cocci; curved and spiral-shaped gram negative rods, including *Helicobacter* spp., *Borrelia* spp.; Mycoplasmas and obligate intracellular bacteria, such as *Mycoplasma* spp., *Ureaplasma* spp., *Chlamydia* spp., *Coxiella* spp.;

Viruses including Human Immunodeficiency viruses (HIV), Human T-Cell Lymphotropic Virus Types I and II, Herpes Simplex Viruses, Human cytomegalovirus, Varicella-Zoster Virus, Hurman Herpesviruses 6, 7 and 8 and Herpes B virus, Measles Virus, Mumps virus, Adenoviruses, Rhinoviruses, Rotaviruses, Hepatitis B and D viruses, Hepatitius C and G viruses, Human papillomavirus;

Fungi include *Candida* spp., *Cryptococcus* spp. and medically important yeasts, *Pneumocystis carini* spp., *Aspergillus* spp., *Fusarium* spp. and other Moniliaceous fungi, *Rhizopus* spp., *Rhizomucor* spp., *Absidia* spp. and other agents of systemic and subcutaneous Zygomycoses, *Trichophyton* spp., *Microsporum* spp., *Epidennophyton* spp., *Bipolaris* spp., *Exophiala* spp., *Scedosporium* spp., *Sporothrix* spp. and other dematiaceous fungi, fungi causing Eumycotic Mycetoma; Collectitrichum coccodes, fungi causing powdery mildew, downy mildew, botrytis, black dot and black scurf (Rhizoctonia) in plants;

Parasites including *Plasmodium* spp., *Babesia* spp., *Leishinania* spp., *Trypanosoma* spp., *Toxoplasma giardia* spp., pathogenic and opportunistic free-living Amebae, intestinal and urogenital Amebae, Flagellates and Ciliates; Cryptosporidium, Cyclospora, Isospora, Microsporidia, and intestinal Helminths.

Formulations

In accordance with the present invention, when used for the treatment or prevention of microbial infection, compound(s) of the invention may be administered alone. Alternatively, the compounds may be administered as a pharmaceutical, veterinarial, agricultural, or industrial formulation which comprises at least one compound according to the invention. The compound(s) may also be present as suitable salts, including pharmaceutically acceptable salts.

In accordance with the present invention, the compounds of the invention may be used in combination with other known treatments or antimicrobial agents, including antifungal treatments, antibiotics, disinfectants, etc. Suitable agents are listed, for example, in the Merck Index, *An Encyclopedia of Chemicals, Drugs and Biologicals,* 12$^{th}$ Ed., 1996, the entire contents of which are incorporated herein by reference.

Combinations of active agents, including compounds of the invention, may be synergistic.

By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

For instance, suitable pharmaceutically acceptable salts of compounds according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present invention therefore include acid addition salts.

S. M. Berge et al. describe pharmaceutically acceptable salts in detail in *J. Pharmaceutical Sciences,* 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Convenient modes of administration include injection (subcutaneous, intravenous, etc.), oral administration, inhalation, transdermal application, topical creams or gels or powders, or rectal administration. Depending on the route of administration, the formulation and/or compound may be coated with a material to protect the compound from the action of enzymes, acids and other natural conditions which may inactivate the therapeutic activity of the compound. The compound may also be administered parenterally or intraperitoneally.

Dispersions of the compounds according to the invention may also be prepared in glycerol, liquid polyethylene glycols, and mixtures thereof and in oils. Under ordinary conditions of storage and use, pharmaceutical preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

In one embodiment of the invention, the compound(s) of the invention may be administered orally, for example, with an inert diluent or an assimilable edible carrier. The compound(s) and other ingredients may also be enclosed in a hard or soft shell gelatin capsule, compressed into tablets, or incorporated directly into an individual's diet. For oral therapeutic administration, the compound(s) may be incorporated with excipients and used in the form of ingestible tablets, buccal tablets, troches, capsules, elixirs, suspensions, syrups, wafers, and the like. Suitably, such compositions and preparations may contain at least 1% by weight of active compound. The percentage of the compound(s) of formula (I) and/or (II) in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage will be obtained.

The language "pharmaceutically acceptable carrier" is intended to include solvents, dispersion media, coatings, antibacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage. "Dosage unit form" as used herein refers to physically discrete units suited as unitary dosages for the individual to be treated; each unit containing a predetermined quantity of compound(s) is calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In one embodiment, the carrier may be an orally administrable carrier.

Another form of a pharmaceutical composition is a dosage form formulated as enterically coated granules, tablets or capsules suitable for oral administration.

Also included in the scope of this invention are delayed release formulations.

Compounds of the invention may also be administered in the form of a "prodrug". A prodrug is an inactive form of a compound which is transformed in vivo to the active form. Suitable prodrugs include esters, phosphonate esters etc, of the active form of the compound.

In one embodiment, the compound may be administered by injection. In the case of injectable solutions, the carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the analogue can be incorporated into sustained-release preparations and formulations.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the pharmaceutical compositions according to the invention may be carried out. One skilled in the art would be able, by routine experimentation, to determine effective, non-toxic dosage levels of the compound and/or composition of the invention and an administration pattern which would be suitable for treating the diseases and/or infections to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m$^2$. For example, generally, an effective dosage is expected to be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, and about 75 to about 150 mg/m$^2$.

EXAMPLES

The invention will now be described in more detail, by way of illustration only, with respect to the following examples. The examples are intended to serve to illustrate this invention and should not be construed as limiting the generality of the disclosure of the description throughout this specification.

Example 1

Synthesis and Characterisation of Bis-Cationic Compounds 1,12-Bis-(quinuclidinium)dodecane dibromide To 1,12-dibromododecane (0.50 g, 1.52 mmol) in methyl isobutyl ketone (1 ml) was added quinuclidine (0.34 g, 3.0 mmol). The mixture was deoxygenated by freeze/thaw and stirred at reflux for 24 h, at which time precipitate was formed. The crude mixture was cooled, the precipitate filtered off to yield the desired compound as a white solid (0.45 g, 54%). $^1$H NMR (200 MHz, CDCl$_3$): δ 3.77-3.73 (12H, m,), 3.57-3.48 (4H, m), 2.31-2.28 (2H, m), 2.22-2.17 (12H, m), 1.78-1.74 (4H, m), 1.37-1.15 (18H, m). $^{13}$C NMR (300 MHz, CDCl$_3$): δ 55.2, 28.7, 28.6, 28.4, 24.4, 24.3, 22.7, 2 signals obscured or overlapping; m/z 195 [M−2Br$^-$]$^{2+}$ (100%), 470 [M−Br$^-$]$^+$ (75). Found [M−2Br$^-$]$^{2+}$ 195.1979, [C$_{26}$H$_{50}$N$_2$]$^{2+}$ requires 195.1982.

1,12-Bis-(1-methylmorpholinium)dodecane dibromide 1,12-Dibromododecane (0.50 g, 1.52 mmol) was dissolved in N-methylmorpholine (0.61 g, 6.08 mmol). The mixture was deoxygenated by freeze/thaw and stirred at 80° C. for 24 h to yield the desired compound as a white hygroscopic solid which was collected by filtration and washed with dry diethyl ether (0.52 g, 65%). $^1$H NMR (200 MHz, MeOD): δ 4.10-4.09 (8H, m), 3.68-3.46 (12H, m), 3.36 (6H, s, 2×CH$_3$), 2.08-2.05 (4H, br.s), 1.44-1.35 (18H, m). $^{13}$C NMR (300 MHz, MeOD): δ 70.1, 65.0, 64.2, 51.9, 33.6, 33.3, 30.1, 25.9, 1 signal obscured or overlapping; m/z 185 [M−2Br$^-$]$^{2+}$ (100%).

1,11-Bis-(tributylammonium)undecane dichloride 1,11-Dibromoundecane (0.10 g, 0.32 mmol) was dissolved in tributylamine (0.24 g, 1.27 mmol). The resulting mixture was deoxygenated by freeze/thaw and was stirred at 130° C. for 20 h. The solvent was removed under reduced pressure and the crude mixture was purified by flash chromatography (90:10:1 $CH_2Cl_2$/MeOHt $NH_3$(aq)). The combined fractions were then passed a down a column of Lewatit MP-64 anion resin (Cr). The resulting fractions were combined and the solvent removed under reduced pressure to give the above compound as a light brown oil (0.13 g, 69%). $^1$H NMR (200 MHz, $CDCl_3$): δ 3.52-3.02 (12H, m), 2.92-2.89 (4H, m), 1.68-1.58 (16H, m), 1.40-1.26 (26H, m), 0.95-0.86 (18H, m, 6×$CH_3$). $^{13}$C (300 MHz, $CDCl_3$): 60.0, 54.6, 30.7, 27.8, 27.3, 21.3, 14.4, 3 signals obscured or overlapping.

1,12-Bis-(tributylammonium)dodecane dichloride 1,12-Dibromododecane (1.0 g, 3.05 mmol) was dissolved in methyl isobutyl ketone (5 ml). Tributylamine (1.13 g, 6.09 mmol) was added and the resulting mixture was deoxygenated by freeze/thaw. The mixture was stirred at reflux for 24 h and the solvent was removed under reduced pressure. The crude mixture was purified by flash chromatography (90:10:1 $CH_2Cl_2$/MeOH/$NH_3$(aq)). The combined fractions were then passed a down a column of Lewatit MP-64 anion resin (Cl$^-$). The resulting fractions were combined and the solvent removed under reduced pressure to give the above compound as a yellow oil (0.5 g, 27%). $^1$H NMR (200 MHz, $CDCl_3$): δ 3.37-3.29 (12H, m), 3.02-2.94 (4H, m), 1.78-1.65 (16H, m), 1.32-1.23 (28H, m), 0.89-0.82 (18H, m, 6×$CH_3$). $^{13}$C (300 MHz, $CDCl_3$): 59.6, 31.6, 26.5, 22.8, 22.7, 14.3, 4 signals obscured or overlapping; m/z ESI (positive ion) Found [M−Cl$^-$]$^+$ 573.5865, [$C_{36}H_{78}N_2Cl$]$^+$ requires 573.5852.

1,12-Bis-(tributylammonium)dodecane dibromide

To 1,12-diaminododecane (0.25 g, 1.25 mmol) in absolute ethanol (5 ml) was added butyl bromide (3.08 g, 22.5 mmol) and $K_2CO_3$ (1.04 g, 7.49 mmol). The mixture was stirred at reflux for 3 days to yield the desired compound as a yellow oil (0.76 g, 87%) which had identical $^1$H and $^{13}$C spectroscopical data to those described above; m/z ESI (positive ion) 270 [M−2Br$^-$]$^{2+}$ (100%), 619 [M−Br$^-$]$^+$ (70).

1,16-Bis-(tributylammonium)dodecane dichloride 1,16-Dibromohexadecane (0.15 g, 0.39 mmol) was dissolved in tributylamine (0.14 g, 0.78 mmol). The resulting mixture was deoxygenated by freeze/thaw and was stirred at 130° C. for 3 days. The crude mixture was purified by flash chromatography (80:18:2 $CH_2Cl_2$/MeOH/$NH_3$(aq)). The combined fractions were then passed a down a column of Lewatit MP-64 anion resin (Cl$^-$). The resulting fractions were combined and the solvent removed under reduced pressure to give the above compound as a brown oil (0.13 g, 48%). $^1$H NMR (200 MHz, $CDCl_3$): δ 3.37-3.29 (4H, m), 3.02-2.94 (12H, m), 1.78-1.65 (16H, m), 1.32-1.23 (26H, m), 0.89-0.82 (18H, m, 6×$CH_3$). $^{13}$C (300 MHz, $CDCl_3$): 59.6, 31.6, 26.5, 22.8, 22.7, 14.3, 6 signals obscured or overlapping; m/z ESI (positive ion) 297 [M−2Cl$^-$]$^{2+}$ (27%). Found [M−2Cl$^-$]$^{2+}$ 297.3397, [$C_{40}H_{86}N_2$]$^{2+}$ requires 297.3396.

1,12-Bis-(tripentylammonium)dodecane dibromide

To 1,12-dibromododecane (0.50 g, 1.52 mmol) was added triisobutylamine (1.38 g, 6.08 mmol) was added and the resulting mixture was deoxygenated by freeze/thaw. The mixture was stirred at reflux for 3 days. The crude product was washed with ether to yield the above compound as a brown oil (0.95 g, 80%). $^1$H NMR (200 MHz, $CDCl_3$): δ 3.29-3.27 (12H, m), 2.96-2.83 (4H, m), 1.67-1.61 (16H, m), 1.30-1.19 (40H, m), 0.84-0.79 (18H, m, 6×$CH_3$). $^{13}$C (300 MHz, $CDCl_3$): δ 59.5, 52.9, 29.3, 29.2, 26.7, 26.1, 22.5, 14.1, 3 signals obscured or overlapping; m/z ESI (positive ion) 311 [M−2Br$^-$]$^{2+}$ (100%), 703 [M−Br$^-$] (76). Found [M−2Br$^-$]$^{2+}$ 311.3541, [$C_{42}H_{90}N_2$]$^{2+}$ requires 311.3547.

1,12-Bis-(trihexylammonium)dodecane dichloride 1,12-Dibromododecane (0.50 g, 1.52 mmol) was dissolved in methyl isobutyl ketone (5 ml). Trihexylamine (0.82 g, 3.05 mmol) was added and the resulting mixture was deoxygenated by freeze/thaw. The mixture was stirred at reflux for 4 days and the solvent was removed under reduced pressure. The crude mixture was purified by flash chromatography (90:10:1 $CH_2Cl_2$/MeOH/$NH_3$(aq)). The combined fractions were then passed a down a column of Lewatit MP-64 anion resin (Cl$^-$). The resulting fractions were combined and the solvent removed under reduced pressure to give the above compound as a yellow oil (0.14 g, 12%). $^1$H NMR (200 MHz, $CDCl_3$): δ 3.37-3.29 (12H, m), 3.02-2.94 (4H, m), 1.78-1.65 (16H, m), 1.32-1.23 (52H, m,), 0.89-0.82 (18H, m, 6×$CH_3$). $^{13}$C (300 Mz, $CDCl_3$): δ 59.6, 31.6, 26.5, 22.8, 22.7, 14.3, 6 signals obscured or overlapping; m/z ESI (positive ion) 354 [M−2Cl$^-$]$^{2+}$ (100%).

1,12-Bis-(trioctylammonium)dodecane dichloride 1,12 Dibromododecane (0.52 g, 1.52 mmol) was dissolved in methyl isobutyl ketone (5 ml). Trioctylamine (1.12 g, 3.17 mmol) was added and the resulting mixture was deoxygenated by freeze/thaw. The mixture was stirred at reflux for 7 days and the solvent was removed under reduced pressure. The crude mixture was purified by flash chromatography (90:30:1 $CH_2Cl_2$/MeOH/$NH_{3(aq)}$). The combined fractions were then passed a down a column of Lewatit MP-64 anion resin (Cl$^-$). The resulting fractions were combined and the solvent removed under reduced pressure to give the above compound as a yellow oil (0.11 g, 7%). $^1$H NMR (200 MHz, $CDCl_3$): δ 3.37-3.29 (12H, m), 3.02-2.94 (4H, m), 1.78-1.65 (16H, m), 1.32-1.23 (76H, m), 0.89-0.82 (18H, m, 6×$CH_3$). $^{13}$C (300 MHz, $CDCl_3$): 59.6, 31.6, 26.5, 22.8, 22.7, 14.3, 8 signals obscured or overlapping; m/z ESI (positive ion) 909 [M−Cl$^-$]$^+$ (100%).

1,12-Bis-(triisobutylammonium)dodecane dibromide

To 1,12-Dibromododecane (0.50 g, 1.52 mmol) was added triisobutylamine (1.2 g, 6.10 mmol) and the resulting mixture was deoxygenated by freeze/thaw. The mixture was stirred at reflux for 48 h. The mixture was cooled and the above compound was obtained as a white precipitate (0.014 g, 2%). $^1$H NMR (200 MHz, $CDCl_3$): δ 3.40 (4H, dd), 1.89-1.78 (12H, m), 1.74-1.63 (6H, m), 1.45-1.28 (20H, m), 0.95-0.85 (36H, m, 12×$CH_3$); )m/z ESI (positive ion) 618 [M−Br$^-$]$^+$ (27).

1,12-Bis-(triisopentylammonium)dodecane dichloride 1,12-Dibromododecane (0.56 g, 1.71 mmol) was dissolved in methyl isobutyl ketone (5 ml). Triisopentylamine (0.78 g, 3.42 mmol) was added and the resulting mixture was deoxygenated by freeze/thaw. The mixture was stirred at reflux for 48 h and the solvent was removed under reduced pressure. The crude mixture was purified by flash chromatography (90:10:1 $CH_2Cl_2$/MeOH/$NH_3$(aq)). The combined fractions were then passed a down a column of Lewatit MP-64 anion resin (Cl$^-$). The resulting fractions were combined and the solvent removed under reduced pressure to give the above compound as a pale yellow oil (0.37 g, 31%). $^1$H NMR (200 MHz, $CDCl_3$): δ 3.20-3.12 (12H, m), 2.87-2.82 (4H, m), 1.58-1.35 (10H, m), 1.26-1.04 (28H, m), 0.79-0.71 (36H, m, 12×$CH_3$). $^{13}$C (300 MHz, $CDCl_3$): 59.0, 57.7, 52.8, 51.1, 31.7, 30.6, 29.1, 26.6, 22.5, 1 signal obscured or overlapping; m/z ESI (positive ion, before ion exchange) 703 [M−Br$^-$]$^+$ (45).

1,12-Bis-(tripropylammonium)dodecane dibromide 1,12-Dibromododecane (0.50 g, 1.52 mmol) was dissolved in tripropylamine (1.72 g, 12.1 mmol). The resulting mixture was deoxygenated by freeze/thaw and stirred at 80° C. for 48 h. The solvent was removed under reduced pressure and the resulting oil was triturated with ether to give the above compound as dark brown oil (0.70 g, 75%) $^1$H NMR (200 MHz, CDCl$_3$): δ 3.55-3.29 (12H, m), 3.00-2.96 (4H, m), 1.41 (16H, br. s.), 1.45-1.12 (16H, m), 0.99-0.90 (18H, m). $^{13}$C NMR (200 MHz, CDCl$_3$): δ 61.1, 54.6, 29.4, 23.7, 16.3, 11.3; m/z ESI (positive ion) 227 [M–2Br$^-$]$^{2+}$ (100).

1,12-Bis-(triethylammonium)dodecane dibromide 1,12-Dibromododecane (0.50 g, 1.52 mmol) was dissolved in triethylamine (0.92 g, 9.12 mmol). The resulting mixture was deoxygenated by freeze/thaw and stirred at 80° C. for 24 h. The solvent was removed under reduced pressure and the resulting oil was triturated with ether to give the above compound as a hygroscopic white solid (0.65 g, 81%).

1,12-Bis-(trimethylammonium)dodecane dibromide

Sodium hydroxide (0.25 g, 6.1 mmol) was added to a solution of trimethylamine hydrochloride in dry methanol (10 ml). The mixture was filtered and 1,12-dibromododecane (0.50 g, 1.52 mmol) was added to the filtrate. The mixture was refluxed for 12 h and the solvent removed under reduced pressure. The crude product was recrystallised from methanol/ether to yield the above compound as a white solid (0.64 g, 94%). Data same as *J. Med. Chem.*, 1997, 40, 3557-3566

1,12-Bis-(1-methylpyrrolidinium)dodecane dibromide 1,12-Dibromododecane (0.50 g, 1.52 mmol) was dissolved in 1-methylpyrrolidine (0.52 g, 6.08 mmol). The resulting mixture was deoxygenated by freeze/thaw and was stirred at 80° C. for 20 h. The solvent was removed under reduced pressure to yield the above compound as a white hygroscopic solid (0.49 g, 64%). $^1$H NMR (200 MHz, CDCl$_3$): □ 3.83-3.63 (12H, m), 3.28 (6H, s, 2×CH$_3$), 2.32-2.21 (8H, m), 1.85-1.82 (4H, m), 1.27-1.26 (16H, m).

1,12-Bis-(pyrrolidinium)dodecane 1,12 Dibromododecane (0.5 g, 1.52 mmol) was dissolved in pyrrolidine (0.44 g, 6.08 mmol). The mixture was stirred at 90° C. for 20 h. The crude mixture was purified by flash chromatography, eluting with 80:18:2 CH$_2$Cl$_2$/MeOH/NH$_3$ $_{(aq)}$ to yield the above compound as a yellow solid (0.33 g, 71%). $^1$H NMR (200 MHz, CDCl$_3$): δ 2.51-2.36 (12H, m), 1.80-1.74 (8H, m), 1.53-1.47 (4H, m), 1.27-1.26 (16H, m); m/z ESI (positive ion) 310 [M+H]$^+$ (100).

1,12-Bis-(N-butylpyrrolidinium)dodecane dibromide

To 1,12-bis-(pyrrolidinium)dodecane (0.33 g, 1.08 mmol) in methyl isobutyl ketone (2 ml) was added butyl bromide (0.88 g, 6.46 mmol). The resulting mixture was stirred at reflux for 20 h. The crude mixture was purified by flash chromatography, eluting with 80:18:2 CH$_2$Cl$_2$/MeOH/NH$_3$ $_{(aq)}$ to yield the above compound as a pale yellow oil (0.45 g, 71%). $^1$H NMR (200 MHz, CDCl$_3$): δ 3.42-3.31 (16H, m), 1.80-1.74 (4H, m), 1.45-1.20 (32H, m,), 0.86 (6H, t, 2×CH$_3$); 7m/z ESI (positive ion) 211 [M–2Br$^-$]$^{2+}$ (100).

Example 2

Characterisation of Enzyme Activity

Figure 1B:
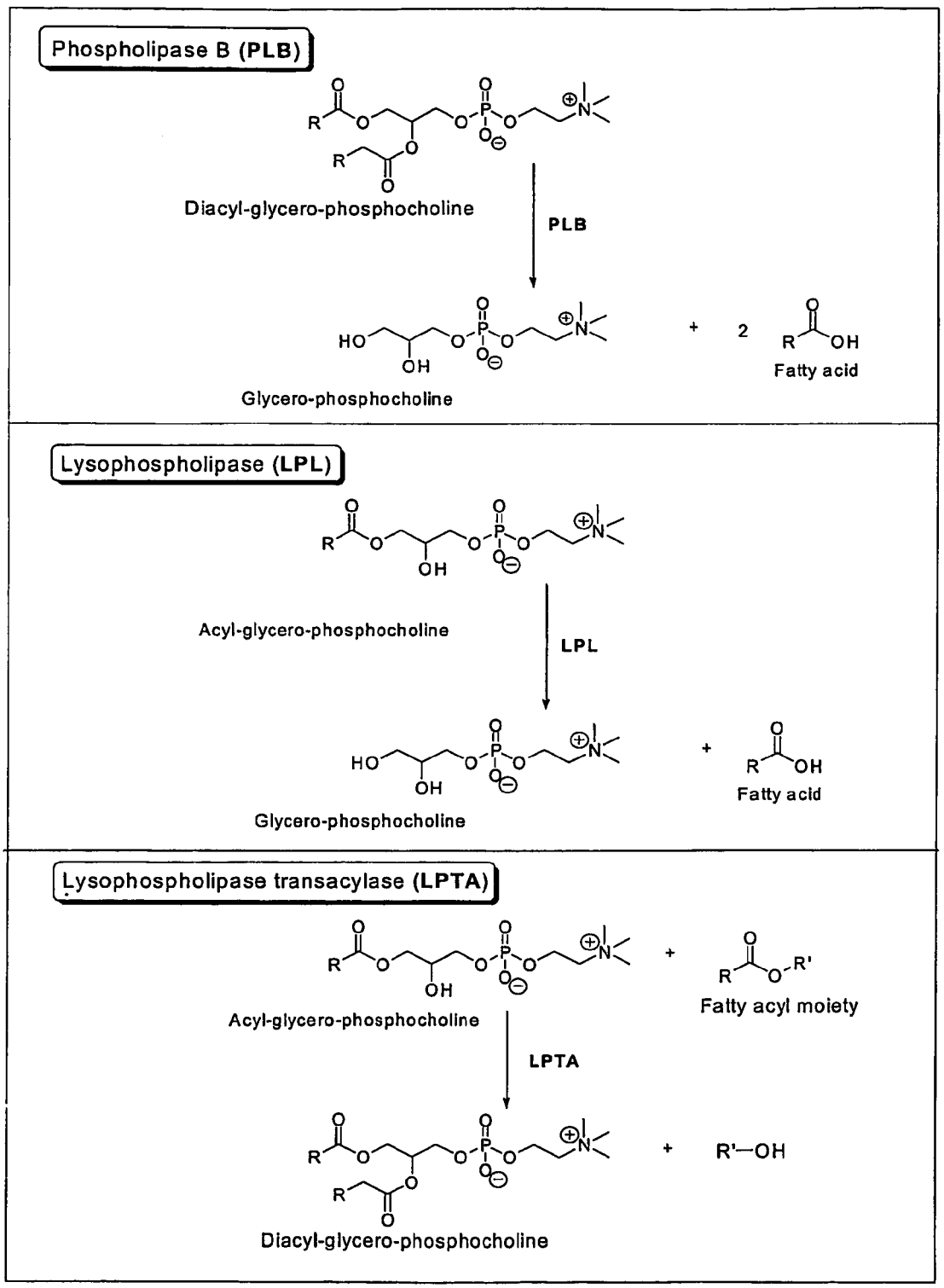
FIG. 1b. The three activities of the cryptococcal phospholipase "PLB".

*Cryptococcus neoformans* is the most common cause of fungal meningitis, which is fatal if untreated. Pathogenic strains of cryptococci produce a number of so-called "virulence factors", one of which is a secreted phospholipase, termed phospholipase B (EC 3.1.1.5). This phospholipase is a single protein containing three separate activities, including (i) phospholipase B activity (PLB), which removes both acyl chains simultaneously from phospholipids, (ii) lysophospholipase (LPL), which removes the single acyl chain from lysophospholipids, and (iii) lysophospholipase transacylase (LPTA), which adds an acyl chain to lysophospholipids to form phospholipids (see FIGS. 1a, 1b).

Secreted phospholipase B is involved in the survival of cryptococci in macrophages, destruction of lung tissue and production of eicosanoids, which modulate phagocytic activity. This Phospholipase B is also related to virulence in other medically important fungi such as *Candida albicans* and *Aspergillus fumigatus*. Consequently, secreted Phospholipase B enzyme may be a potentially useful target for treatment of microbial infection, including, for example, antibacterial, antifungal, antiviral and antiparasitic treatments.

The cell-associated (membrane and cytosolic) phospholipase B activities in *C. neoformans*, were characterised.

Materials and Methods

Fungal isolates and media. A virulent clinical isolate of *C. neoformans* var. *grubii* (serotype A), H99, which produces high levels of secreted phospholipase B activity was used for cell-associated phospholipase characterisation and inhibition of phospholipase activities. Isolate H99 was kindly supplied by Dr. Gary Cox (Duke University Medical Center, Durham, N.C., USA), and subcultured onto Sabouraud dextrose agar (SDA) at 30° C.

Preparation of supernatants containing secreted phospholipase activities. Isolate H99 was grown to confluence on SDA in 16 cm diameter Petri dishes for 72 h at 30° C. in air. Cells scraped from 10-20 dishes were washed sequentially with isotonic saline and imidazole buffer (10 mM imidazole, 2 mM CaCl$_2$, 2 mM Mg Cl$_2$, 56 mM D-Glucose, made up in isotonic saline, pH 5.5), resuspended in a volume of this buffer of about 10% of the cell volume, and incubated for 24 h at 37° C. The cell-free supernatant was separated by centrifugation as previously described and stored at –70° C.

Cellular disruption to prepare membrane and cytosolic fractions. The cell pellet from the preparation of the supernatant, above, was also frozen at –70° C. After washing twice with imidazole buffer, it was disrupted in the presence of a protease inhibitor cocktail (P 8215 for fungal and yeast cells; 4-(2-aminoethyl)benzenesulfonyl fluoride hydrochloride, 100 mM, 1,10-phenanthroline, 500 mM, pepstatin A, 2.2 mM, E-64, 1.4 mM; Sigma) in a MiniBeadbeater-8 Cell Disrupter (MBB-8; Daintree Scientific, Tasmania, Australia) for three cycles of 1 min, alternating with a 1 min cooling period on ice. The homogenate was centrifuged at 14,000 g for 15 min to obtain the membrane (pellet) and the cytosolic (supernatant) fractions. The cytosolic enzyme activities were stable during storage at –70° C. for up to 3 months, whereas the membrane associated activities were less stable (maximum 5 weeks).

Radiometric assay method for phospholipases. Enzyme activities were measured as described previously in a final volume of 125 μL at 37° C. For the determination of secreted PLB activity, carrier dipalmitoyl phosphatidylcholine (DPPC, final concentration 800 μM) and 1,2-di[1-$^{14}$C] palmitoyl phosphatidylcholine (20,000 dpm) were dried under nitrogen and suspended in 125 mM imidazole acetate buffer (assay buffer, pH 4.0) by sonication using a Branson 450 sonifier. The reaction time was 22 min, using 1 μg total protein and PLB activity was determined by the rate of decrease of the radiolabelled PC substrate, with appearance of the label in free fatty acid. Variations to these conditions for the cytosolic and membrane fraction assays are shown in Table 1. This assay also simultaneously allows for the determination of phospholipase A, C and D activities. These activities were measured by the appearance of radiolabel from PC in Lyso PC, diacylglycerol and phosphatidic acid, respectively.

Secreted LPL and LPTA activities were measured simultaneously in a reaction mixture containing 1-[$^{14}$C]palmitoyl lyso-PC (25,000 dpm) and carrier lyso-PC (final concentration 200 µM) in assay buffer. The reaction time was 15 s with 1 µg of total protein and LPL activity was measured by the rate of loss of 1-[$^{14}$C]palmitoyl lyso-PC with release of radio-labelled fatty acids. LPTA activity was estimated from the rate of formation of radiolabelled PC. Variations to these conditions for membrane and cytosolic fractions are presented in Table 1.

All reactions were terminated by adding 0.5 mL of chloroform:methanol (2:1 v/v). The reaction products were extracted by the method as disclosed in Bligh, E. C. and W. J. Dyer. 1959 'A rapid method of total lipid extraction and purification.' Can. J. Biochem. Physiol. 37:911-917, separated by TLC and quantified as previously described. In the case of PLC activity, the TLC plates were developed in petroleum ether (BP 60-80° C.): diethyl ether: acetic acid (90:15:1, v/v/v) instead of chloroform:methanol:water (65:25:4, v/v/v).

TABLE 1

| Optimal conditions for H99 cell-associated and secreted phospholipases | | | | | | |
|---|---|---|---|---|---|---|
| | Cytosolic | | Membrane | | Secreted | |
| Activity | LPL/LPTA | PLB | LPL/LPTA | PLB | LPL/LPTA | PLB |
| Protein (µg) | 1 | 4 | 80 | 120 | 1 | 1 |
| Time | 20 s | 18 min | 30 s | 18 min | 15 s | 22 min |
| Substrate (µM) | 200 | 1000 | 600 | 800 | 200 | 400 |
| PH | 4.0 | 4.0 | 4.0 | 4.0 | 4.0 | 4.0 |

Characterisation of Enzyme Activities

All experiments were carried out in duplicate or triplicate. The effects of pH on the various phospholipase activities were measured using 50 mM final concentration of imidazole-acetate buffer (pH range 3-5), MES buffer (pH range 6-8) and glycine buffer (pH 9-10). Controls for non-enzymic breakdown of substrates were included at all pH values. Cations, Triton X-100 and metal chelators were made up as stock solutions in water and diluted to the final concentration in the appropriate assay buffer.

Protein Assays.

Total protein estimations were performed using a Coomassie Blue binding assay (for supernatant containing secreted enzymes) or the bicinchoninic acid (BCA kit) for cell-associated fractions, with BSA as standard (Pierce Chemical Co., IL, USA).

Identification of PLB, LPL and LPTA in Cell-Associated Fractions.

Assays of cell-associated phospholipase activities were performed at pH 4.0, using the substrates palmitoyl lyso-phosphatidylcholine (Lyso-PC) and DPPC, since these compounds were preferred substrates of the secreted enzyme in both its natural and purified states and enzyme activity was maximal at pH 4.0. Hydrolysis of the substrate lyso-PC by the cryptococcal membrane and cytosolic fractions, resulted in the formation of free fatty acids and PC only, indicating the presence of both LPL and LPTA, as found for the secreted enzyme. Similarly, DPPC, radiolabelled in both acyl chains, was degraded to produce free fatty acids, only, indicating that the activity was due to PLB at pH 4.0.

Effect of Protein Concentration and Time on Phospholipase Activity.

Figure 3:
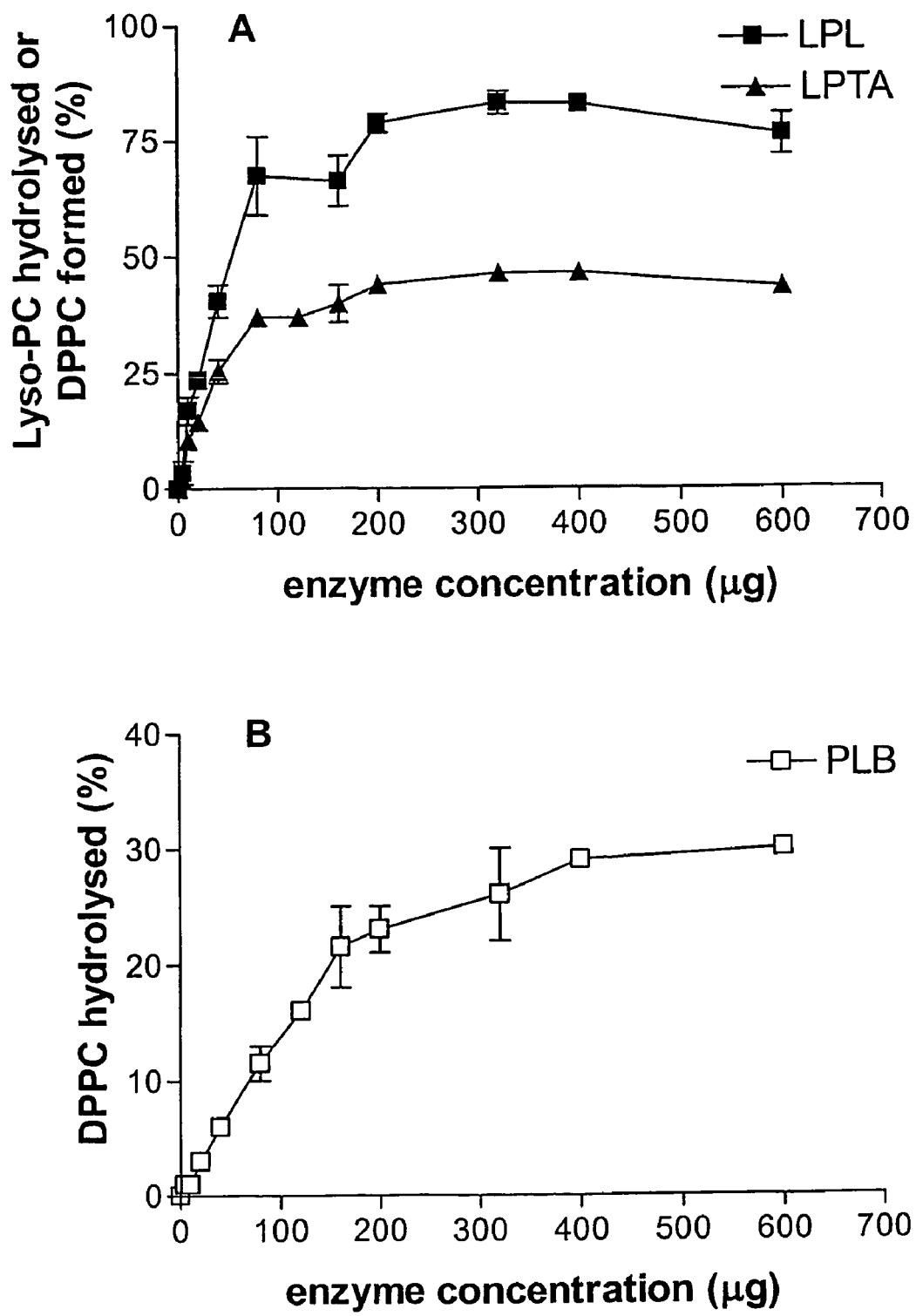
FIG. 3. Effects of protein concentration on membrane-associated phospholipase activities. Points shown are the means and SEM of three assays.

Activity of the cytosolic fraction with increasing protein concentration was linear only to 1 µg for LPL/LPTA and 4 µg for PLB, similar to values for the secreted enzyme (not shown). In contrast, membrane-associated LPL and LPTA activities were linear with increasing protein concentration to 80 µg, after which no further increase occurred (FIG. 3A). The PLB activity was linear to 160 µg protein (FIG. 3B).

The time course of both the cytosolic and membrane activities resembled that of the secreted enzyme, with linearity of LPL/LPTA only to 20-30 sec, beyond which no further increase occurred. Membrane-associated PLB activity was linear to 30 min, whereas cytosolic activity was linear to 22 min (not shown).

Effect of Substrate Concentration on Enzyme Activity.

Figure 4:
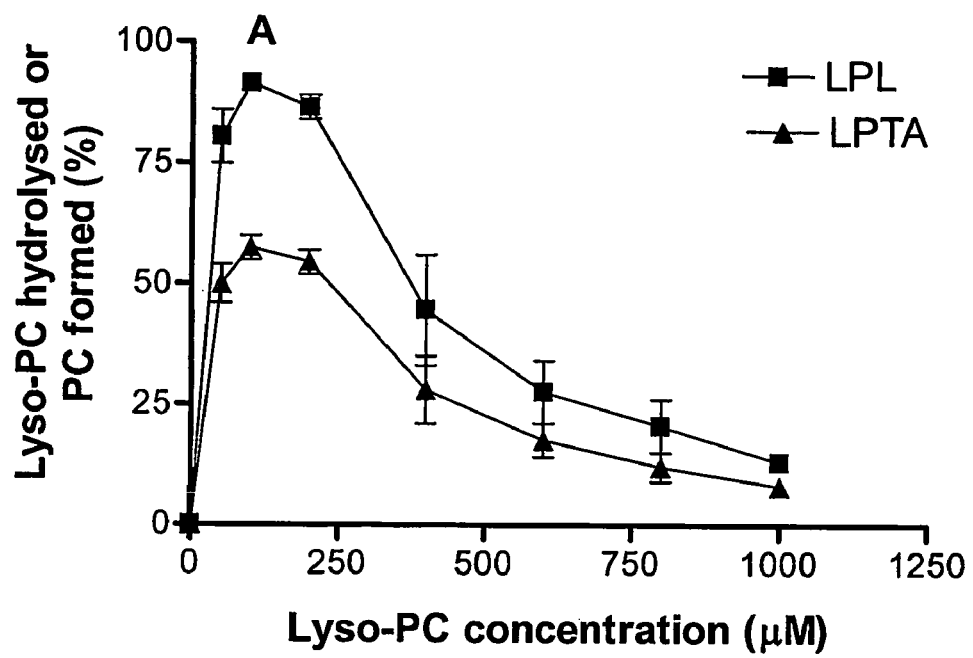
FIG. 4. Effects of substrate concentration on cytosolic phospholipase activities. Points shown are means and SEM of three assays.
Figure 4:
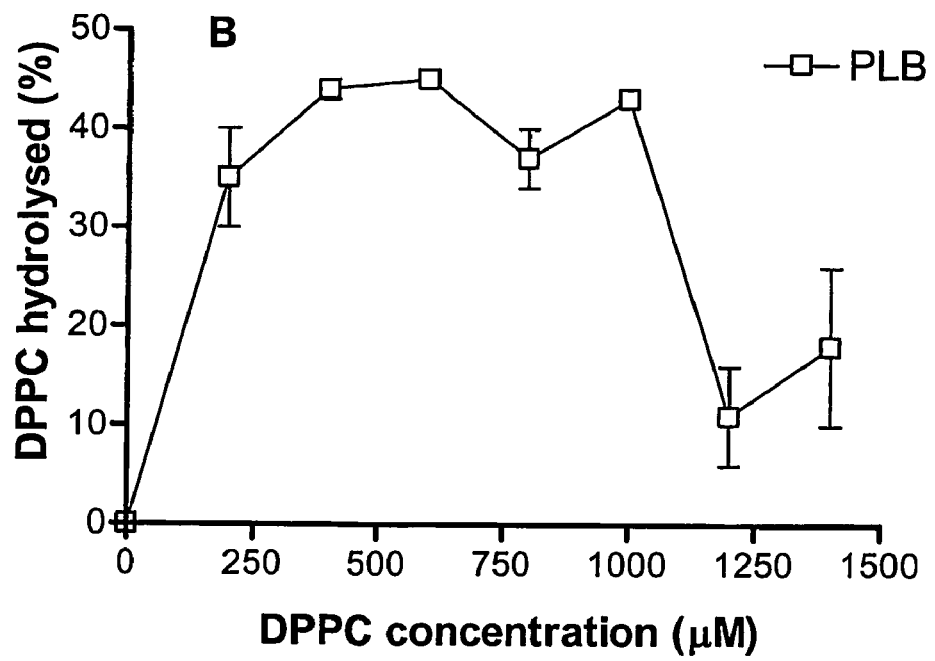

Cytosolic LPL/LPTA activities reached a maximum between 50-200 µM Lyso-PC, after which there was a rapid decline in activity with increasing substrate concentration (FIG. 4A). Cytosolic PLB activity reached saturation at 400 µM DPPC, and declined after 1000 µM (FIG. 4B). Membrane-associated LPL/LPTA reached a maximum around 50 µM Lyso-PC, but maintained the same level of activity until 600 µM, after which it decreased (not shown). The membrane-associated PLB activity reached a maximum at 200 µM DPPC, and declined after 800 µM (not shown).

Effects of pH on Enzyme Activity.

Optimal conditions for further studies were selected from Table 1. Variations in cell-associated phospholipase activity were observed over the pH range 3-10. Cytosolic LPL/LPTA activities exhibited two pH optima, at 4.0 and 6.0, with activity decreasing to zero at pH 9.0 (not shown). The cytosolic phospholipase B pH profile (not shown) was similar to that of membrane-associated PLB (FIG. 5B), though less sharp. The pH optimum was 3-4 for both membrane-associated LPL and LPTA, and decreased gradually to zero at pH 9.0 (FIG. 5A). The optimum pH for membrane PLB (pH 4.0) was very narrow (FIG. 5B), with virtually no activity at pH 7.0.

Figure 5:
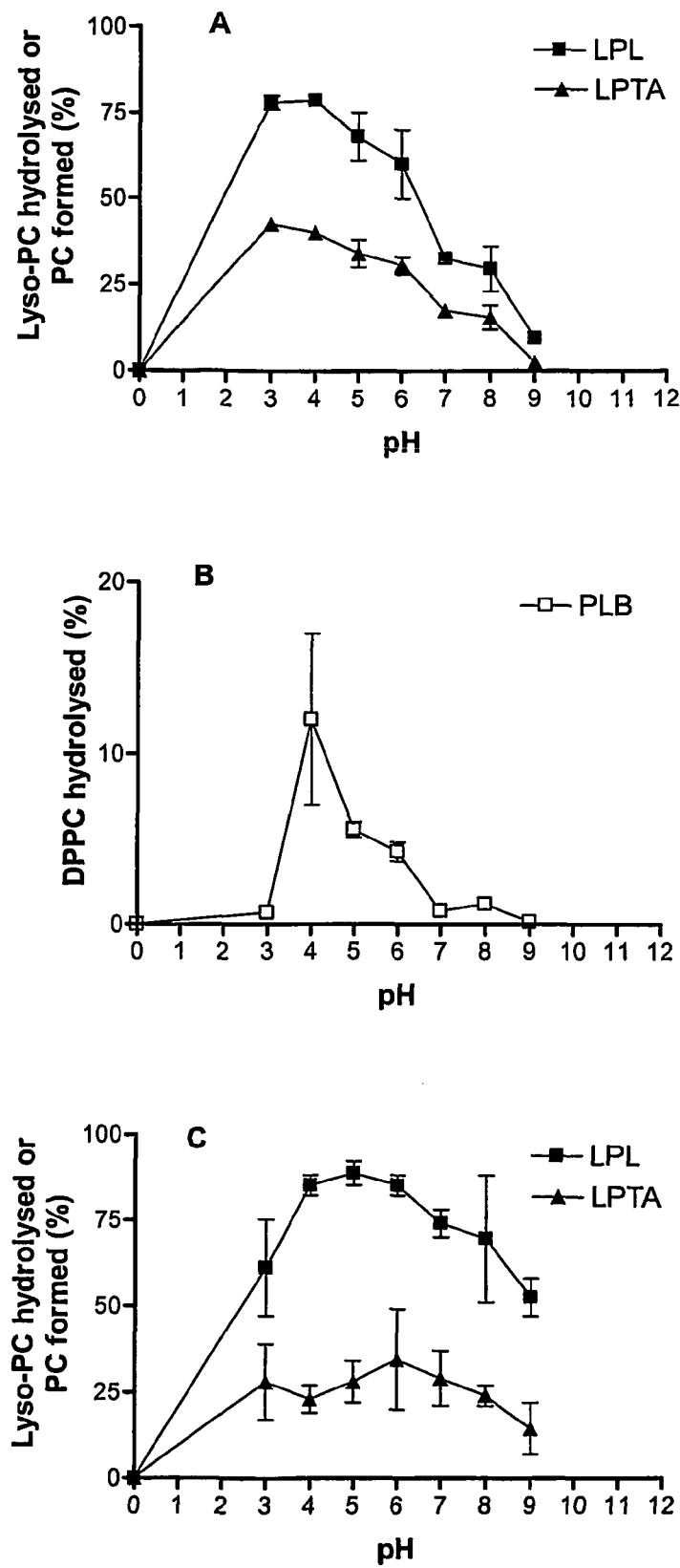
FIG. 5. Effects of pH on membrane-associated phospholipase activities. In A, LPL/LPTA was measured using 30 sec incubation; in C, LPL/LPTA was measured using 10 min FIG. 6. PLA and PLD activity versus pH.

The most obvious difference between the cell associated (cytosolic and membrane-associated) activities and those of both the crude and purified secreted enzymes was the greater activity of the cell-associated enzymes at pH 6.0 (PLB) and 7-8 (LPL/LPTA). Interestingly, when the incubation time for the LPL/LPTA assay was extended from 20-30 sec to 10 min, the activity was increased over the range pH 7-9, but not at lower pH values, in both membrane and cytosolic enzyme preparations (FIG. 5 C, membrane-associated enzyme).

Cellular Distribution of Phospholipase B Activities.

Taking 4.0 as the optimal pH for all three activities (Table 1), it is clear that the distribution of PLB differs from that of LPL and LPTA, in that the greatest percentage of the total activity is secreted (Table 2). With LPL and LPTA most of the activity is cytosolic. The specific activities and percentages of all three activities were lowest in the membrane fraction (Table 2).

TABLE 2

Cellular distribution of phospholipase activities measured at pH 4.0.

| | [a]Specific Activity | | | [b]Total Activity | | | % Distribution | | |
|---|---|---|---|---|---|---|---|---|---|
| | LPL | LPTA | PLB | LPL | LPTA | PLB | LPL | LPTA | PLB |
| Secreted | 86.6 | 53.9 | 2.1 | 650 | 405 | 16.2*# | 36.1 | 29.9 | 82.7*# |
| | (7.2) | (3.5) | (0.29) | (54) | (26) | (2.1) | (1.4) | (1.9) | (10.7) |
| Cytosolic | 78.4 | 68.9 | 0.2 | 955* | 839* | 2.5 | 53.1* | 62.0* | 12.8 |
| | (12.6) | (20.6) | (0.15) | (154) | (251) | (1.8) | (8.6) | (18.6) | (9.2) |
| Membrane | 0.54 | 0.31 | 0.003 | 195 | 109 | 0.9 | 10.8 | 8.1 | 4.6 |
| | (0.28) | (0.15) | (0.001 | (99) | (53) | (0.4) | (5.5) | (3.9) | (2.0) |

Data are expressed as the means and SEM of at least three assays, with activities calculated as μmol substrate degraded or product formed (LPTA) per min per mg protein[a] or per total protein[b] in the cellular fraction.
*P < 0.01, compared with membrane activity;
P < 0.01, compared with cytosolic activity (ANOVA)

Modifying Agents and Cell-Associated Activities.

There was no stimulation of any of the cytosolic or membrane-associated activities by 10 mM calcium or magnesium at pH 4.0 (Table 3A). Triton X-100 was the only notable inhibitor at pH 4.0, with cytosolic and membrane-associated LPTA and PLB most affected (Table 3A).

TABLE 3

Effects of modifying agents on cytosolic and membrane-associated activities.

(A) Assayed at pH 4.0[a]

| | Cytosolic | | | Membrane-associated | | |
|---|---|---|---|---|---|---|
| Modifier | LPL[b] | LPTA[b] | PLB | LPL[b] | LPTA[b] | PLB[b] |
| Calcium | 100 | 100 | 100 | 100 | 96 | 83 |
| Magnesium | 73 | 70 | 100 | 97 | 91 | 79 |
| EDTA | 100 | 100 | 100 | 98 | 94 | 87 |
| EGTA | 86 | 88 | 100 | 100 | 90 | 77 |
| FeCl$_3$ | 81 | 78 | 79 | 97 | 75 | 92 |
| Triton X-100 | 62 | 39 | 54* | 71 | 52 | 19 |

(B) Assayed at pH 7.0[a]

| | LPL[b] | LPTA[b] | PLB | LPL | LPTA | PLB |
|---|---|---|---|---|---|---|
| Calcium | 236 | 206 | 591* | 166* | 140* | 533* |
| Magnesium | 96 | 85 | 477* | 145* | 123* | 467* |
| EDTA | 30 | 32 | 100 | 96 | 100 | 67 |
| EGTA | 26 | 29 | 163 | 100 | 100 | 200 |
| FeCl$_3$ | 22 | 21 | 61 | 61* | 45* | 2* |
| Triton X-100 | 0.9 | 0 | 59 | 4* | 2* | 33* |

[a]Activities are expressed as percentages of the control, taken as 100%. Values are the means of triplicate or
[b]duplicate assays.
Final concentrations of modifying agents were 10 mM, except for Triton X-100, which was 0.1%(w/v).
*Significantly different from the controls, P < 0.01, by the Dunnett Multiple Comparisons Test.

When assayed at pH 7.0, all three of both cytosolic and membrane-associated activities were stimulated by calcium (Table 3B). Cytosolic PLB, and all three of the membrane-associated activities were also stimulated by magnesium (Table 3B). This was reflected in lower activity in the presence of EDTA and EGTA for cytosolic LPL and LPTA. Both FeCl$_3$ and Triton X-100 were inhibitors of all three activities, from both cytosolic and membrane-bound fractions. Triton X-100 was less effective in inhibiting the PLB, than the LPL and LPTA activities (Table 3B).

Phospholipases A, C, and D.

Figure 6:
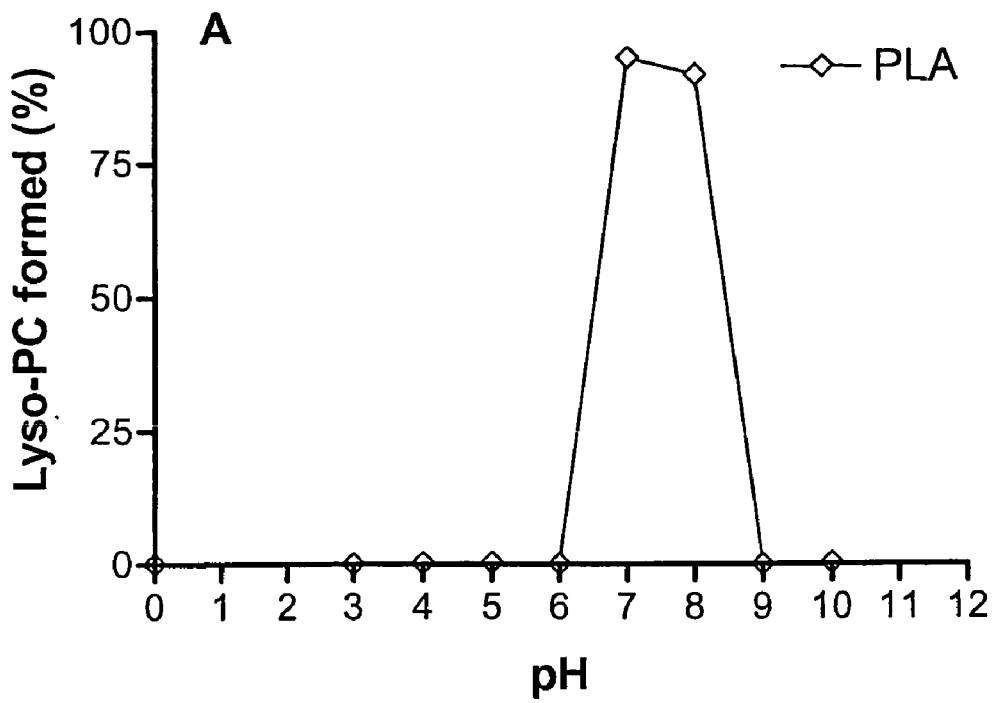
Figure 6:
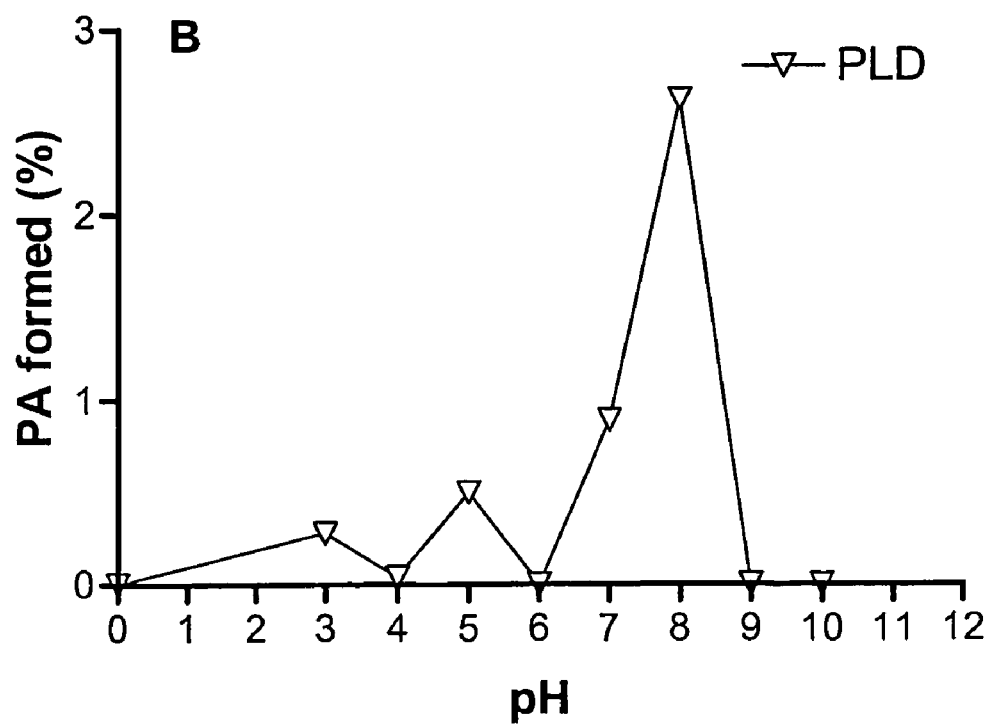

Secreted forms of Phospholipases A, C, and D have not been identified in cryptococcal supernatants. High levels of phospholipase A (PLA) were detected by the formation of radiolabelled Lyso-PC from DPPC at pH 7-8 in membrane preparations (FIG. 6A), but only trace amounts of PLA were found in the cytosolic fraction (not shown). Small amounts of phospholipase D (PLD) activity were detected by the formation of radiolabelled phosphatidic acid from both cytosolic and membrane fractions at pH 7-8 (FIG. 6B, membrane PLD). No evidence of PLC was found at any pH value using DPPC as substrate.

Under the assay conditions tested, phospholipase B was the major phospholipase is present in the cytosol and secreted from *C. neoformans*. In contrast, phospholipases A and D were membrane-associated, with some PLD activity in the cytosol. The pH optimum for PLB activity, whether secreted, membrane-bound or cytosolic, was always acidic (pH 4.0), whereas the cytosolic LPL/LPTA was bimodal (pH 4.0 and 6.0). PLA and PLD activities were detected only at pH 7-8. These observations are consistent with the role of secreted PLB activities in cryptococcal virulence since the putative sites of action of Phospholipase B are the acidic vacuoles of macrophage-like cell lines, and mouse macrophages in vivo.

The membrane-associated LPL/LPTA activities were stimulated by both calcium and magnesium (Table 3). The unexpected stimulation of cell-associated PLB activity by calcium and magnesium at pH 7.0 might be due in part to PLA activity.

Example 3

Selection and Testing of Potential Phospholipase Inhibitors

Materials and Methods

Selection of potential phospholipase inhibitors. Selection of potential inhibitors was based on the traditional approach of testing compounds that are structurally related to the substrate, i.e. phospholipids. Commercially available compounds were initially used containing the two dominant features in phospholipids (one or two hydrophobic alkyl chains and a tetra-alkylated strongly positively charged nitrogen atom), which would be metabolically stable and sufficiently water-soluble to avoid use of solvents in the assays.

Preparation of inhibitors and use in assays. The following compounds were tested (for structures, see FIG. 2): compound 1, 1,12-bis(tributylphosphonium)dodecane dibromide (Fluka AG, Buchs, Switzerland); compound 2, 1,10-bis(tributylammonium)-decane dibromide; compound 3, 1,12-bis(tributylammonium)do-decane dibromide (both synthesised in-house); compound 4, 1,10-bis(trimethylammonium)decane dibromide ["decamethonium"] (Sigma, St. Louis Mo., USA). All compounds were prepared as stock solutions of 700 µM in assay buffer containing 5 mM EDTA, which was then diluted serially with buffer to obtain solutions of 70, 7, 0.7 and 0.07 µM. In each assay, 45 µL of these solutions was used, and the final volume of 125 µL was made up of substrate, enzyme and buffer. The radiometric assay was carried out as above. Inhibition was calculated as the percent of substrates (DPPC or Lyso-PC) remaining in the case of PLB and LPL activities, or of DPPC produced, in the case of the LPTA activity. The amounts converted, or produced, in the inhibitor-free control were normalised to 100%, and the inhibition calculated against it. All assays were done in triplicate.

Pancreatic phospholipase assay. Porcine pancreatic phospholipase $A_2$ suspension in 3.2M ammonium sulfate (2.9 mg protein/mL, Sigma St.Louis Mo., USA) was used. One part of well mixed enzyme suspension was added to 4 parts of buffer (10 mM Tris/HCl, pH 8.2; 10 mM $CaCl_2$. Activity and inhibition by test compounds was then measured by the radiometric method described in Example 2 for fungal PLB activity. However, 25 µL enzyme solution was used, and the reaction time was 1 hour. These conditions result in ~60% substrate conversion in the inhibitor-free control.

Antifungal susceptibility testing. The antifungal activity of the compounds was measured by a standard microdilution method. The minimal inhibitory concentration of each compound (MIC) was defined as that which produced no visible growth after 48 h of culture (*Candida*) and 72 h (*Cryptococcus*) at 35° C. The fungal strains tested included *Cryptococcus neoformans* H99, *Cryptococcus neoformans* ATCC 90112 and *Candida albicans* ATCC 10231. All tests were performed in duplicate.

Figure 2:
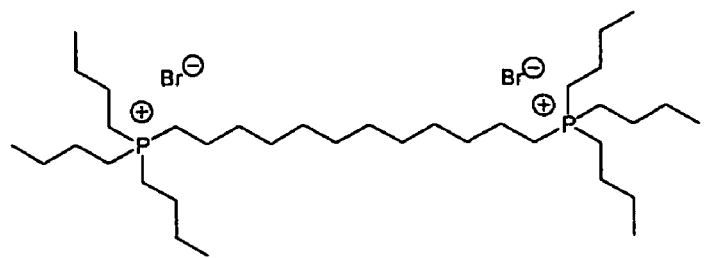
FIG. 2. Structures of exemplary bis-cationic compounds in accordance with the present invention.
Figure 2:
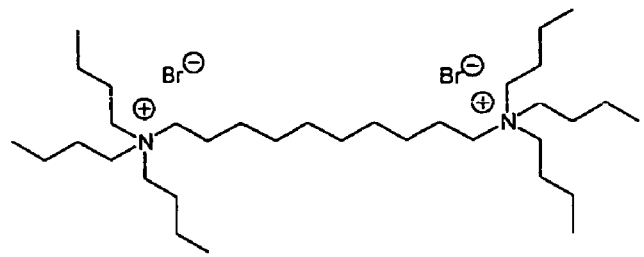
Figure 2:
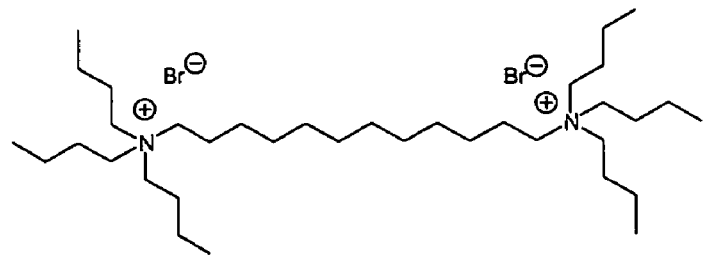
Figure 2:
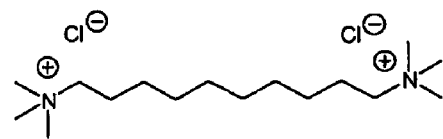

Ammonium- and phosphonium compounds were examined. The structures and common names of four compounds studied are shown in FIG. 2. These compounds each have a strong positive charge and fatty acid-like hydrophobicity.

Assays were performed at pH 4 in the absence of added cations, using the optimised conditions summarised in Table 1. Under these conditions only PLB, LPL and LPTA activities (both secreted and cell-associated) were measured. Initially, compounds deemed to be potential inhibitors were assayed at 25 and 250 µM. Those showing some inhibition were then also assayed at 2.5 and 0.25 µM.

This bis-tributylphosphonium compound (1) inhibits PLB activity more so than LPL or LPTA. Importantly it inhibits the cytosolic as well as the secretory enzyme, while it has no effect on the membrane-bound enzyme (Table 4). Interestingly, it inhibits the porcine pancreatic PLA2 more strongly than the fungal secretory Phospholipase B (Table 5). This is in contrast to the two bis-tributylammonium compounds (2 and 3) which inhibit the fungal enzyme more strongly, and thus form a platform to achieve even higher selectivity. The fungicidal activity of these three tributyl bis-cationic compounds is quite strong, the best having an MIC of 2.5 µMolar (Table 6). There is a sharp drop in MIC as the chain length is increased by two $CH_2$ groups, and, importantly this increase in chain length also increases the inhibition potency (Table 5). Compound (4), which has only methyl-alkylation at the quaternary nitrogen, shows neither enzyme inhibition nor antifungal activity (Tables 4 and 5).

TABLE 4

Inhibition of the activities of *C. neoformans* strain H99 phospholipases by 1,12-bis(tributylphosphonium)dodecane dibromide (1)

| | % Inhibition[b] | | | | | | | | | | | |
|---|---|---|---|---|---|---|---|---|---|---|---|---|
| | LPL | | | | LPTA | | | | PLB | | | |
| Compound[a] | 0.25 | 2.5 | 25 | 250[c] | 0.25 | 2.5 | 25 | 250[c] | 0.25 | 2.5 | 25 | 250[c] |
| Secretory Enzyme | | | | | | | | | | | | |
| 1[a] | 0 | 0 | 0 | 6.3* (0.8) | 0 | 0 | 0 | 3.7* (0.6) | 0 | 0 | 35.2* (1.5) | 55.0* (1.5) |
| Cytosolic Enzyme | | | | | | | | | | | | |
| 1 | n.d. | 0 | 0 | 12.7* (0.9) | n.d. | 0 | 0 | 0 | n.d. | 0 | 0 | 41.3* (2.3) |
| Membrane-bound Enzyme | | | | | | | | | | | | |
| 1 | n.d. | 0 | 0 | 0 | n.d. | 0 | 0 | 0 | n.d. | 0 | 0 | 0 |

[a]The structures and abbreviations for these compounds are shown in FIG. 2. Compound 4 did not inhibit any of the activities of any enzyme at these concentrations.
[b]Data are expressed as the means and SEM (in brackets) of at least three assays.
*Significantly different from the inhibitor-free controls, P < 0.01 by the Dunnett Multiple Comparison Test.
[c]Concentrations are µM
n.d. = not determined.

TABLE 5

Inhibition[a] of Secretory Cryptococcal H99 Phospholipase and ppPLA$_2$ by Dimeric Cationic Compounds.

| | Test Compounds[b] | | | | | | | |
|---|---|---|---|---|---|---|---|---|
| | 1,10-bis(tributyl)ammonium decane (2) | | 1,12-bis(tributyl)ammonium dodecane (3) | | 1,12-bis(tributylphosphonium) dodecane (1) | | 1,10-bis(trimethylammonium) decane [decamethonium] (4) | |
| Conc. (μM) | PLB | ppPLA$_2$ | PLB | ppPLA$_2$ | PLB | ppPLA$_2$ | PLB | ppPLA$_2$ |
| 250 | 90 | 65 | 85 | 86 | 55 | 97 | 0 | 0 |
| 25 | 80 | 25 | 80 | 36 | 35 | 62 | 0 | 0 |
| 2.5 | 30 | 0 | 65 | 0 | 0 | 5 | 0 | 0 |
| 0.25 | 0 | 0 | 20 | 0 | 0 | 0 | n.d | n.d. |

[a]Data are expressed as percentage inhibition of activity and are the means of at least three assays.
[b]Structures and abbreviations are given in FIG. 2.
n.d. = not determined.

Example 4

Antifungal Activity

Compounds 1-4 referred to in Example 3 were assayed for antifungal activity in a standardised serial dilution sensitivity test against two strains of *C. neoformans* and one strain of *Candida albicans* (Table 6). The two stronger phospholipase inhibitors (1 and 3) were quite potent, with MIC in the 2.5 to 10 μM range, whereas the non-inhibitory decamethonium compound (4) had a much higher MIC (88 μM-350 μM) (Table 6).

Example 5

Antifungal Activity

A range of cationic compounds were assayed for antifungal activity in a standardised serial dilution sensitivity test against *C. neoformans* (ATCC 90122) and *C. Albicans* (ATCC 10231). Results are presented in Table 7. A good correlation was observed between inhibition and antifungal activity.

TABLE 6

MIC of synthesised Compounds Tested against *C. neoformans* reference strain ATCC 90112 and *Candida albicans* reference strain ATCC 10231

| Name | FW | C. neof. ATCC 90112 μM | C. albicans ATCC 10231 μM |
|---|---|---|---|
| Amphotericin B (control) | 924 | 0.55 | 1.1 |
| 1,10-bis(Trimethylammonium)decane, dichloride ["Decamethonium"] (4) | 418 | 88 | >350 |
| 1,10-bis(Tributylammonium)decane, dibromide (2) | 656 | 11 | 88 |
| 1,12-bis(Tributylammonium)dodecane, dibromide (3) | 698 | 2.5 | 11 |
| 1,12-bis(Tributylphosphonium)dodecane, dibromide (1) | 733 | 2.5 | 8.8 |

TABLE 7

| Name | Structure | MIC (μM) Crypto. (ATCC 90112) | MIC (μM) C. alb. (10231) | Haemolytic assay (%) | PLB assay (% inhibition) | Lyso assay (% inhibition) LPL | Lyso assay (% inhibition) LPTA |
|---|---|---|---|---|---|---|---|
| 1,10-bis(trimethyl ammonium) decane dibromide | Me₃N⁺–(chain)–⁺NMe₃ •2Br⁻ C₁₆H₃₈Br₂N₂ (m.w 418.3) | ≧350 | ≧350 | | 250 μM = 0%<br>25 μM = 0%<br>2.5 μM = 0%<br>0.25 μM = 0% | 250 μM = 0%<br>25 μM = 0%<br>2.5 μM = 0%<br>0.25 μM = 0% | 250 μM = 0%<br>25 μM = 0%<br>2.5 μM = 0%<br>0.25 μM = 0% |
| 1,12-bis(trimethyl ammonium) dodecane dibromide (CN20114) | Me₃N⁺–(chain)–⁺NMe₃ •2Br⁻ C₁₈H₄₂Br₂N₂ (m.w 446.4) | 175 | 175 | 350 μM = 0%<br>175 μM = 0%<br>88 μM = 0%<br>35 μM = 0%<br>3.5 μM = 0% | 250 μM = 3%<br>25 μM = 2%<br>2.5 μM = n.d.<br>0.25 μM = n.d. | 250 μM = 5%<br>25 μM = 4% (A)<br>2.5 μM = n.d.<br>0.25 μM = n.d. | 250 μM = 5%<br>25 μM = 4% (A)<br>2.5 μM = n.d.<br>0.25 μM = n.d. |
| 1,12-bis(triethyl ammonium) dodecane dibromide (CN2-48) | Et₃N⁺–(chain)–⁺NEt₃ •2Br⁻ C₂₄H₅₄Br₂N₂ (m.w 530.5) | 11 | 22 | | n.d. | n.d. | n.d. |
| 1,12-bis(tripropyl ammonium) dodecane dibromide | Pr₃N⁺–(chain)–⁺NPr₃ •2Br⁻ C₃₀H₆₆Br₂N₂ (m.w 614.7) | 5.5 | 10 | | 250 μM = 80%<br>25 μM = 71%<br>12.5 μM = 68%<br>6.7 μM = 42%<br>2.5 μM = 6%<br>0.25 μM = 5% | 250 μM = 8%<br>25 μM = 5%<br>2.5 μM = 0%<br>0.25 μM = 0% | 250 μM = 10% (A)<br>25 μM = 20% (A)<br>2.5 μM = 0%<br>0.25 μM = 0% |
| 1,10-bis(tributyl ammonium) decane dibromide | Bu₃N⁺–(chain)–⁺NBu₃ •2Br⁻ C₃₄H₇₄Br₂N₂ (m.w 670.8) | 11 | 88 | | 250 μM = 90%<br>25 μM = 80%<br>2.5 μM = 30%<br>0.25 μM = 0% | n.d. | n.d. |
| 1,11-bis(tributyl ammonium) undecane dichloride | Bu₃N⁺–(chain)–⁺NBu₃ •2Cl⁻ C₃₅H₇₆Cl₂N₂ (m.w 595.9) | 22 | 44 | | n.d. | n.d. | n.d. |

TABLE 7-continued

| Name | Structure | MIC (μM) Crypto. (ATCC 90112) | MIC (μM) C. alb. (10231) | Haemolytic assay (%) | PLB assay (% inhibition) | Lyso assay LPL (% inhibition) | Lyso assay LPTA (% inhibition) |
|---|---|---|---|---|---|---|---|
| 1,12-bis(tributyl ammonium) dodecane dichloride | ⊕Bu₃N~~~NBu₃⊕ •2Cl⁻  C₃₆H₇₈Cl₂N₂ (m.w. 609.9) | 2.5 | 5.5 | 350 μM = 100%<br>175 μM = 5%<br>88 μM = 0%<br>35 μM = 0%<br>3.5 μM = 0% | 250 μM = 85%<br>25 μM = 65%<br>12.5 μM = 56%<br>6.7 μM = 35%<br>2.5 μM = 6%<br>0.25 μM = 0% | n.d. | n.d. |
| 1,12-bis(tributyl phosphonium) dodecane dibromide | ⊕Bu₃P~~~PBu₃⊕ •2Br⁻  C₃₆H₇₈Br₂P₂ (m.w. 732.8) | 2.5 | 8.8 | 700 μM = 75%<br>350 μM = 5%<br>175 μM = 0%<br>88 μM = 0%<br>35 μM = 0%<br>3.5 μM = 0% | 250 μM = 55%<br>25 μM = 35%<br>2.5 μM = 0%<br>0.25 μM = 0% | 250 μM = 6%<br>25 μM = 0%<br>2.5 μM = 0%<br>0.25 μM = 0% | 250 μM = 4%<br>25 μM = 0%<br>2.5 μM = 0%<br>0.25 μM = 0% |
| 1,12-bis(tri-isobutyl ammonium) dodecane dibromide | ⊕(i-Butyl)₃N~~~N(i-Butyl)₃⊕ •2Br⁻  C₃₆H₇₈Br₂N₂ (m.w. 698.8) | ≧350 | ≧350 | 350 μM = 0%<br>175 μM = 0%<br>88 μM = 0%<br>35 μM = 0%<br>3.5 μM = 0% | 250 μM = 0%<br>25 μM = 0%<br>2.5 μM = n.d.<br>0.25 μM = n.d. | 250 μM = 0%<br>25 μM = 0%<br>2.5 μM = 0%<br>0.25 μM = 0% | 250 μM = 5%<br>25 μM = 4%<br>2.5 μM = n.d.<br>0.25 μM = n.d. |
| 1,12-bis(tripentyl ammonium) dodecane dibromide | ⊕(Pentyl)₃N~~~N(Pentyl)₃⊕ •2Br⁻  C₄₂H₉₀Br₂N₂ (m.w. 783) | 5.5 | 5.5 | 350 μM = 100%<br>175 μM = 5%<br>88 μM = 0%<br>35 μM = 0%<br>3.5 μM = 0% | 250 μM = 63%<br>25 μM = 73%<br>2.5 μM = 12%<br>0.25 μM = 0% | 250 μM = 10%<br>25 μM = 10%<br>2.5 μM = n.d.<br>0.25 μM = n.d. | 250 μM = 2.4%<br>25 μM = 0%<br>2.5 μM = n.d.<br>0.25 μM = n.d. |
| 1,12-bis(tri-isopentyl ammonium) dodecane dichloride | ⊕(i-Pentyl)₃N~~~N(i-Pentyl)₃⊕ •2Cl⁻  C₄₂H₉₀Cl₂N₂ (m.w. 694.1) | 4.4 | 2.2 | 350 μM = 100%<br>175 μM = 30%<br>88 μM = 4%<br>35 μM = 0%<br>3.5 μM = 0% | 250 μM = 63%<br>25 μM = 68%<br>12.5 μM = 56%<br>6.7 μM = 38%<br>2.5 μM = 9%<br>0.25 μM = 0% | 250 μM = 11%<br>25 μM = 11%<br>2.5 μM = n.d.<br>0.25 μM = n.d. | 250 μM = 6%<br>25 μM = 0%<br>2.5 μM = n.d.<br>0.25 μM = n.d. |
| 1,12-bis(trihexyl ammonium) dodecane dichloride | ⊕(Hexyl)₃N~~~N(Hexyl)₃⊕ •2Cl⁻  C₄₈H₁₀₂Cl₂N₂ (m.w. 778.2) | 17.5 | 8.8 | | | | |
| 1,12-bis(trioctyl ammonium) dodecane dichloride | ⊕(Octyl)₃N~~~N(Octyl)₃⊕ •2Cl⁻  C₆₀H₁₂₄Cl₂N₂ (m.w 932.5) | 35 | 100 | | | | |

TABLE 7-continued

| Name | Structure | MIC (μM) Crypto. (ATCC 90112) | MIC (μM) C. alb. (10231) | Haemolytic assay (%) | PLB assay (% inhibition) | Lyso assay (% inhibition) LPL | Lyso assay (% inhibition) LPTA |
|---|---|---|---|---|---|---|---|
| 1,16-bis(tributyl ammonium) hexadecane dichloride | C₄₀H₈₆Cl₂N₂ (m.w 665) | 2.2 | 5.5 | | 250 μM = 62%<br>25 μM = 48%<br>2.5 μM = n.d.<br>0.25 μM = n.d. | 250 μM = 10%<br>25 μM = 5%<br>2.5 μM = n.d.<br>0.25 μM = n.d. | 250 μM = 6% (A)<br>25 μM = 15% (A)<br>2.5 μM = n.d.<br>0.25 μM = n.d. |
| 1,16-mono(tributyl ammonium) hexadecane dibromide | C₂₉H₆₂BrN (m.w 504.7) | n.d. | 1.4 | 350 μM = 100%<br>175 μM = 75%<br>88 μM = 19%<br>35 μM = 4%<br>3.5 μM = 2.5% | | | |
| 1,16-mono(tributyl phosphonium) hexadecane dibromide | C₂₉H₆₂BrP (m.w 521.7) | ≦0.6 | 2.2 | 350 μM = 100%<br>175 μM = 32%<br>88 μM = 7%<br>35 μM = 4%<br>3.5 μM = 2.5% | 250 μM = 92%<br>25 μM = 37%<br>2.5 μM = 15%<br>0.25 μM = 0% | 250 μM = 98%<br>25 μM = 15%<br>2.5 μM = 0%<br>0.25 μM = 0% | 250 μM = 95%<br>25 μM = 5%<br>2.5 μM = 0%<br>0.25 μM = 0% |
| C₁₂-bis-N-methyl-pyro. dibromide | C₂₈H₄₆Br₂N₂ (m.w 498.4) | 175 | 175 | n.d. | 250 μM = 9%<br>25 μM = 0%<br>2.5 μM = n.d.<br>0.25 μM = 0% | 250 μM = 0%<br>25 μM = 0%<br>2.5 μM = n.d.<br>0.25 μM = 0% | 250 μM = 0%<br>25 μM = 0%<br>2.5 μM = n.d.<br>0.25 μM = 0% |
| C₁₂-bis-N-butyl-pyro. dibromide | C₂₈H₅₈Cl₂N₂ (m.w 493.7) | 88 | 88 | 350 μM = 0%<br>175 μM = 0%<br>88 μM = 0%<br>35 μM = 0%<br>3.5 μM = 0% | | | |

TABLE 7-continued

| Name | Structure | MIC (μM) Crypto. (ATCC 90112) | MIC (μM) C. alb. (10231) | Haemolytic assay (%) | PLB assay (% inhibition) | Lyso assay (% inhibition) LPL | Lyso assay (% inhibition) LPTA |
|---|---|---|---|---|---|---|---|
| Hemicholinium dibromide | $C_{24}H_{34}Br_2N_2O_4$ (m.w 574.4) | n.d. | ≧350 | 350 μM = 0%<br>175 μM = 0%<br>88 μM = 0%<br>35 μM = 0%<br>3.5 μM = 0% | | | |
| Gallamine triethiodide | $C_{30}H_{60}I_3N_3O_3$ (m.w 891.5) | n.d. | ≧350 | 350 μM = 0%<br>175 μM = 0%<br>88 μM = 0%<br>35 μM = 0%<br>3.5 μM = 0% | | | |
| 1,12-bis[N-Methyl-morpholinium]dodecane | $C_{22}H_{46}Br_2N_2O_2$ (m.w 530.4) | 44 | 88 | n.d. | | | |
| 1,12 bis-(Quinuclidinium) dodecane dibromide | $C_{26}H_{50}Br_2N_2$ (m.w 550.5) | 350 | ≧350 | n.d. | 250 μM = 5%<br>25 μM = 0%<br>2.5 μM = 0%<br>0.25 μM = 0% | 250 μM = 0%<br>25 μM = 0%<br>2.5 μM = 0%<br>0.25 μM = 0% | 250 μM = 0%<br>25 μM = 0%<br>2.5 μM = 0%<br>0.25 μM = 0% |

Example 6

Hemolytic activity Assay

Human blood was collected in 10 mL Vacutainer tubes containing potassium-EDTA as anticoagulant. The blood from each vacutainer was transferred to a 50 mL centrifuge tube and the cells washed three times with calcium- and magnesium-free phosphate buffered saline (PBS) (Gibco) by centrifugation at 2000×g for 15 min. The third supernatant was clear and colourless. Cells were stored in PBS for up to two weeks. The cell suspension in PBS (0.5 mL) was mixed with a stock solution of test substance (0.5 mL) at the appropriate concentration (final erythrocyte concentration of approx. $0.5 \times 10^9$ per mL). The mixtures were incubated at 37° C. for 1 h with gentle shaking, then centrifuged at 2000×g for 10 min. The supernatant was diluted 10-fold with PBS and the optical density measured at 540 nm. The values for 0% and 100% lysis were determined by incubating cells with PBS or 0.1% Triton X-100 (in water), respectively. Assays were carried out in triplicate. Results are shown in Table 7. Hemolytic activity of potent antifungal compounds was found to be negligible at concentrations fifty or more times above MIC.

Example 7

In Vitro Antibacterial Activity

Two bis-cationic compounds were tested for antibacterial activity. The assay used was that published by the National Committee for Clinical Laboratory Standards. 2003. Methods for Dilution Antimicrobial Susceptibility Tests for Bacteria That Grow Aerobically: Approved Standard—Sixth Edition. NCCLS document M7-A6. Villanova, Pa., USA. The results are shown in Table 8.

Example 8

In Vitro Antifungal Activity

Two bis-cationic compounds were tested for antifingal activity.

The assay used for filamentous fungi (*Aspergillus; Scedosporium; Fusarium*) was that published by the National Committee for Clinical Laboratory Standards. 2002. Reference Method for Broth Dilution Antifungal Susceptibility Testing of Filamentous Fungi: Approved Standard. NCCLS document M38-A.Villanova, Pa., USA.

The assay used for yeasts (*Candida; Cryptococcus*) is that of the National Committee for Clinical Laboratory Standards. 1997. Reference Method for Broth Dilution Antifungal Susceptibility Testing of Yeasts: Approved Standard. NCCLS document M27-A.Villanova, Pa., USA as published in Ghannoum, M. A., A. S. Ibrahim, Y. Fu, M. C. Shafiq, J. E Edwards, Jr. and R. S. Criddle. 1992. Susceptibility testing of *Cryptococcus neoformans*: A microdilution technique. *J. Clin. Microbiol.* 30:2881-2886. The results are shown in Table 9.

TABLE 8

Invitro antibacterial properties of two bis-ammonium compounds (MICs are reported as µg/ml and µM)

| Bacteria | 1,12-bis(tributylammonium)dodecane (FW: 608.0) | | 1,16-bis(tributylammonium)hexadecane (FW: 664.0) | |
| --- | --- | --- | --- | --- |
| | µg/ml | µM | µg/ml | µM |
| Gram-negative | | | | |
| *Escherichia coli*[a] 25922 | 13.4 | 22 | n.d. | n.d. |
| *Pseudomonas ariginosa*[b] 122 | 48 | 80 | 106 | 160 |
| Gram-positive | | | | |
| *Staphylococcus aureus*[c] 25923 | 3.3 | 5.5 | n.d. | n.d. |
| MRSA[d] (methicillin resistant *S. aureus*) | 3.3 | 5.5 | 5.0 | 11 |
| *Streptococcus pneumonia*[e] 49619 | 0.73 | 1.2 | n.d. | n.d. |
| VRE[f] (Vancomycin resistant *Enterococcus*) | 1.6 | 2.7 | 3.6 | 5.5 |

[a]Positive control was amoxicillin (FW: 365.4). MIC obtained was 8-16 µg/ml
[b]Positive control was Gentamicin (FW: 470). MIC obtained was 1.0 µg/ml.
[c]Positive control was amoxicillin (FW: 365.4). MIC obtained was 0.25-0.50 µg/ml
[d]Positive control was vancomycin (FW: 1485). MIC obtained was 1.0 µg/ml
[e]Positive control was amoxicillin (FW: 365.4). MIC obtained was 0.06-0.12 µg/ml.
[f]Positive control does not exist

TABLE 9

In vitro antifungal activity of two bis-ammonium compounds (MICs in µg/ml and µM)

| Fungi | 1,12-bis(tributylammonium)dodecane (FW: 608.0) | | 1,16-bis(tributylammonium)hexadecane (FW: 664.0) | | Amphotericin B (FW: 924.1) | |
| --- | --- | --- | --- | --- | --- | --- |
| | µg/ml | µM | µg/ml | µM | µg/ml | µM |
| *Aspergillus fumigatus* ATCC 204 305 | 6.7 | 11 | 7.3 | 11 | 0.50 | 0.54 |
| *Aspergillus terreus* ATCC 03-232-378 | 3.3 | 5.5 | 7.3 | 11 | 1.0 | 1.1 |
| *Aspergillus flavus* ATCC 204 304 | 13.4 | 22 | 14.6 | 22 | 0.50 | 0.54 |
| *Scedosporium prolificans* 1-003-040 | 3.3 | 5.5 | 7.3 | 11 | 4.0 | 4.3 |

TABLE 9-continued

In vitro antifungal activity of two bis-ammonium compounds (MICs in µg/ml and µM)

| | 1,12-bis(tributylammonium)dodecane (FW: 608.0) | | 1,16-bis(tributylammonium)hexadecane (FW: 664.0) | | Amphotericin B (FW: 924.1) | |
|---|---|---|---|---|---|---|
| Fungi | µg/ml | µM | µg/ml | µM | µg/ml | µM |
| Scedosporium apiospermum 1-003-056 | 1.7 | 2.8 | 3.6 | 5.5 | 0.50 | 0.54 |
| Fusarium solani 04-132-4207 | 3.3 | 5.5 | 14.6 | 22 | 0.25 | 0.27 |
| Cryptococcus neoformans ATCC 90112 | 1.3 | 2.2 | 3.6 | 5.5 | 0.50 | 0.54 |
| Candida albicans ATCC 10231 | 2.6 | 4.4 | 7.2 | 11 | 0.50 | 0.54 |
| T. rubrum | 5.7 | 9.4 | nd | nd | N/A[a] | N/A[a] |
| T. tonsurans | 3.8 | 6.2 | nd | nd | N/A[a] | N/A[a] |
| M. gypseum | 3.8 | 6.3 | nd | nd | N/A[a] | N/A[a] |
| M. canis | 5.7 | 9.4 | nd | nd | N/A[a] | N/A[a] |

[a] The positve control for these dermatophytes was Itraconazole. It has MICs of 0.3 µg/ml for T. rubrum; 1.1 µg/ml for T. tonsurans; 0.9 µg/ml for M. gypseum and 0.6 µg/ml for M. canis.

Example 9

Susceptibility of Dermatophytes to Phospholipase Inhibitors

Isolates were tested using the method described in the National Committee for Clinical Laboratory Standards (NCCLS) document M38-P for filamentous fungi, with dermatophyte specific modifications described by Fernández-Torres et al, Current topics in Medical Mycology, 14-19 Feb. 1999.

Materials and Methods

Test Organisms

Five dermatophyte isolates were, namely; T. rubrum, T. mentagrophytes, T. tonsurans, M. canis and M. gypseum, all of which produce lipases and some, phospholipase. These isolates were tested by the broth microdilution method according to NCCLS document M38-P, for activity against selected antifungal agents. In addition, ten randomly selected isolates of T. tonsurans were also tested. All isolates were maintained on SDA at 28° C. Candida parapsilosis (ATCC 20019) was used as the reference control is organism.

Antifungal Compounds 1,12bis(Tributylammonium)dodecane,dibromide (VS1-32) below:

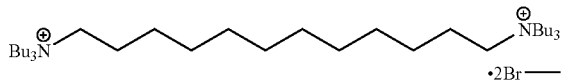

Itraconazole (ITRA) (Janssen, Cilag, Beerse, Belgium) and Terbinafine (TRB) (Novartis, Basel, Switzerland) were supplied by manufacturers as standard powders, and used as reference agents.

Broth Medium

The microdilution plates used were a single lot of RPMI 1640 basal medium (JRH bioScience Inc. Lenexa, Kans., USA) with L-glutamine and without sodium bicarbonate, buffered to pH 7.0, at 25° C., with 0.165 M (MOPS) morpholinepropanesulfonic acid (Sigma).

Broth Microdilution Procedure

Preparation of Stock Solution

Preparation of stock solution was performed according to the guidelines set out in NCCLS M38-P, with some modifications, or according to manufacturer's directions.

Powdered drugs were dissolved in 100% dimethyl sulfoxide (DMSO), at concentrations 100 times higher than the final test concentration. All compounds were prepared in 100% (DMSO). For ITRA and TRB, two-fold drug dilutions were prepared in 100% DMSO at 100 times the final concentration, followed by further dilution 1:50 in RPMI medium, to yield 2× the final strength required for the test.

Itraconazole 10,000 µg/ml solution was further diluted 1:10 to give 1:1000 concentration. Small aliquots of the drug were frozen at −70° C. On the day of testing, an aliquot was thawed and further diluted to make a 2× drug concentration of 32 µg/ml (e.g. 0.25 mg of 1:1000 drug solution in 7.56 ml of RPMI). Test range of concentrations for ITRA was 0.03 to 16 µg/ml. Terbinafine, 1000 µg/ml solution was also frozen in aliquots at −70° C. On the day of testing, it was further diluted 1:50 to give 20/g/ml concentration (e.g. 0.5 ml in 24.5 ml of RPMI). Finally, it was again diluted 1:10 to give 2 µg/ml concentration (e.g. 1 ml in 9 ml of RPMI). The range of concentrations tested for TRB was 0.0019 to 1 µg/ml.

The range of concentration for 1,12bis(Tributylammonium)dodecane,dibromide was 0.45 to 244 µg/ml Preparation of Fungal Inocula Fungal cultures were subcultured onto Potato Dextrose Agar and grown at 28° C. for 7-10 days. Fungal suspensions were covered with 5 ml of distilled water, and then colonies were scraped off with cotton tipped swabs. The resulting mixture of conidia and hyphae elements was withdrawn, transferred to a sterile tube and then vortexed with glass beads. After the particles settled, the upper homogeneous suspension was collected and its density adjusted by a densitometer to a 0.5 McFarland standard at the wavelength of 530 nm (80-85% transmittance). These stock suspensions were then diluted 1:50 with RPMI medium to obtain final working inoculum concentration ranging from $0.3 \times 10^4$ to $9 \times 10^4$ CFU/ml. Inoculum quantification was performed by plating 100 µl of the 1:1000 dilution of the adjusted inoculum on SDA plates, incubated at 28° C., and after 7 days of incubation, the colonies were counted.

Test Procedure

Testing was based on NCCLS M38-P document for testing filamentous moulds. Testing was carried out in sterile 96-well flat bottomed microtitre plate. Columns 1 and 3 to 12 were filled with 100 µl of RPMI medium, leaving column 2 unfilled. Columns 1, 2 and 3 were filled with 100 µl of 2× drug concentration. Serial dilutions were then made by transferring 100 µl from column 3 to each column up to column 11, and 100 µl from column 11 was discarded. Column 12 served as drug free growth control. Finally, 100 µl of inoculum suspension was added to all wells except column 1, which acted as sterility control (Columns 1 and 12 served as sterility and growth control respectively). Plates were incubated at 28°

C. for 7 days, and read at 3 days and 7 days of incubation. All testing was performed in duplicate, on three separate occasions.

Determination of MIC End Points

Growth in microtitre trays were read by visual inspection by using an illuminated-reversed mirror. Growth in each well was compared with the "growth control" drug free well. The MIC end point for all the drugs was chosen to be the first well with 100% growth inhibition (i.e. the lowest drug concentration inhibiting growth).

Results

The MICs ranges for ITRA were from 0.03 to 2.0 µg/ml, and from 0.007 to 0.25 µg/ml for TRB (Tables 10 and 11).

1,12-Bis(tributylammonium)dodecane,dibromide, VS1-32, had an MIC range of 1.9-7.6 µg/ml to $T.$ $tonsurans$ and $M.$ $gypseum$. The lowest GM was against $T.$ $tonsurans$. The highest GM had $M.$ $canis$ (Tables 10 and 11).

VS1-32 inhibits $Cryptococcus$ $neoformans$ H99 and $C.$ $albicans$ (ATCC10231) phospholipases, and has also fungicidal activity against those yeasts. In the present study, the mean MICs for VS1-32 were relatively high across all the isolates (2.625-7.61 µg/ml).

Example 10

Pharmaceutical Formulations

Antimicrobial compounds of the present invention may be administered alone, although they may also be administered as a pharmaceutical formulation. For instance, the active ingredient may comprise, for topical administration, from 0.001% to 10% by weight, and more typically from 1% to 5% by weight of the formulation, although it may comprise as much as 10% by weight.

By way of illustration, specific examples of pharmaceutical compositions in accordance with the present invention are outlined below. The following are to be construed as merely illustrative examples of formulations and not as a limitation of the scope of the present invention in any way.

TABLE 10

MIC values for selected antifungal compounds against dermatophyte isolates.

| Antifungal agent | MIC (µg/ml) | T. rubrum | T. mentagrophyte | T. tonsurans | M. gypseum | M. canis |
|---|---|---|---|---|---|---|
| ITRA | Range | 0.03-1.0 | 0.06-1.0 | 0.25-2.0 | 0.25-2.0 | 0.125-2.0 |
|  | Mean | 0.276 | 0.355 | 1.06 | 0.93 | 0.63 |
|  | GM | 0.171 | 0.260 | 0.84 | 0.74 | 0.42 |
| TRB | Range | 0.007-0.06 | 0.03-0.06 | 0.015-0.06 | 0.015-0.25 | 0.03 |
|  | Mean | 0.032 | 0.035 | 0.03 | 0.122 | 0.03 |
|  | GM | 0.026 | 0.034 | 0.024 | 0.077 | 0.03 |
| VS1-32 | Range | 3.8-7.6 | 3.8 | 1.9-7.6 | 1.9-7.6 | 3.8-7.6 |
|  | Mean | 5.7 | 3.8 | 3.8 | 4.75 | 6.33 |
|  | GM | 5.37 | 3.8 | 3.38 | 3.8 | 6.032. |

TABLE 11

MIC values for ten $T$ $tonsurans$ isolates

| Organism | MIC µg/ml | ITRA | TRB | VSI-32 |
|---|---|---|---|---|
| T. tonsurans 1 | Range | 0.03-0.125 | 0.015-0.06 | 1.9-3.8 |
|  | Mean | 0.21 | 0.037 | 3.17 |
|  | GM | 0.12 | 0.034 | 3.02 |
| T. tonsurans 2 | Range | 0.125-2.0 | 0.015-0.06 | 0.45-7.6 |
|  | Mean | 0.604 | 0.041 | 2.83 |
|  | GM | 0.397 | 0.036 | 1.15 |
| T.tonsurans 3 | Range | 0.06-0.5 | 0.015-0.125 | 0.45-3.8 |
|  | Mean | 0.27 | 0.051 | 2.68 |
|  | GM | 0.196 | 0.038 | 1.866 |
| T. tonsurans 4 | Range | 0.5 | 0.015-0.06 | 0.45-3.8 |
|  | Mean | 0.5 | 0.0275 | 2.68 |
|  | GM | 0.5 | 0.024 | 1.866 |
| T. tonsurans 5 | Range | 0.25-0.5 | 0.03-0.06 | 0.45-7.6 |
|  | Mean | 0.46 | 0.05 | 5.216 |
|  | GM | 0.44 | 0.048 | 2.96 |
| T. tonsurans 6 | Range | 0.25-2.0 | 0.03-0.125 | 0.45-15.25 |
|  | Mean | 0.96 | 0.071 | 6.94 |
|  | GM | 0.71 | 0.061 | 4.32 |
| T. tonsurans 7 | Range | 0.5-1.0 | 0.015-0.06 | 0.45-3.8 |
|  | Mean | 0.58 | 0.045 | 2.683 |
|  | GM | 0.56 | 0.038 | 1.866 |
| T. tonsurans 8 | Range | 0.25-2.0 | 0.06-0.125 | 0.45-3.8 |
|  | Mean | 1.08 | 0.07 | 3.13 |
|  | GM | 0.79 | 0.068 | 2.48 |
| T. tonsurans 9 | Range | 0.125-1.0 | 0.06-0.125 | 3.8-15.25 |
|  | Mean | 0.52 | 0.081 | 7.61 |
|  | GM | 0.445 | 0.077 | 6.039 |
| T. tonsurans 10 | Range | 0.25-1.0 | 0.015-0.06 | 3.8-7.6 |
|  | Mean | 0.5 | 0.035 | 4.75 |
|  | GM | 0.445 | 0.03 | 4.52 |

Example 10(a)

Topical Cream Composition

A typical composition for delivery as a topical cream is outlined below:
Compound of Formula (I) 1.0 g
Polawax GP 200 25.0 g
Lanolin Anhydrous 3.0 g
White Beeswax 4.5 g
Methyl hydroxybenzoate 0.1 g
Deionised & sterilised Water to 100.0 g The polawax, beeswax and lanolin are heated together at 60° C., a solution of methyl hydroxybenzoate is added and homogenisation achieved using high speed stirring. The temperature is then allowed to fall to 50° C. The compound of Formula (I) is then added and dispersed throughout, and the composition is allowed to cool with slow speed stirring.

Example 10(b)

Topical Lotion Composition

A typical composition for delivery as a topical lotion is outlined below:
Compound of Formula (I) 1.2 g
Sorbitan Monolaurate 0.8 g
Polysorbate 20 0.7 g Cetostearyl Alcohol 1.5 g
Glycerin 7.0 g
Methyl Hydroxybenzoate 0.4 g
Sterilised Water about to 100.00 ml The methyl hydroxybenzoate and glycerin are dissolved in 70 ml of the water at 75° C. The sorbitan monolaurate, polysorbate 20 and cetostearyl alcohol are melted together at 75° C. and added to the aqueous solution. The resulting emulsion is homogenised, allowed to cool with continuous stirring and the compound of Formula (I) is added as a suspension in the remaining water. The whole suspension is stirred until homogenised.

Example 10(c)

Eye Prop Composition

A typical composition for delivery as an eye drop is outlined below:
Compound of Formula (I) 0.3 g
Methyl Hydroxybenzoate 0.005 g
Propyl Hydroxybenzoate 0.06 g
Purified Water about to 100.00 ml.

The methyl and propyl hydroxybenzoates are dissolved in 70 ml purified water at 75° C., and the resulting solution is allowed to cool. The compound of Formula (I) is then added, and the solution sterilised by filtration through a membrane filter (0.22 µm pore size), and aseptically packed into sterile containers.

Example 10(d)

Aerosol Composition

For an aerosol container with a capacity of 20-30 ml: a mixture of 10 mg of a compound of Formula (I) with 0.5-0.8% by weight of a lubricating agent, such as polysorbate 85 or oleic acid, is dispersed in a propellant, such as freon, and put into an appropriate aerosol container for either intranasal or oral inhalation administration or topical application.

Example 10(e)

Composition for Parenteral Administration

A pharmaceutical composition of the present invention for intramuscular injection could be prepared to contain 1 mL sterile buffered water, and 1 mg of a compound of Formula (I). Similarly, a pharmaceutical composition for intravenous infusion may comprise 250 ml of sterile Ringer's solution, and 5 mg of a compound of Formula (I).

Example 10(f)

Capsule Composition

A pharmaceutical composition of a compound of Formula (I) in the form of a capsule may be prepared by filling a standard two-piece hard gelatin capsule with 50 mg of a compound of Formula (I), in powdered form, 100 mg of lactose, 35 mg of talc and 10 mg of magnesium stearate.

Example 10(g)

Injectable Parenteral Composition

A pharmaceutical composition of this invention in a form suitable for administration by injection may be prepared by mixing 1% by weight of a compound of Formula (I) in 10% by volume propylene glycol and water. The solution is sterilised by filtration.

Example 10(h)

Ointment Composition

A typical composition for delivery as an ointment includes 1.0 g of a compound of Formula (I), together with white soft paraffin to 100.0 g, dispersed to produce a smooth, homogeneous product.

Example 10(i)

Gel Composition

A percutaneous gel can be prepared as outlined below:
Compound of Formula (I) 1.0 g
Propylene glycol 5.0 g
Isopropyl alcohol 20.0 g
Carboxyvinyl polymer 2.0 g
Aqueous ammonia q.s.
Purified water 72.0 g The compound of Formula (I) is dissolved into a mixed solvent of propylene glycol and isopropyl alcohol. The Carboxyvinyl polymer is added to the solution after swelling in purified water. After stirring, the mixture is adjusted to pH 7 with the aqueous ammonia.

Example 10(j)

Powder Composition

A powder composition can be prepared by mixing 6.0 g of sodium caseinate, 3.0 g of xanthan gum and 60.0 g of water for 30 minutes at room temperature. To this aqueous phase 2.0 g of a compound of Formula (I) is added, while agitating the solution to form an emulsion, having a pH around 7. The emulsion is homogenized and dehydrated by heating the emulsion to form dry powder particles. The dried powder is then sieved to obtain fine powder particles of mesh size 120-180 µm.

The invention claimed is:

1. A bis-cationic compound comprising a bis-cation and an anion, wherein the bis-cation of the compound is of Formula (I)

$$R_2-\overset{\overset{R_1}{\oplus}}{\underset{R_3}{Y_1}}-C(R_7R_{7'})-(A)-C(R_8R_{8'})-\overset{\overset{R_4}{\oplus}}{\underset{R_6}{Y_2}}-R_5 \quad (I)$$

wherein:
(1) $Y_1$ and $Y_2$ may be the same or different and are independently selected from N and P;
$R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted aralkyl, optionally substituted heteroaryl, and optionally substituted heterocycloalkyl, wherein said substituents are independently selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy$C_{1-6}$ alkyl, aryl, $OC(O)Ph$, and $=C(Ph)_2$; or $R_1$ and $R_2$ together with the $Y_1$ group to which they are attached, or $R_1$, $R_2$ and $R_3$ together with the $Y_1$ group to which they are attached may optionally form a heterocycloalkyl group; and $R_4$ and $R_5$ together with the $Y_2$ group to which they are attached, or $R_4$, $R_5$ and $R_6$ together with the $Y_2$ group to which they are attached may optionally form a heterocycloalkyl group; wherein each of said heterocycloalkyl groups may be optionally substituted with one or more groups selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy $C_{1-6}$ alkyl, aryl, $OC(O)Ph$, and $=C(Ph)_2$;

$R_7$, $R_{7'}$, $R_8$ and $R_{8'}$ may be the same or different and are independently selected from hydrogen, F and Cl;

A comprises one or more groups selected from optionally substituted alkylene, optionally substituted alkenylene, optionally substituted alkynylene, optionally substituted phenyl, optionally substituted $C_{5-7}$ cycloalkyl, and —C(O)—, wherein the length of A is from 5 to 18 carbon atoms, and wherein the substituents are independently selected from $C_{1-6}$ alkyl, $C_{2-6}$ alkenyl, $C_{2-6}$ alkynyl, hydroxyl, halogen, $NO_2$, $C(O)R_{10}$, $OR_{11}$, $CH_2OR_{11}$, $CH_2NR_{12}R_{13}$, $SR_{11}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, and optionally substituted aralkyl, wherein said optional substituents are independently selected from $C_{1-4}$ alkyl, hydroxyl and halogen;

$R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aralkyl, optionally substituted alkylheteroaryl, wherein said substituents are independently selected from $C_{1-4}$ alkyl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-4}$ alkyl, hydroxyl, halogen, amino, and $C(O)OR_{11}$;

and when $Y_1=Y_2=N$, A comprises one or more groups selected from substituted alkylene, substituted alkenylene, substituted alkynylene, substituted phenyl, substituted $C_{5-7}$ cycloalkyl, and —C(O)—, wherein the length of A is from 5 to 18 carbon atoms, and wherein the substituents are independently selected from $C_4$-$C_6$ alkyl, $C_{4-6}$ alkenyl, $C_{4-6}$ alkynyl, hydroxyl, halogen, $NO_2$, $C(O)R_{10}$, $OR_{11}$, $CH_2OR_{11}$, $CH_2NR_{12}R_{13}$, $SR_{11}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, and optionally substituted aralkyl, wherein said optional substituents are independently selected from $C_{1-4}$ alkyl, hydroxyl and halogen;

$R_{12}$ and $R_{13}$ are independently selected from the group consisting of hydrogen, optionally substituted $C_{1-10}$ alkyl optionally substituted $C_{2-10}$ alkenyl, optionally substituted $C_{2-10}$ alkynyl, optionally substituted $C_{3-10}$ cycloalkyl, optionally substituted aralkyl, optionally substituted alkylheteroaryl, wherein said substituents are independently selected from $C_{1-4}$ alkyl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-4}$ alkyl, hydroxyl, halogen, amino, and $C(O)OR_{11}$;

and when $Y_1=Y_2=P$, A comprises one or more groups selected from substituted alkylene, substituted alkenylene, substituted alkynylene, substituted phenyl, substituted $C_{5-7}$ cycloalkyl, and —C(O)—, wherein the length of A is from 5 to 18 carbon atoms, and wherein the substituents are independently selected from $C_{1-6}$ alkyl, $C_{2-6}$ alkenyl, $C_{2-6}$ alkynyl, hydroxyl, halogen, $NO_2$, $C(O)R_{10}$, $OR_{11}$, $CH_2OR_{11}$, $CH_2NR_{12}R_{13}$, $SR_{11}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, and optionally substituted aralkyl, wherein said optional substituents are independently selected from $C_{1-4}$ alkyl, hydroxyl and halogen;

$R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aralkyl, optionally substituted alkylheteroaryl, wherein said substituents are independently selected from $C_{1-4}$ alkyl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-4}$ alkyl, hydroxyl, halogen, amino, and $C(O)OR_{11}$;

and when A is —$CH_2$—$C(O)PhCH_2CH_2$-Ph-C(O)—$CH_2$—, and $R_1$ and $R_4$ are hydroxy substituted ethyl, then one of $R_2$, $R_3$, $R_5$ and $R_6$ is different;

or:

(2) $Y_1$ and $Y_2$ may be the same or different and are independently selected from N and P;

$R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted aralkyl, optionally substituted heteroaryl, and optionally substituted heterocycloalkyl wherein said substituents are independently selected from $C_{1-6}$ alkyl $C_{2-6}$ alkenyl, $C_{2-6}$ alkynyl, hydroxyl, halogen, $O(C_{1-6}$ alkyl) $C(O)O(C_{1-6}$ alkyl), $OC(O)(C_{1-6}$ alkyl), $NO_2$, amino, hydroxy$C_{1-6}$ alkyl, aryl, $OC(O)Ph$, and $=C(Ph)_2$; or $R_1$ and $R_2$ together with the $Y_1$ group to which they are attached, or $R_1$, $R_2$ and $R_3$ together with the $Y_1$ group to which they are attached may optionally form a heterocycloalkyl group; and $R_4$ and $R_5$ together with the $Y_2$ group to which they are attached, or $R_4$, $R_5$ and $R_6$ together with the $Y_2$ group to which they are attached may optionally form a heterocycloalkyl group; wherein each of said heterocycloalkyl groups may be optionally substituted with one or more groups selected from $C_{1-6}$ alkyl, $C_{2-6}$ alkenyl $C_{2-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy $C_{1-6}$ alkyl, aryl, $OC(O)Ph$, and $=C(Ph)_2$;

$R_7$, $R_{7'}$, $R_8$ and $R_{8'}$ may be the same or different and are independently selected from F and Cl;

A comprises one or more groups selected from optionally substituted alkylene, optionally substituted alkenylene, optionally substituted alkynylene, optionally substituted phenyl, optionally substituted $C_{5-7}$ cycloalkyl, and —C(O)—, wherein the length of A is from 5 to 18 carbon atoms, and wherein the substituents are independently selected from $C_{1-6}$ alkyl, $C_{2-6}$ alkenyl, $C_{2-6}$ alkynyl, hydroxyl, halogen, $NO_2$, $C(O)R_{10}$, $OR_{11}$, $CH_2OR_{11}$, $CH_2NR_{12}R_{13}$, $SR_{11}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, and optionally substituted aralkyl, wherein said optional substituents are independently selected from $C_{1-4}$ alkyl, hydroxyl and halogen;

$R_{12}$ and $R_{13}$ are independently selected from the group consisting of hydrogen, optionally substituted $C_{1-10}$ alkyl, optionally substituted $CO_{2-10}$ alkenyl, optionally substituted $C_{2-10}$ alkynyl, optionally substituted $C_{3-10}$ cycloalkyl, optionally substituted aralkyl, optionally substituted alkylheteroaryl, wherein said substituents are independently selected from $C_{1-4}$ alkyl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-4}$ alkyl, hydroxyl, halogen, amino, and $C(O)OR_{11}$;

or:

(3) $Y_1$ and $Y_2$ are both nitrogen;

$R_1$ to $R_6$ may be the same or different and are independently selected from the group consisting of substituted $C_{1-10}$ alkyl, substituted $C_{2-10}$ alkenyl, substituted $C_{2-10}$ alkynyl, substituted $C_{3-10}$ cycloalkyl, substituted aryl, substituted aralkyl, optionally substituted heteroaryl, and optionally substituted heterocycloalkyl, wherein said substituents are independently selected from $C_{4-6}$ alkyl, $C_{4-6}$ alkenyl, $C_{4-6}$ alkynyl, hydroxyl, $O(C_{1-6}$ alkyl), $C(O)O(C_{1-6}$ alkyl), $OC(O)(C_{1-6}$ alkyl), $NO_2$, amino, hydroxy$C_{1-6}$ alkyl, aryl, $OC(O)Ph$, and $=C(Ph)_2$;

$R_7$, $R_{7'}$, $R_8$ and $R_{8'}$ may be the same or different and are independently selected from hydrogen, F and Cl;

$R_1$ and $R_2$ together with the $Y_1$ group to which they are attached, or $R_1$, $R_2$ and $R_3$ together with the $Y_1$ group to which they are attached may optionally form a heterocycloalkyl group; and $R_4$ and $R_5$ together with the $Y_2$ group to which they are attached, or $R_4$, $R_5$ and $R_6$ together with the $Y_2$ group to which they are attached may optionally form a heterocycloalkyl group; wherein each of said heterocycloalkyl groups may be optionally substituted with one or more groups selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy $C_{1-6}$ alkyl, aryl, $OC(O)Ph$, and $=C(Ph)_2$;

A comprises one or more groups selected from optionally substituted alkylene, optionally substituted alkenylene, optionally substituted alkynylene, optionally substituted phenyl, optionally substituted $C_{5-7}$ cycloalkyl, and —C(O)—, wherein the length of A is from 5 to 18 carbon atoms, and wherein the substituents are independently selected from $C_{1-6}$ alkyl, $C_{2-6}$ alkenyl, $C_{2-6}$ alkynyl, hydroxyl, halogen, $NO_2$, $C(O)R_{10}$, $OR_{11}$, $CH_2OR_{11}$, $CH_2NR_{12}R_{13}$, $SR_{11}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, and optionally substituted aralkyl, wherein said optional substituents are independently selected from $C_{1-4}$ alkyl, hydroxyl and halogen;

$R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aralkyl, optionally substituted alkylheteroaryl, wherein said substituents are independently selected from $C_{1-4}$ alkyl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-4}$ alkyl, hydroxyl, halogen, amino, and $C(O)OR_{11}$;

wherein when —$C(R_7R_{7'})$-(A)-$(CR_8R_{8'})$— is 9, 10, 11 or 12 alkylene groups and when $R_1$, $R_2$ and $Y_1$ form a heterocycloalkyl group and when $R_4$, $R_5$, and $Y_2$ form a heterocycloalkyl group, then $R_3$ and $R_6$ are different; and wherein when —$C(R_7R_{7'})$-(A)-$(CR_8R_{8'})$— is 9, 10 or 12 alkylene groups and $R_1$, $R_2$, $R_3$ and $Y_1$ form a bicyclic group, then $R_1$, $R_2$, $R_3$ and $Y_1$ together are different to $R_4$, $R_5$, $R_6$ and $Y_2$ when taken together;

or:

(4) $Y_1$ and $Y_2$ are both nitrogen, $R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted aralkyl, optionally substituted heteroaryl, and optionally substituted heterocycloalkyl, wherein said substituents are independently selected from $C_{1-6}$ alkyl, $C_{2-6}$ alkenyl, $C_{2-6}$ alkynyl, halogen, $O(C_{1-6}$ alkyl), $C(O)O(C_{1-6}$ alkyl), $OC(O)(C_{1-6}$ alkyl), $NO_2$, amino, hydroxy$C_{1-6}$ alkyl, aryl, $OC(O)Ph$, and $=C(Ph)_2$; or $R_1$ and $R_2$ together with the $Y_1$ group to which they are attached, or $R_1$, $R_2$ and $R_3$ together with the $Y_1$ group to which they are attached may optionally form a heterocycloalkyl group; and $R_4$ and $R_5$ together with the $Y_2$ group to which they are attached, or $R_4$, $R_5$ and $R_6$ together with the $Y_2$ group to which they are attached may optionally form a heterocycloalkyl group; wherein each of said heterocycloalkyl groups may be optionally substituted with one or more groups selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl) $OC(O)(C_{1-6}$ alkyl), $NO_2$, amino, hydroxy $C_{1-6}$ alkyl, aryl, $OC(O)Ph$, and $=C(Ph)_2$;

$R_7$, $R_{7'}$, $R_8$ and $R_{8'}$ may be the same or different and are independently selected from hydrogen, F and Cl;

A comprises one or more groups selected from optionally substituted alkylene, optionally substituted alkenylene, optionally substituted alkynylene, optionally substituted phenyl, optionally substituted $C_{5-7}$ cycloalkyl, and —C(O)—, wherein the length of A is from 5 to 18 carbon atoms, and wherein the substituents are independently selected from $C_{1-6}$ alkyl, $C_{2-6}$ alkenyl, $C_{2-6}$ alkynyl, hydroxyl, halogen, $NO_2$, $C(O)R_{10}$, $OR_{11}$, $CH_2OR_{11}$, $CH_2NR_{12}R_{13}$, $SR_{11}$, $NR_{12}R_-$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, and optionally substituted aralkyl, wherein said optional substituents are independently selected from $C_{1-4}$ alkyl, hydroxyl and halogen;

$R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aralkyl, optionally substituted alkylheteroaryl, wherein said substituents are independently selected from $C_{1-4}$ alkyl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-4}$ alkyl, hydroxyl, halogen, amino, and $C(O)OR_{11}$;

wherein when —$C(R_7R_{7'})$-(A)-$(CR_8R_{8'})$— is 12 alkylene groups, one of $R_1$ to $R_6$ is different; and wherein when —$C(R_7R_{7'})$-(A)-$(CR_8R_{8'})$— is 10 alkylene groups and four of $R_1$ to $R_6$ are $C_{1-3}$alkyl, the remaining two of $R_1$ to $R_6$ are different; and wherein when —$C(R_7R_{7'})$-(A)-$(CR_8R_{8'})$— is 9, 10, 11 or 12 alkylene groups and when $R_1$, $R_2$ and $Y_1$ form a heterocycloalkyl group and when $R_4$, $R_5$ and $Y_2$ form a heterocycloalkyl group, then $R_3$ and $R_6$ are different; and wherein when —$C(R_7R_{7'})$-(A)-$(CR_8R_{8'})$— is 9, 10 or 12 alkylene groups and $R_1$, $R_2$, $R_3$ and $Y_1$ form a bicyclic group, then $R_1$, $R_2$, $R_3$ and $Y_1$ together are different to $R_4$, $R_5$, $R_6$ and $Y_2$ when taken together;

or:

(5) $Y_1$ and $Y_2$ are both nitrogen:

$R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted aralkyl, optionally substituted heteroaryl, and optionally substituted heterocycloalkyl, wherein said substituents are independently selected from $C_{4-6}$ alkyl $C_{2-6}$ alkenyl, $C_{2-6}$ alkyl, hydroxyl, halogen, $O(C_{1-6}$ alkyl), $C(O)O(C_{1-6}$ alkyl), $OC(O)(C_{1-6}$ alkyl), $NO_2$, amino, hydroxy$C_{1-6}$ alkyl, aryl, $OC(O)Ph$, and $=C(Ph)_2$; or $R_1$ and $R_2$ together with the $Y_1$ group to which they are attached, or $R_1$, $R_2$ and $R_3$ together with the $Y_1$ group to which they are attached may optionally form a heterocycloalkyl group; and $R_4$ and $R_5$ together with the $Y_2$ group to which they are attached, or $R_4$, $R_5$ and $R_6$ together with the $Y_2$ group to which they are attached may optionally form a heterocycloalkyl group; wherein each of said heterocycloalkyl groups is substituted with one or more groups selected from $C_{4-6}$ alkyl, $C_{4-6}$ alkenyl, $C_{4-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy $C_{4-6}$ alkyl, aryl, $OC(O)Ph$, and $=C(Ph)_2$;

$R_7$, $R_{7'}$, $R_8$ and $R_{8'}$ may be the same or different and are independently selected from hydrogen, F and Cl;

A comprises one or more groups selected from optionally substituted alkylene, optionally substituted alkenylene, optionally substituted alkynylene, optionally substituted phenyl, optionally substituted $C_{5-7}$ cycloalkyl, and —C(O)—, wherein the length of A is from 5 to 18 carbon atoms, and wherein the substituents are independently selected from $C_{1-6}$ alkyl, $C_{2-6}$ alkenyl, $C_{2-6}$ alkynyl, hydroxyl, halogen, $NO_2$, $C(O)R_{10}$, $OR_{11}$, $CH_2R_{12}NR_{13}$, $SR_{11}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, and optionally substituted aralkyl, wherein said optional substituents are independently selected from $C_{1-4}$ alkyl, hydroxyl and halogen;

$R_{12}$ and $R_{13}$ are independently selected from the group consisting of hydrogen, optionally substituted $C_{1-10}$ alkyl optionally substituted $C_{2-10}$ alkenyl, optionally substituted $C_{2-10}$ alkynyl, optionally substituted $C_{3-10}$ cycloalkyl, optionally substituted aralkyl, optionally substituted alkylheteroaryl, wherein said substituents are independently selected from $C_{1-4}$ alkyl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-4}$ alkyl, hydroxyl, halogen, amino, and $C(O)OR_{11}$;

wherein when —$C(R_7R_{7'})$-(A)-$(CR_8R_{8'})$— is 12 alkylene groups, one of $R_1$ to $R_6$ is different; and wherein when —$C(R_7R_{7'})$-(A)-$(CR_8R_{8'})$— is 10 alkylene groups and four of $R_1$ to $R_6$ are $C_{1-3}$ alkyl, the remaining two of $R_1$ to $R_6$ are different; and wherein when —$C(R_7R_{7'})$-(A)-$(CR_8R_{8'})$— is 9, 10 or 12 alkylene groups and $R_1$, $R_2$, $R_3$ and $Y_1$ form a bicyclic group, then $R_1$, $R_2$, $R_3$ and $Y_1$ together are different to $R_4$, $R_5$, $R_6$ and $Y_2$ when taken together;

or:

(6) $Y_1$ and $Y_2$ are both P:

$R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted aralkyl, optionally substituted heteroaryl, and optionally substituted heterocycloalkyl, wherein said substituents are independently selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy$C_{1-6}$ alkyl aryl, $OC(O)Ph$, and $=C(Ph)_2$; wherein at least one of $R_1$ to $R_6$ is substituted; or $R_1$ and $R_2$ together with the $Y_1$ group to which they are attached, or $R_1$, $R_2$ and $R_3$ together with the $Y_1$ group to which they are attached may optionally form a heterocycloalkyl group; and $R_4$ and $R_5$ together with the $Y_2$ group to which they are attached, or $R_4$, $R_5$ and $R_6$ together with the $Y_2$ group to which they are attached may optionally form a heterocycloalkyl group; wherein each of said heterocycloalkyl groups may be optionally substituted with one or more groups selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy $C_{1-6}$ alkyl, aryl $OC(O)Ph$, and $=C(Ph)_2$;

$R_7$, $R_{7'}$, $R_8$ and $R_{8'}$ may be the same or different and are independently selected from hydrogen, F and Cl;

A comprises one or more groups selected from optionally substituted alkylene, optionally substituted alkenylene, optionally substituted alkynylene, optionally substituted phenyl, optionally substituted $C_{5-7}$ cycloalkyl, and —C(O)—, wherein the length of A is from 5 to 18 carbon atoms, and wherein the substituents are independently selected from $C_{1-6}$ alkyl, $C_{2-6}$ alkenyl, $C_{2-6}$ alkynyl, hydroxyl, halogen, $NO_2$, $C(O)R_{10}$, $OR_{11}$, $CH_2OR_{11}$, $CH_2NR_{12}R_{13}$, $SR_{11}$, $NR_{12}R_-$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $CO_{2-10}$ alkenyl, optionally substituted $C_{2-10}$ alkynyl, optionally substituted $C_{3-10}$ cycloalkyl, optionally substituted aryl, and optionally substituted aralkyl, wherein said optional substituents are independently selected from $C_{1-4}$ alkyl, hydroxyl and halogen;

$R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aralkyl, optionally substituted alkylheteroaryl, wherein said substituents are independently selected from $C_{1-4}$ alkyl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-4}$ alkyl, hydroxyl, halogen, amino, and $C(O)OR_{11}$;

provided that the bis-cation of formula (I) is not selected from the following:

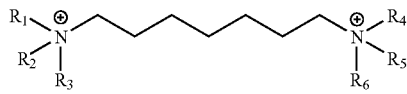
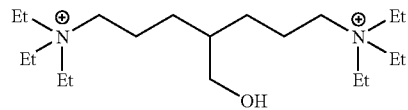

R1 = R2 = R3 = R4 = R5 = R6 = Me, Et,
R1 = R2 = R4 = R5 = Me, R3 = R6 = Et, Pr
R1 = R2 = R4 = R5 = Et, R3 = R6 = Me
R1 = R2 = R4 = R5 = Pr, R3 = R6 = Me
R1 = R2 = R4 = R5 = allyl, R3 = R6 = Me

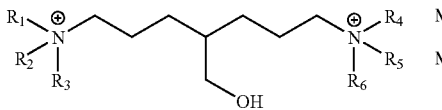
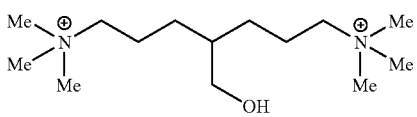

R1 = R2 = R4 = R5 = Me, R3 = R6 = Pr
R1 = R2 = R4 = R5 = Pr, R3 = R6 = Me

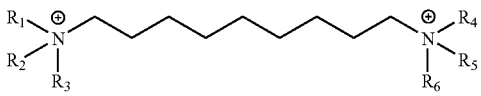
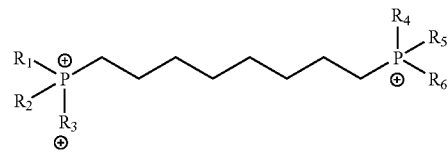

R1 = R2 = R3 = R4 = R5 = R6 = Me, Et, Pr, Bu, pentyl, allyl
R1 = R2 = R4 = R5 = Me, R3 = R6 = Pr, Bu, Decyl
R1 = R4 = Me, R2 = R3 = R5 = R6 = Hexyl, allyl
R1 = R4 = Me, R2 = R5 = Bu, R3 = R6 = octyl R1 = R2 = R3 = R4 = R5 = R6 = n-Bu, t-Bu, octyl

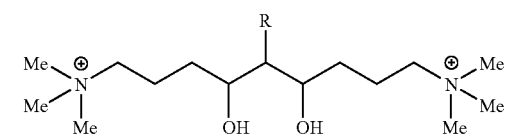

R1 = R2 = R3 = R4 = R5 = Me, Et, allyl
R1 = R2 = R4 = R5 = Me, R3 = R6 = Pr, pentyl
R1 = R2 = R4 = R5 = allyl, R3 = R6 = Et R = Pr, H, pentyl, hexyl, butyl, Me, Et -continued

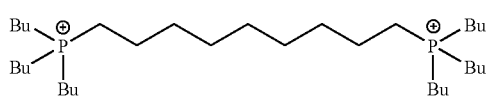

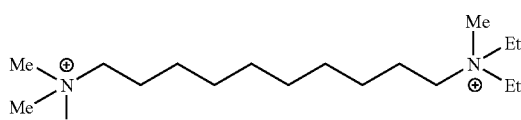

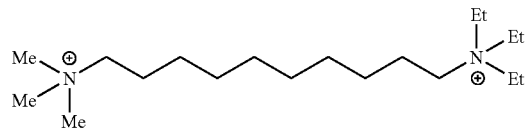

R1 = R2 = R3 = R4 = R5 = R6 = Me, Pr, pentyl, butyl, allyl, ethyl, hexyl
R1 = R2 = R3 = R4 = R5 = R6 = Bu, Et, hexyl, heptyl, pentyl, propyl, decyl, i-Pr, octyl
R1 = R4 = Me, R2 = R3 = R5 = R6 = allyl, ethyl
R1 = R2 = R4 = R5 = Et, R3 = R6 = hexyl

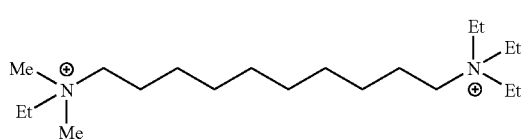

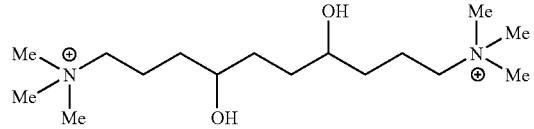

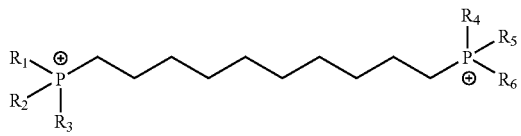

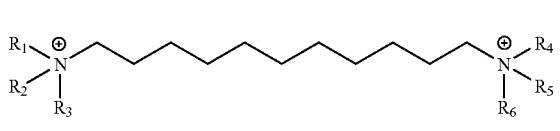

R1 = R2 = R3 = R4 = R5 = R6 = Me, Et, Bu, octyl

R1 = R2 = R3 = R4 = R5 = R6 = Me, Et
R1 = R2 = R4 = R5 = Me, R3 = R6 = pentyl

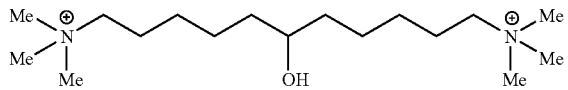

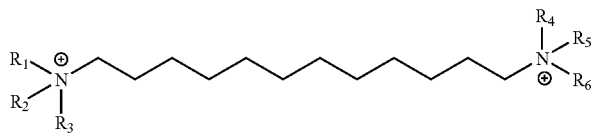

R1 = R2 = R3 = R4 = R5 = R6 = Bu, Et, Pr
R1 = R2 = R4 = R5 = Me, R3 = R6 = Bu, Et, heptyl, nonyl,
R1 = R2 = R4 = R5 = allyl, R3 = R6 = Me, Et
R1 = R2 = R4 = R5 = hexyl, R3 = R6 = Me

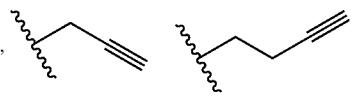

R1 = R2 = R3 = R4 = R5 = R6 = octyl, butyl

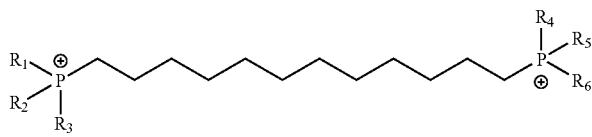

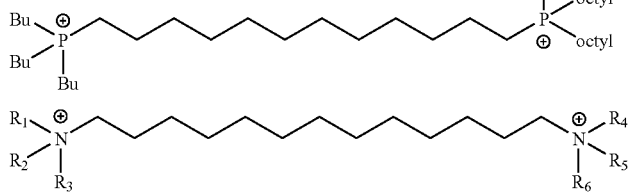

R1 = R2 = R3 = R4 = R5 = R6 = Me, Et

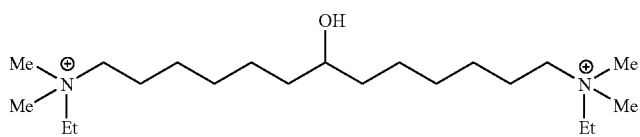

-continued
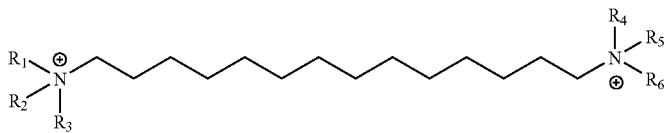
R1 = R2 = R3 = R4 = R5 = R6 = Me, Et, Pr
R1 = R2 = R4 = R5 = Me, R3 = R6 =
R1 = R4 = Me, R2 = R5 = Et, R3 = R6 = Pr
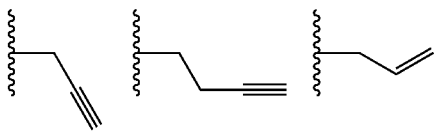
R1 = R2 = R3 = R4 = R5 = R6 = Et
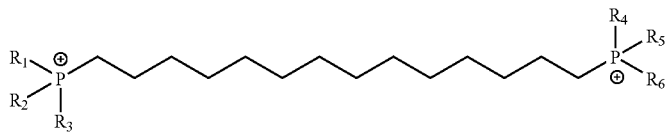
R1 = R2 = R3 = R4 = R5 = R6 = Me, Et, Bu
R1 = R4 = Me, R2 = R5 = Et, R3 = R6 = Pr
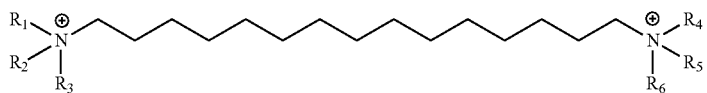
R1 = R2 = R3 = R4 = R5 = R6 = Me, Et, Pr, allyl
R1 = R2 = R4 = R5 = Me, R3 = R6 = Et
R1 = R2 = R4 = R5 = Et, R3 = R6 = Me
R1 = R4 = Me, R2 = R5 = Et, R3 = R6 = Pr
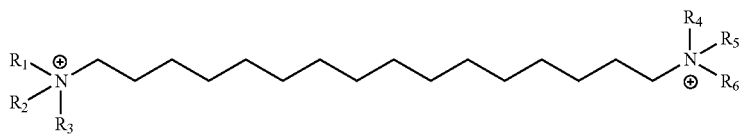
R1 = R2 = R3 = R4 = R5 = R6 = Et
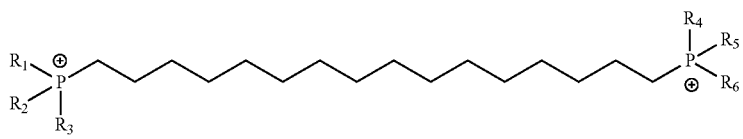
R1 = R2 = R3 = R4 = R5 = R6 = Me, Et
R1 = R4 = Me, R2 = R5 = Et, R3 = R6 = Pr
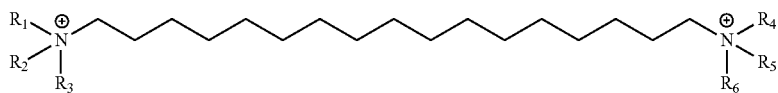
R1 = R2 = R3 = R4 = R5 = R6 = Me, Et
R1 = R2 = R4 = R5 = Et, R3 = R6 = Me
R1 = R4 = Me, R2 = R5 = Et, R3 = R6 = Pr
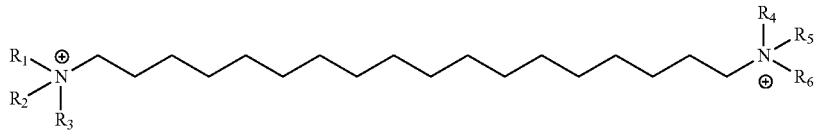
R1 = R2 = R3 = R4 = R5 = R6 = Me, Et
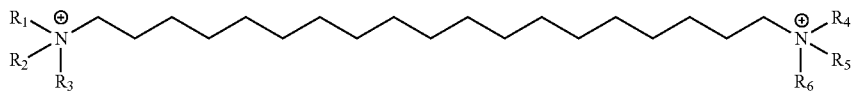

-continued
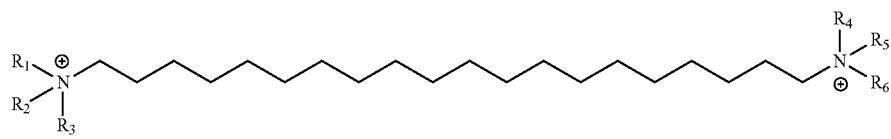
R1 = R2 = R3 = R4 = R5 = R6 = Me, Et, Pr
R1 = R4 = Me, R2 = R5 = Et, R3 = R6 = Pr
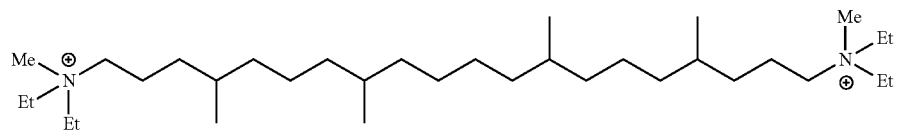
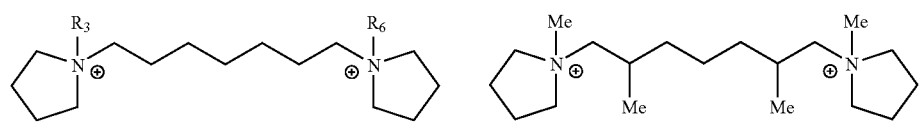
R3 = R6 = Me, Bu
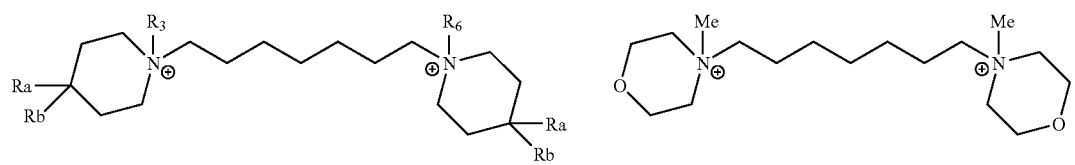
R3 = R6 = Me; Ra, Rb = H
R3 = R6 = Me, Ra = Ph, Rb = CO2Et
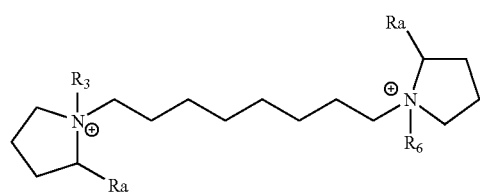
R3 = R6 = Me, Ra = H
R3 = R6 = Me, Ra = Me
R3 = R6 = Me, Ra = Et
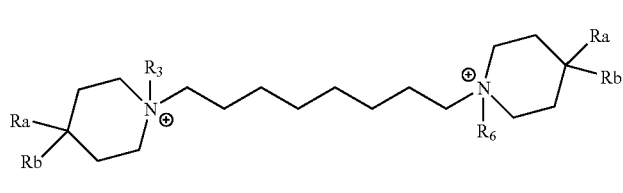
R3 = R6 = Me, Ra = Ph, Rb = CO2Et
R3 = R6 = Me, Ra, Rb = CPh2
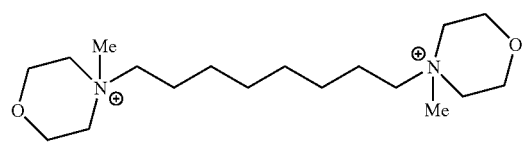
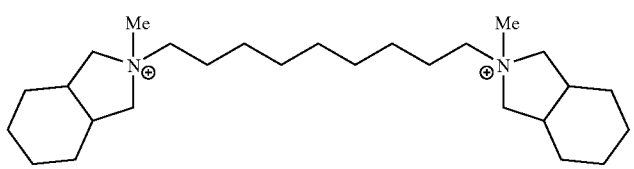
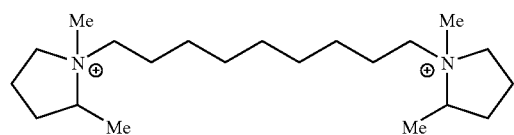
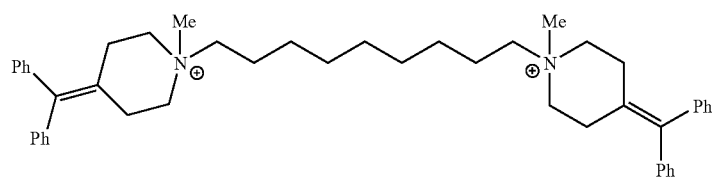

-continued
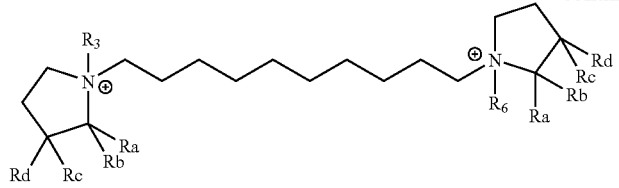
R3 = R6 = Me, Ra, Rb, Rc, Rd = H
R3 = R6 = Me, Ra = Me, Rb, Rc, Rd = H
R3 = R6 = Ra = Rb = Rc = Rd = Me
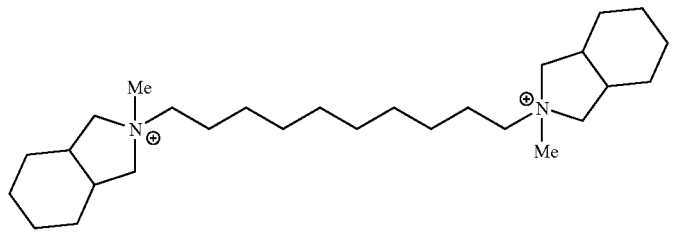
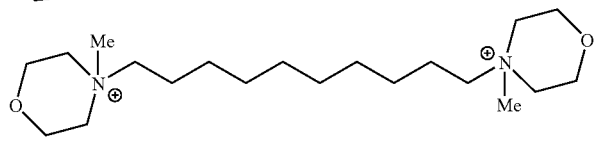
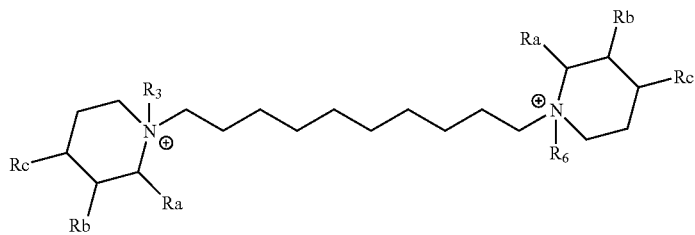
R3 = R6 = Me, Ra = Me, Rb = Rc = H
R3 = R6 = Me, Ra = Et, Rb = Rc = H
R3 = R6 = Et, Ra = H, Rb = OH, Rc = H
R3 = R6 = Me, Ra = Rb = Rc = H
R3 = R6 = Me, Ra = Rb = Rc = H
R3 = R6 = Me, Ra = H, Rb = OC(=O)Pr, Rc = H
R3 = R6 = Me, Ra = H, Rb = OAc, Rc = H
R3 = R6 = Me, Ra = Rb = H, Rc = OC(O)Ph
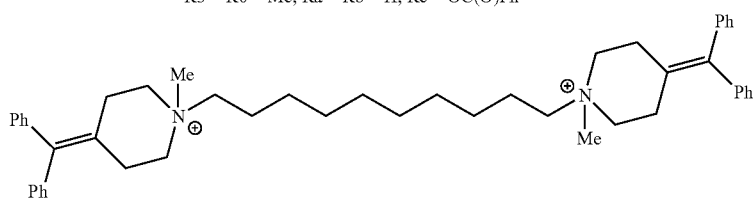
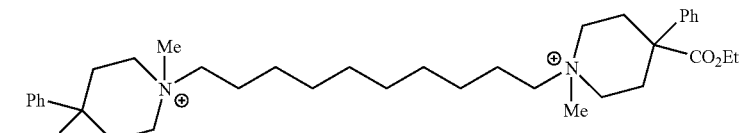
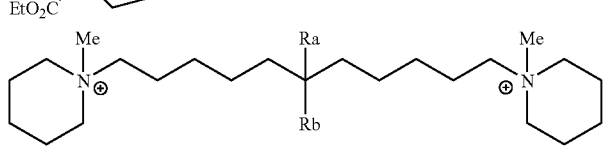
Ra, Rb = H
Ra = Me, Rb = Et
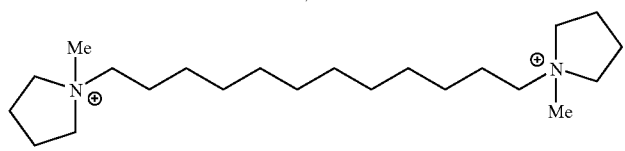

-continued
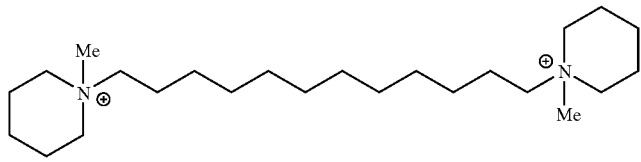
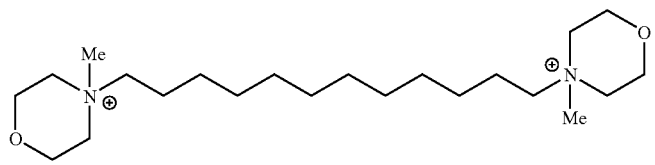
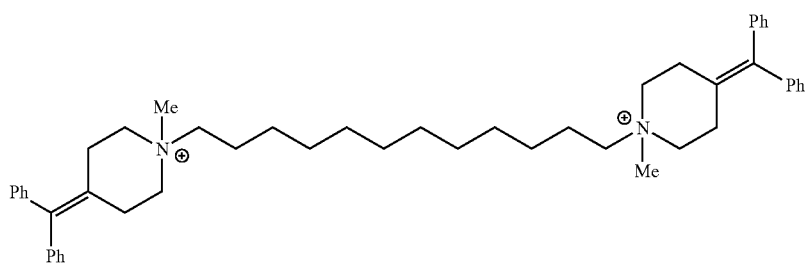
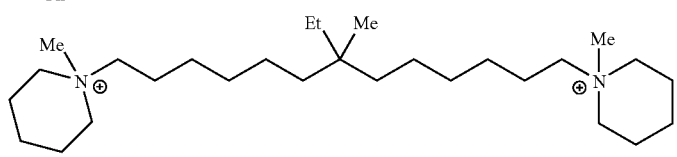
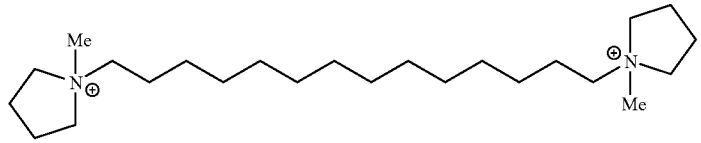
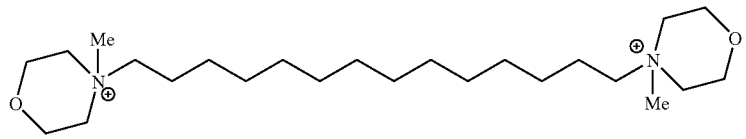
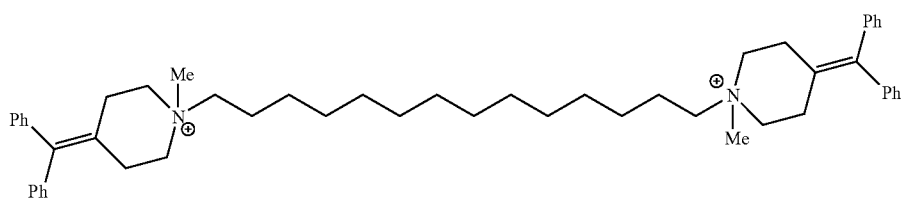
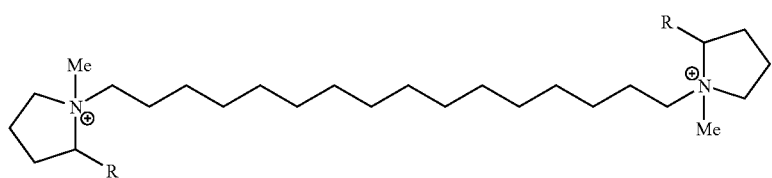
R = H, CH2OH
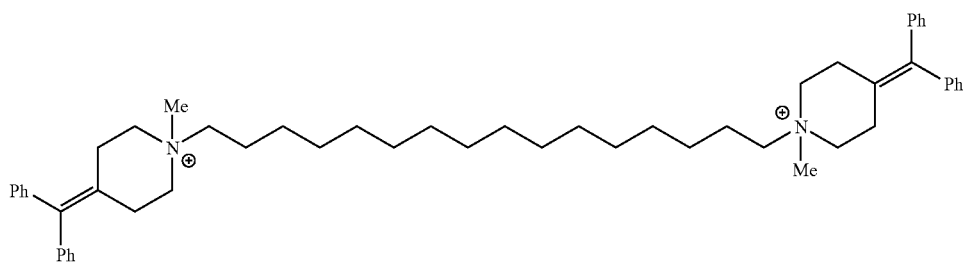

-continued

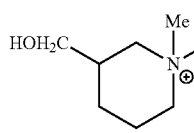
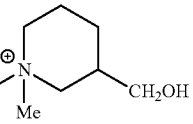
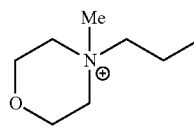

2. A compound according to claim 1, wherein $Y_1$ and $Y_2$ are each N.

3. A compound according to claim 1, wherein $Y_1$ and $Y_2$ are different.

4. A compound according to claim 1, wherein $R_1$ to $R_6$ are independently selected from the group consisting of optionally substituted $C_{1-10}$ alkyl, optionally substituted $C_{1-10}$ alkylene, optionally substituted aryl, and optionally substituted heterocycloalkyl, or $R_1$ and $R_2$ together with the $Y_1$ group to which they are attached, or $R_1$, $R_2$ and $R_3$ together with the $Y_1$ group to which they are attached form a heterocycloalkyl group; and $R_4$ and $R_5$ together with the $Y_2$ group to which they are attached, or $R_4$, $R_5$ and $R_6$ together with the $Y_2$ group to which they are attached form a heterocycloalkyl group;

wherein said optional substituents are independently selected from $C_{1-6}$ alkyl, $C_{2-6}$ alkenyl, $C_{2-6}$ alkynyl, hydroxyl, halogen, $O(C_{1-6}$ alkyl), $C(O)O(C_{1-6}$ alkyl), $OC(O)(C_{1-6}$ alkyl), $NO_2$, amino, hydroxy $C_{1-6}$ alkyl, and aryl.

5. A compound according to claim 1, wherein A comprises one or more groups selected from optionally substituted alkylene, optionally substituted alkenylene, optionally substituted phenyl, and —C(O)—, wherein the substituents are independently selected from $C_{1-6}$ alkyl, $C_{2-6}$ alkenyl, hydroxyl, halogen, $NO_2$, $C(O)R_{10}$, $OR_{11}$, $CH_2OR_{11}$, $CH_2NR_{12}R_{13}$, $SR_{11}$, $NR_{12}R_{13}$, $CONR_{12}R_{13}$, amino acids, dipeptidyl, tripeptidyl, tetrapeptidyl and pentapeptidyl.

6. A compound according to claim 1, wherein the length of A is from 5 to 9 carbon atoms.

7. A compound according to claim 1, wherein the biscation of the compound is of Formula (Ia):

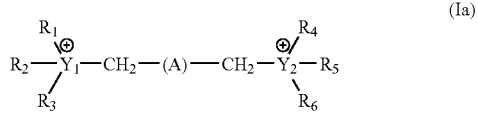

wherein $Y_1$ and $Y_2$ may be the same or different and are independently selected from N and P;

$R_1$ to $R_6$ may be the same or different and are independently selected from the group consisting of optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted aryl, optionally substituted heteroaryl, and optionally substituted heterocycloalkyl, wherein said substituents are independently selected from $C_{1-6}$ alkyl, $C_{2-6}$ alkenyl, hydroxyl, halogen, $O(C_{1-6}$ alkyl), $C(O)O(C_{1-6}$ alkyl), $NO_2$, amino, hydroxy $C_{1-6}$ alkyl, aryl, and $OC(O)Ph$; or $R_1$ and $R_2$ together with the $Y_1$ group to which they are attached may optionally form a heterocycloalkyl group; and $R_4$ and $R_5$ together with the $Y_2$ group to which they are attached may optionally form a heterocycloalkyl group; wherein each of said heterocycloalkyl groups may be optionally substituted with one or more groups selected from $C_{1-6}$ alkyl, $C_{2-6}$ alkenyl, hydroxyl, halogen, $O(C_{1-6}$ alkyl), $C(O)O(C_{1-6}$ alkyl), amino, hydroxy $C_{1-6}$ alkyl, and aryl;

A comprises one or more groups selected from optionally substituted alkylene, optionally substituted alkenylene, and optionally substituted phenyl, wherein the length of A is from 5 to 18 carbon atoms, and wherein the substituents are independently selected from $C_{1-6}$ alkyl, $C_{2-6}$ alkenyl, $C_{2-6}$ alkynyl, halogen, $C(O)R_{10}$, $OR_{11}$, $SR_{11}$, $CH_2OR_{11}$, $CH_2NR_{12}R_{13}$, $NR_{12}R_{13}$, $CONR_{12}R_{13}$, amino acids, dipeptidyl, tripeptidyl, tetrapeptidyl and pentapeptidyl;

$R_{10}$ is selected from OH, $OR_{11}$, $C_{1-6}$ alkyl;

$R_{11}$ is selected from the group consisting of hydrogen, optionally substituted $C_{1-10}$ alkyl, optionally substituted $C_{2-10}$ alkenyl, optionally substituted $C_{2-10}$ alkynyl, and optionally substituted $C_{3-10}$ cycloalkyl, wherein said optional substituents are independently selected from $C_{1-6}$ alkyl, $C_{2-6}$ alkenyl, aryl, and hydroxyl;

$R_{12}$ and $R_{13}$ are independently selected from the group consisting of hydrogen, optionally substituted $C_{1-10}$ alkyl, optionally substituted $C_{2-10}$ alkenyl, optionally substituted $C_{2-10}$ alkynyl, optionally substituted $C_{3-10}$ cycloalkyl, optionally substituted alkylheteroaryl, wherein said substituents are independently selected from $C_{1-6}$ alkyl, $C_{2-6}$ alkenyl, aryl, hydroxyl, halogen, amino, and $C(O)OR_{11}$; or $R_{12}$ and $R_{13}$, together with the nitrogen atom to which they are attached may form an optionally substituted heterocycloalkyl group, wherein said substituents are independently selected from $C_{1-6}$ alkyl, $C_{2-6}$ alkenyl, hydroxyl, halogen, amino, and $C(O)OR_{11}$.

8. A compound according to claim 1, selected from 1,11-bis-(tributylammonium)undecane, 1,16-bis-(tributylammonium)hexadecane, 1,12-bis-(tripentylammonium)dodecane, 1,12-bis-(trihexylammonium)dodecane, 1,12-bis-(trioctylammonium)dodecane, 1,12-bis-(triisobutylammonium)dodecane, 1,12-bis-(triisopentylammonium)dodecane, and 1,12-bis-(1-butylpyrrolidinium)dodecane.

9. A method for treating and/or inhibiting a bacterial or fungal infection in a vertebrate, said method comprising administering to said vertebrate an effective amount of at least one compound according to claim 1.

10. The method according to claim 9, wherein the infection is a fungal infection.

11. The method according to claim 9, wherein the infection is a bacterial infection.

12. A method of inhibiting phospholipase in an organism comprising contacting said organism with an effective amount of at least one compound according to claim 1.

13. The method according to claim 12, wherein the organism is selected from bacteria, fungi, virus, and parasite.

14. The method according to claim 12, wherein the phospholipase is Phospholipase B.

15. The method according to claim 12, wherein the organism is selected from the group consisting of: bacteria, fungi and virus.

16. A method for identifying an antimicrobial agent comprising contacting microbial cells with a compound according to claim 1 suspected of having antimicrobial properties, determining whether said compound inhibits a microbial phospholipase enzyme, wherein inhibition of said phospholipase enzyme indicates antimicrobial activity, and thereby identifying an antimicrobial agent.

\* \* \* \* \*